US012250981B2

(12) United States Patent
Hopkins et al.

(10) Patent No.: US 12,250,981 B2
(45) Date of Patent: Mar. 18, 2025

(54) ANALOG CONTROL SYSTEMS AND METHODS FOR ADAPTIVE APPAREL

(71) Applicant: NIKE, Inc., Beaverton, OR (US)

(72) Inventors: Timothy P. Hopkins, Lake Oswego, OR (US); Bobby LeGaye, Beaverton, OR (US); Mark Bruce, Beaverton, OR (US); Peter Williams, Beaverton, OR (US); Austin J. Orand, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 147 days.

(21) Appl. No.: 17/726,167

(22) Filed: Apr. 21, 2022

(65) Prior Publication Data

US 2022/0338581 A1    Oct. 27, 2022

Related U.S. Application Data

(60) Provisional application No. 63/178,553, filed on Apr. 23, 2021.

(51) Int. Cl.
*A41F 15/00*    (2006.01)
*A41F 1/00*    (2006.01)
*A41C 3/00*    (2006.01)

(52) U.S. Cl.
CPC .......... *A41F 15/002* (2013.01); *A41C 3/0028* (2013.01); *A41F 1/008* (2013.01); *Y10T 24/21* (2015.01)

(58) Field of Classification Search
None
See application file for complete search history.

(56) References Cited

U.S. PATENT DOCUMENTS

| 2,717,437 | A | * | 9/1955 | De Mestral | A44B 18/0038 |
| | | | | | 428/95 |
| 5,042,177 | A | * | 8/1991 | Schoch | A43C 11/165 |
| | | | | | 36/50.1 |

(Continued)

FOREIGN PATENT DOCUMENTS

| CN | 117545392 A | 2/2024 |
| JP | 2024515743 A | 4/2024 |

(Continued)

OTHER PUBLICATIONS

"International Application Serial No. PCT US2022 025754, International Search Report mailed Aug. 5, 2022", 4 pgs.
"International Application Serial No. PCT US2022 025754, Written Opinion mailed Aug. 5, 2022", 5 pgs.
"International Application Serial No. PCT/US2022/025754, International Preliminary Report on Patentability mailed Nov. 2, 2023", 7 pgs.

(Continued)

*Primary Examiner* — Grace Huang
(74) *Attorney, Agent, or Firm* — Schwegman, Lundberg & Woessner, P.A.

(57) ABSTRACT

An adaptive support garment integrating directional fabrics to assist in providing adaptive support to select portions of the garment is discussed herein. The adaptive support garment can include a first directional fabric, a second directional fabric, and a tension device. The first directional fabric includes first directional fibers, and the first directional fabric can be coupled to a fixed portion of the adaptive support garment. The second directional fabric includes second directional fibers, and the second directional fabric can be coupled to a movable control structure portion of the adaptive support garment. The tension device can be coupled to the movable control structure and configured to apply a tension in a first direction on the movable control structure. In operation, the first directional fibers can engage with the second directional fibers to resist movement in a second direction opposite the first direction.

26 Claims, 46 Drawing Sheets

(56) References Cited

U.S. PATENT DOCUMENTS

| | | | |
|---|---|---|---|
| 7,374,523 B2* | 5/2008 | Weir | A63B 21/4007 |
| | | | 482/148 |
| 11,825,886 B2* | 11/2023 | Munro | A41C 3/0057 |
| 2011/0072566 A1* | 3/2011 | Kovacevich | F41H 1/02 |
| | | | 2/2.5 |
| 2013/0203319 A1 | 8/2013 | Torres et al. | |
| 2014/0259301 A1* | 9/2014 | Berns | A43C 9/00 |
| | | | 2/336 |
| 2016/0037830 A1 | 2/2016 | Swendseid et al. | |
| 2017/0273365 A1* | 9/2017 | Muhlenfeld | A41C 3/0028 |
| 2020/0375506 A1* | 12/2020 | Bishop | G16H 50/30 |
| 2021/0361456 A1* | 11/2021 | Rutckyj | A61F 5/0123 |
| 2022/0408852 A1* | 12/2022 | Maeda | H04W 4/70 |

FOREIGN PATENT DOCUMENTS

| | | |
|---|---|---|
| KR | 20240000577 A | 1/2024 |
| WO | 2020076978 | 4/2020 |
| WO | 2022226188 | 10/2022 |

OTHER PUBLICATIONS

"Japanese Application Serial No. 2023-565320, Voluntary Amendment filed Dec. 25, 2023", w/ English claims, 6 pgs.

"European Application Serial No. 22722060.5, Response to Communication Pursuant to Rules 161 & 162 Filed Jun. 14, 2024", 89 pgs.

* cited by examiner

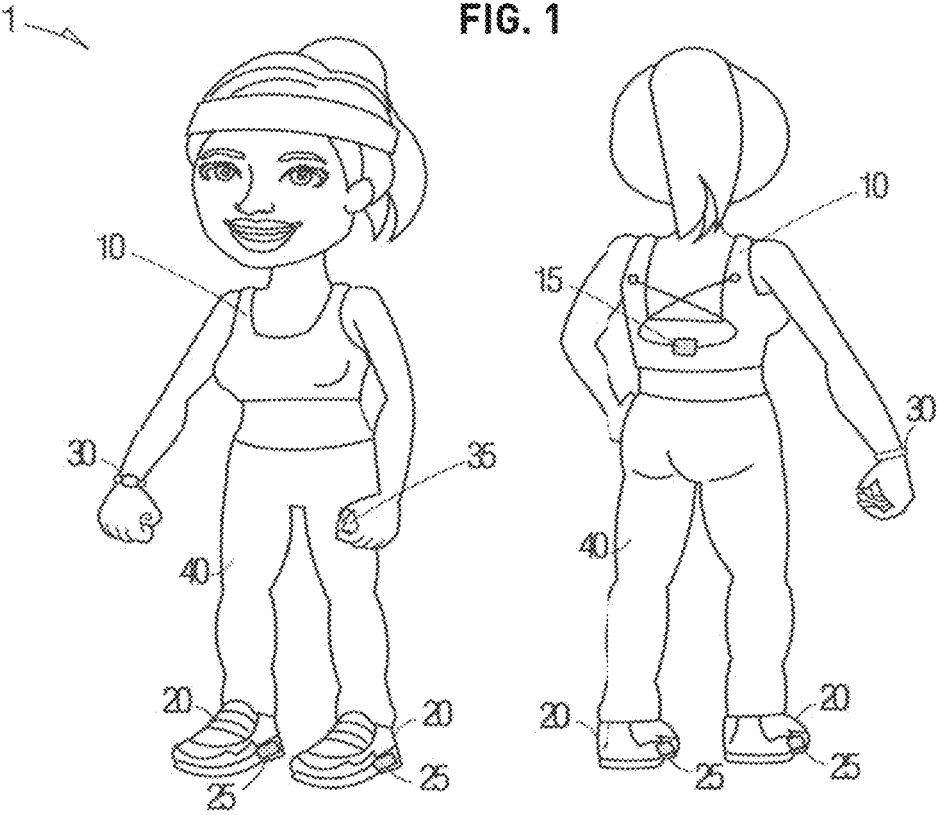
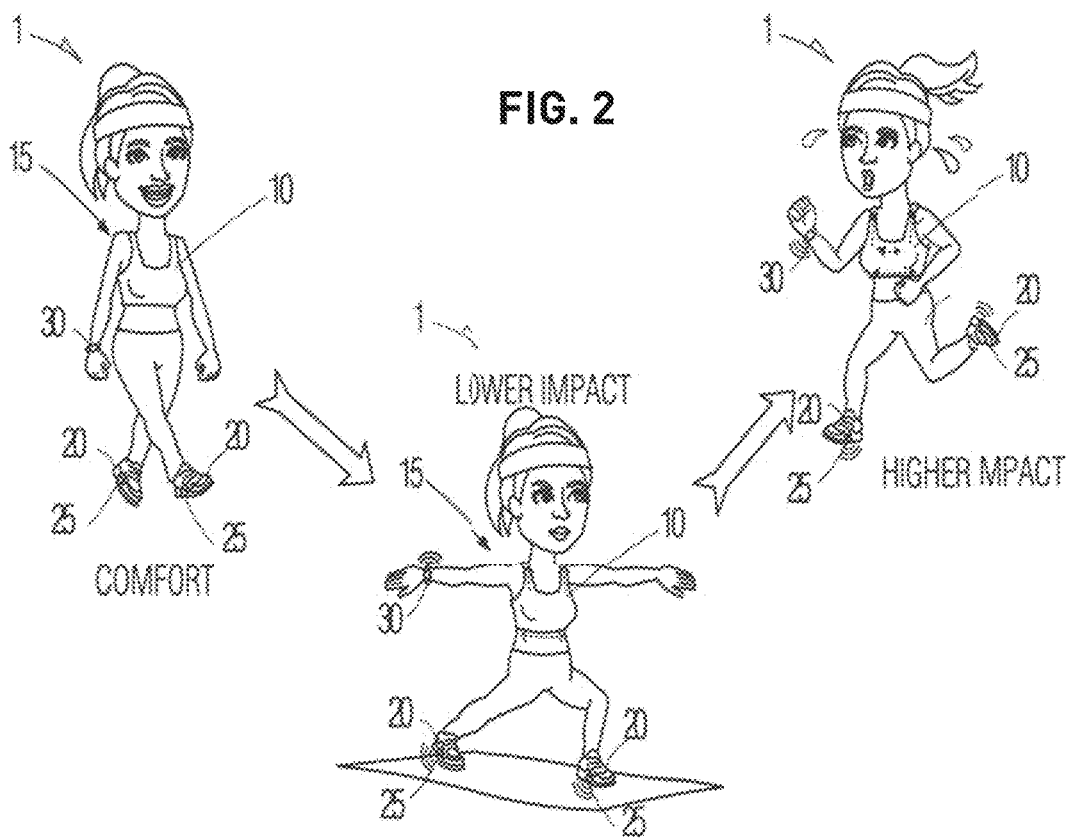

ANALOG CONTROL SYSTEMS AND METHODS FOR ADAPTIVE APPAREL

PRIORITY APPLICATIONS

This application claims the benefit of priority to U.S. Provisional Application Ser. No. 63/178,553, filed Apr. 23, 2021, the content of which is incorporated herein by reference in its entirety.

BACKGROUND

Apparel, such as bras, tops, bottoms, tights, leggings, underwear, hats or other head coverings, etc. can be constructed to provide support to a wearer during various activities. Such articles of apparel can be configured to accommodate differences in body sizes and body types, and can be configured for particular activities. Some apparel can have limited adjustment mechanisms or adaptability.

OVERVIEW

The present inventors have recognized, among other things, a need for improved fit and function of apparel, such as bras, tights, and various other garments, undergarments, or base layers (also referred to herein as support garments), hats, helmets, head coverings, footwear, and other apparel. One example includes an adaptive bra that can provide a customized fit for individual body contours and can automatically or manually adjust to different dynamic conditions (e.g., changes in activity level).

For example, an adaptive bra can adjust from maximum comfort to maximum breast support as a wearer transitions from resting to strenuous exercise. An adaptive bra can also utilize automated adjustment mechanisms coupled to movement sensors to dynamically adjust to inhibit unwanted movement of the breasts during activities, such as running as an example. Adaptive apparel, such as adaptive tights, athletic supporters, or other articles discussed below, can also provide dynamic support with the potential to enhance performance or reduce potential for injury. Numerous examples of the various support apparel introduced here are discussed throughout the following disclosure.

The term "support garment" as used herein is meant to encompass any number of support garments such as bras, sport bras, tank tops, camisoles with built-in support, swimming suit tops, body suits, and other styles or types of support garments used to support body tissue (e.g., breast tissue). Further, the term "supportive region" as used herein is meant to encompass any type of structure that is in contact with or intended to be positioned adjacent to the wearer's breasts, other reproductive organs, and/or soft tissue benefiting from enhanced support when the support garment is worn. In example aspects, for a typical wearer, a support garment comprises a first breast contacting surface configured to contact or be positioned adjacent to, for instance, a wearer's right breast and a second breast contacting surface configured to contact or be positioned adjacent to, for instance, a wearer's left breast. In example aspects, the support garment comprises separate distinct cups (e.g., molded or unmolded) with each cup comprising a breast contacting surface and each cup configured to cover or encapsulate a separate breast, or the support garment may comprise a unitary or continuous band of material that makes contact with both of the wearer's breasts.

The inventors have recognized need for dynamically modifying the support provided by certain types of support apparel based on a change in activity level. The need for modifying the support stems from a desire for long-term comfort contrasted with the potential for improvements in functionality during activities. Accordingly, a system has been developed including activity sensors, such as inertial measurement units (IMUs), global positioning sensors (GPS) or heart rate monitors, among others, in communication with a control circuit that sends commands to an adaptive support apparel including an adaptive engine to facilitate automatic changes in support, such as based on changes in detected activity levels. These systems can provide a wearer all-day comfort without compromising performance. Without the systems, methods, and devices discussed herein, a wearer may otherwise need to change support apparel for different activities or struggle with multiple manual adjustments.

The activity sensors discussed herein can include any sensor that provides an indication of a level of physical activity of a user, as well as any sensor that provides an indication of forces (e.g., dynamic or static) imparted on an adaptive support garment during use. Sensors can be embedded into an adaptive support garment to provide data related to forces imparted on portions of a support structure, such as straps, laces, cables, or regions of fabric.

This section is intended to provide an overview of subject matter of the present patent application. It is not intended to provide an exclusive or exhaustive explanation of the invention. The detailed description is included to provide further information.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 1 illustrates generally portions of a system that can include an adaptive support garment.

FIG. 2 illustrates generally examples of an adaptive support garment in use.

DETAILED DESCRIPTION

Figure 3:
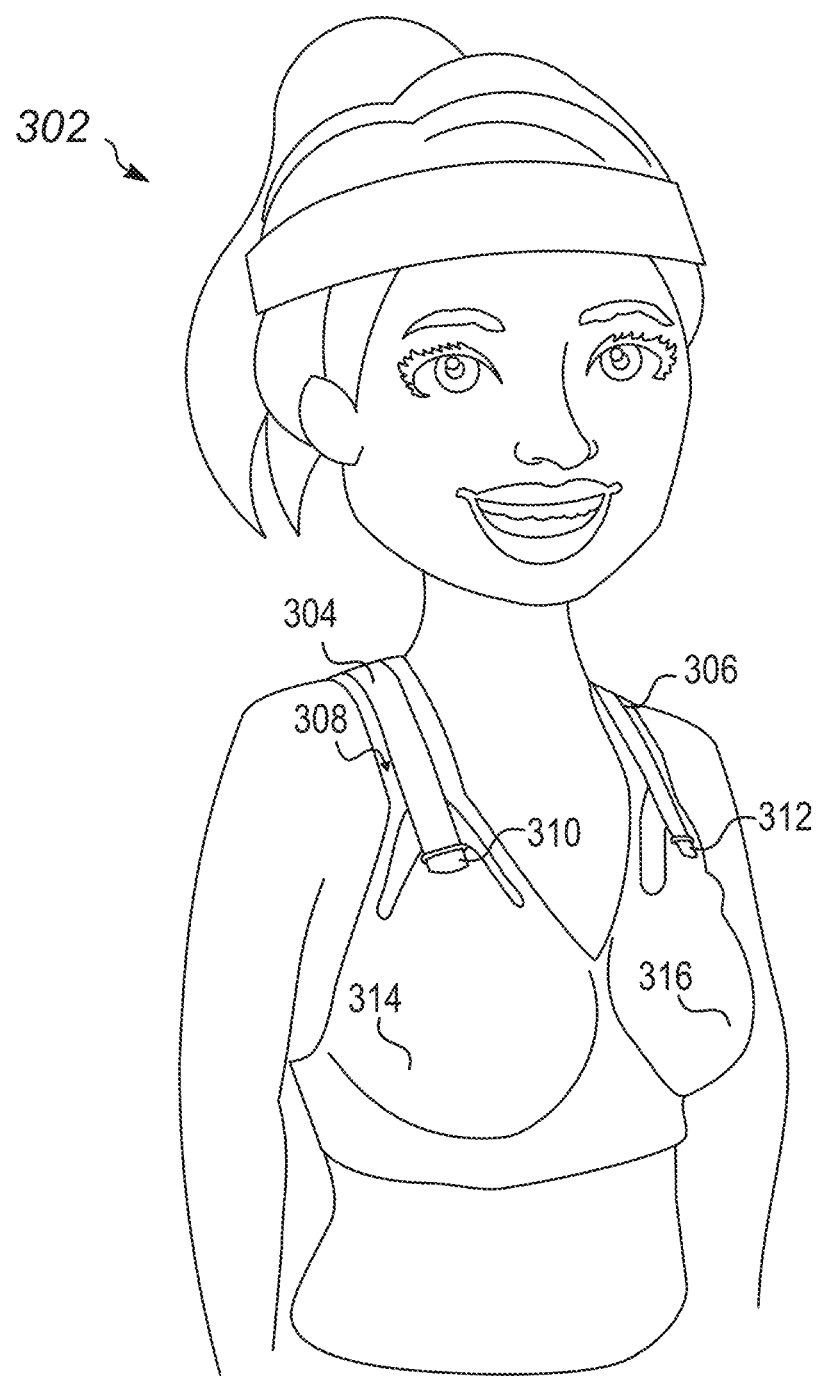
FIG. 3 illustrates generally a front view of an adaptive support apparel in accordance with some embodiments.

The description that follows describes systems, methods, techniques, instruction sequences, and computing machine program products that illustrate example embodiments of the present subject matter. In the following description, for purposes of explanation, numerous specific details are set forth in order to provide an understanding of various embodiments of the present subject matter. It will be evident, however, that embodiments of the present subject matter may be practiced without some or other of these specific details. Examples merely typify possible variations. Unless explicitly stated otherwise, structures (e.g., structural components, such as modules, devices, systems or components thereof) are optional and can be combined or subdivided, and operations (e.g., in a procedure, algorithm, or other function) can vary in sequence or be combined or subdivided.

FIG. 1 is an illustration of a system including an adaptive support garment and associated electronics, according to some example embodiments. In this example, the adaptive support apparel system 1 includes components such as, an adaptive support garment 10, a footwear assembly 20, and a smart watch 30. Optionally, the adaptive support apparel system 1 can also communicate with a smartphone 35 for control or adjustment of parameters. In this example, the footwear assembly 20 includes an activity sensor 25, and the adaptive support garment 10 includes an adaptive engine 15. In this example, the adaptive engine 15 couples to a control device and/or control lace system that controls an adaptive support structure within the adaptive support garment 10.

In this example, the footwear assembly 20 includes an activity sensor 25 that can include sensors such as an accelerometer, a gyroscope, a temperature sensor, a magnetometer, a heart rate sensor, or a global positioning sensor (GPS) to detect a change in activity level. In one example, the footwear assembly 20 includes an inertial measurement unit (IMU), which combines at least accelerometers and gyroscopes to provide a specific force, orientation, or angular rate of change for a monitored body. Data from the IMU can be used to detect movements, such as foot strike or cadence among other things. In this example, the data from the activity sensor 25 is communicated to the smart watch 30 or smartphone 35 for processing to determine whether a change in adaptive support is needed based on the activity data from the activity sensor. In another example, the activity data base be sent directly to the adaptive engine 15 for processing and determination of adaptive support level needed.

Foot strike data is just a portion of a broader array of step metrics that can be determined from sensors, such as activity sensor 25 (e.g., IMU and Force sensor combination). Step metrics can include individual steps or step count. A step can be defined for this metric based on parameters such as, minimum vertical force threshold, minimum average vertical force per step, minimum step time and maximum step time. Step metrics can also include contact time, which is calculated per foot per step using a force single (e.g., time when vertical force>50N). Another step metric is swing time, which is calculated per foot per step using force single (e.g., time when vertical force<50N until that foot creates a force>50N). Step metrics also include cadence, which can be defined as the inverse of the sum of the contact and swing time for each foot using force signal. Step length is another step metric calculated using a force signal (e.g., sum of contact and swing time multiplied by average speed). Another step metric is impact, which can be calculated in at least two ways. Impact can be a peak rate of rise of the vertical ground reaction force, or an active peak of the vertical ground reaction force. Impulse is another step metric that is calculated per foot per step using a force signal (e.g., integral of the ground reaction force magnitude). Contact is another step metric derived from motion data. For example, using IMU data sampled at 200 Hz to determine foot angle relative to horizontal at the time of foot contact. Contact can include rearfoot, midfoot, and forefoot angles. Any of the step metrics discussed here can be used as activity data or in addition to other activity data to assist in determining an activity level or directly to determine a target support level for an adaptive support garment.

In this example, one or each of the adaptive engine 15, smart watch 30, and smartphone 35, separately or in conjunction with one another or by accessing remote computing resources, includes a control circuit that processes the activity data and sends commands to the adaptive engine 15 to change support characteristics as needed. The adaptive engine 15 receives commands and activates a system to adjust an adaptive support structure through interactions with a clutch system coupled to the adaptive engine 15.

FIG. 2 illustrates a user of an adaptive support apparel system transitioning between different activities that might require, or benefit from, various levels of support. In this example, the activity sensor 25, illustrated within the footwear assembly 20, operates to detect different activity levels ranging from a relaxed walk to moderate exertion doing yoga to more extreme impact and exertion involved in running. In this example, the activity sensor 25 transmits data to a control circuit in the smart watch 30, which is running an application that determines a current activity level based on the activity data interpreted from the sensor(s). In some examples, the smart watch 30 can also include activity sensors that also send activity data to the control circuit operating on the smart watch 30 to provide additional activity level information to inform a decision to increase or decrease the support provided by the adaptive support garment 10, such as an adaptive bra as in this example. For example, the smart watch 30 can include an integrated heart rate monitor that can be used as additional information related to activity level.

In the comfort zone, the adaptive apparel support system 1 detects low levels of physical activity that have been determined to correspond to a relaxed level of support required from an adaptive support garment. Accordingly, the control circuit commands the adaptive engine 15 to activate and adjust the adaptive support garment 10 to a comfort setting. The control application (e.g., application operating the control circuit) can include a user interface that provides a user access to different settings for the adaptive support garment. In an example, the settings can include associating different support levels with different pre-defined activity levels, such as resting=comfort support level (e.g., low level of support) and higher impact=performance support level (e.g., a high level of support). Other mappings can be created, and a user interface can be presented to allow a user to generate custom mappings, Table 1 illustrates an example mapping table for Activity Level—Support Level mapping.

TABLE 1

| Activity Level | Support Level |
| --- | --- |
| Resting (no exertion, no impact) | Comfort-Minimum Support |
| Walking (moderate exertion, low impact) | Recreation-Moderate Support |
| Yoga (moderate exertion & impact) | Sport-Enhanced Support |
| Running (high exertion & impact) | Performance-Superior Support |

As illustrated, a user can transition from Comfort to Lower Impact by increasing exertion and/or impact detected by the activity sensors. Dynamically, upon detecting a transition the control circuit in the smart watch 30 commands the adaptive engine 15 to increase the support level provided by the adaptive support garment 10. If the user reverts to a Comfort level of activity (e.g., resting or walking), then the control circuit can command the adaptive engine 15 to relax the support level back to a comfort level of support. Alternatively, if the user increases activity by going for a run, the system can dynamically respond with the adaptive engine 15 increasing the support level to a higher impact (performance) level of support.

In certain examples, a user can select from multiple different activity related parameters (e.g., heart rate, cadence, impact, etc.) and associate different levels of each parameter with different support levels. For example, a user can create a running activity classification that uses heart rate and cadence as triggers. The running activity can then be mapped to a high support level. The support level can also be configured by associating different support structure adjustments to a particular support level, such as a lace tension for a lacing system-based support structure.

Support Garment

FIG. 3 illustrates generally an apparel example 302. A female front view of support garment 302 is shown having a left front view of left lace system 304, a right front view of right lace system 306, a left shoulder strap 308, a left fixing point 310, a right fixing point 312, a right cup 316, and a left cup 314.

The apparel example 302 is an example of a support garment for a wearer having a textile layer forming a supportive region configured to adjustably inhibit displacement of a body part of the wearer positioned proximate the supportive region. The apparel example 302 may also include a strap affixed to a portion of the textile layer. The left and right lace systems 304 and 306 may encase a control mechanism including cables and/or pulleys to selectively control movement of a breast within either the right cup 316 or left cup 314.

The apparel example 302 is of a sports bra and the supportive region is a right cup 316 and a left cup 314 of the sports bra. The lace systems 304 and 306 are individually addressable or controllable by a controller (e.g., by the support garment control device 1612) to selectively adjust an absolute or relative amount by which the support garment allows displacement of the body part. For example, if a wearer has a larger left breast, the left cup 314 may provide a different level of support than the right cup 316 provides for the right breast.

Figure 4:
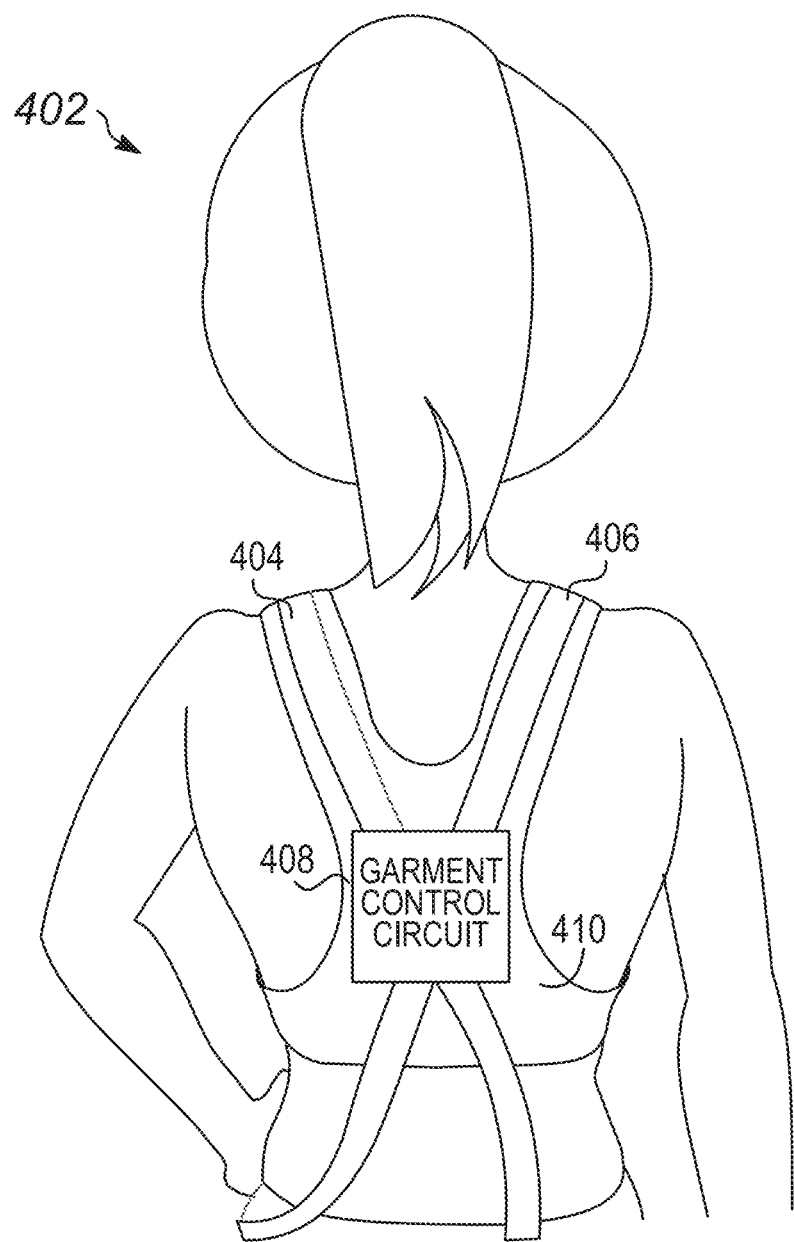
FIG. 4 illustrates generally a back view of an adaptive support apparel in accordance with some embodiments.

FIG. 4 illustrates a second view of an adaptive support apparel example 402 similar to the adaptive support apparel example 302. A back view of support garment 402 shows a back view of left lace system 404 and back view of right lace system 406 The support garment may include an integrated garment control unit 408 embedded within or coupled to the support garment. The garment control unit 408 can include a system or processor configured to control actuation of a clutch. Garment control unit 408 may be permanently or semi-permanently affixed to a back portion 410 of adaptive support apparel example 402. In some examples, the techniques, as described in FIG. 6, can be implemented using the garment control unit 408 is coupled to the adaptive support apparel example at various locations (e.g., in between the breasts in a front view of the adaptive support apparel or between the shoulder blades as shown in FIG. 4).

The support garment is configured to inhibit displacement of the wearer's body part when the wearer or the wearer's body part is measured at an acceleration rate higher than a threshold. The support garment is configured to relax or allow the support garment to flex.

Figure 5:
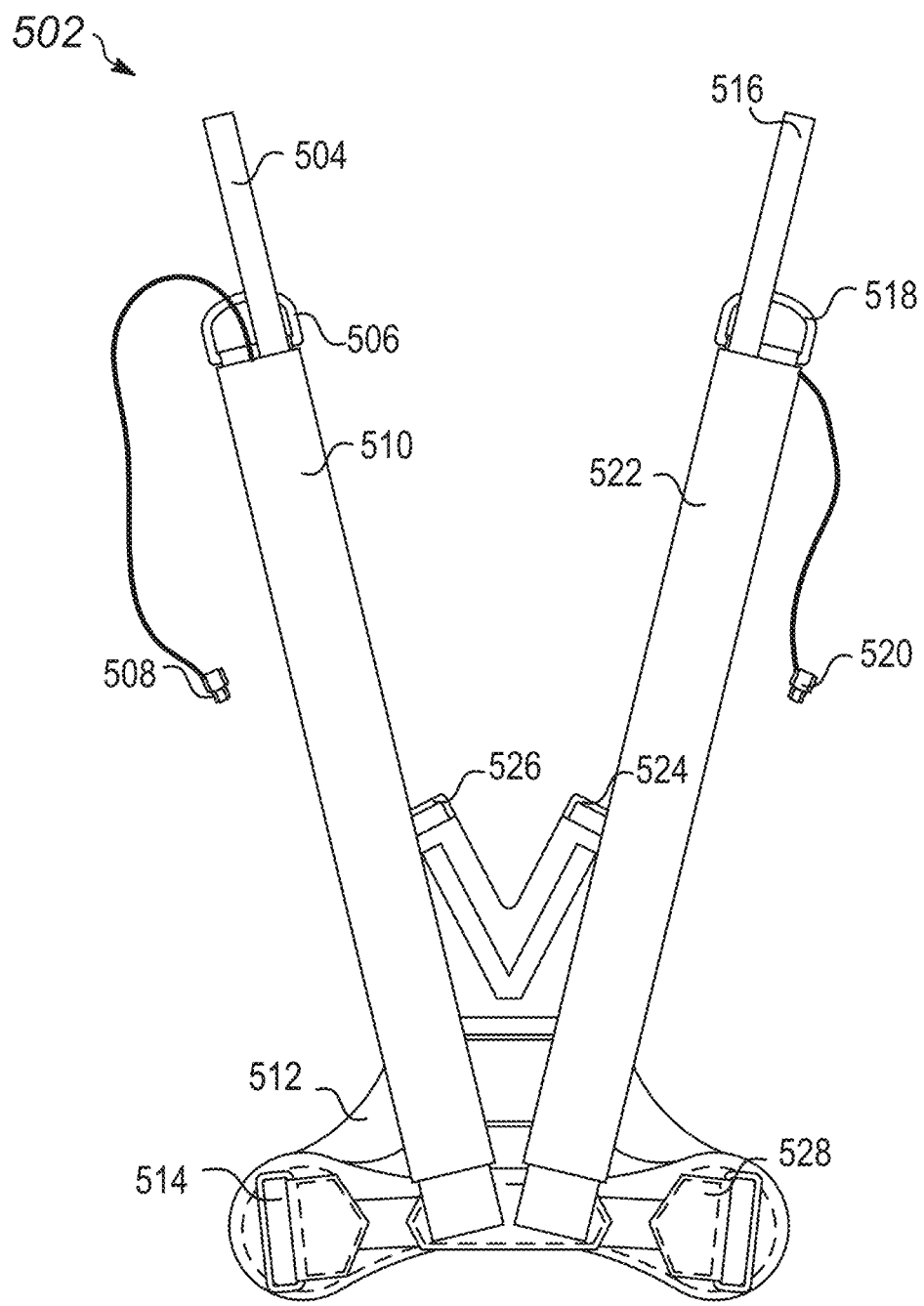
FIG. 5 illustrates an example of a modular control system for use in conjunction with an adaptive support apparel.

FIG. 5 illustrates an example of a modular control system 502 for use in conjunction with an adaptive support apparel. The example shows a back view of a left lace system 510 and a back view of a right lace system 522. The garment control unit 502 can be a modular device configured for attachment to the support garment 302 (FIG. 3) and may include mechanical mechanisms for providing dynamic support to the wearer (e.g., air damper 900 and mechanical/digital clutch systems discussed below) and various additional sensors. Various mechanisms as described herein may be included in the left and right lace systems 510 and 522. Alternatively, the left and right lace systems 510, 522 can be coupled to the various mechanisms discussed herein. The garment control unit 502 includes a left adjusting strap 504 and a right adjusting strap 516 that may be controlled by the garment control unit to apply various tensions to the support garment. The right and left adjusting straps 504 and 516 are coupled to a base 512 and can be attached to the support garment 302 or 402 by attachment mechanisms 506, 514, 518, 524, 526, and 528. Attachment mechanisms can include O-rings, d-rings, hook and loop fasteners, zippers, snaps, or any other type of suitable attachment mechanisms for selectively coupling the garment control unit 502 to a portion of a support garment. The garment control unit 502 is further coupled to the support garment and/or a sub-component attached to the support garment through right connector 520 and left connectors 508. The right and left connectors 520 and 508 may be used to attach additional modular units including additional sensors such as accelerometers, gyroscopes, GPS, heart rate monitor, EKG monitor, etc.

In some embodiments, the integrated garment control unit 502 may be placed at a location on the front of the support garment for example between the breasts or placed at a location on the back of the support garment for example between the shoulder blades. The modular unit can help provide dynamic support of a user's body as described herein, for example, without integration with or permanent affixation to the support garment (e.g., sewn in or otherwise permanently affixed). The modular unit may include one or more adjusting straps (e.g., right adjusting strap 516 and left adjusting strap 504) to selectively couple to the support garment to provide the functionalities as described with respect to FIG. 3-4.

Figure 6:
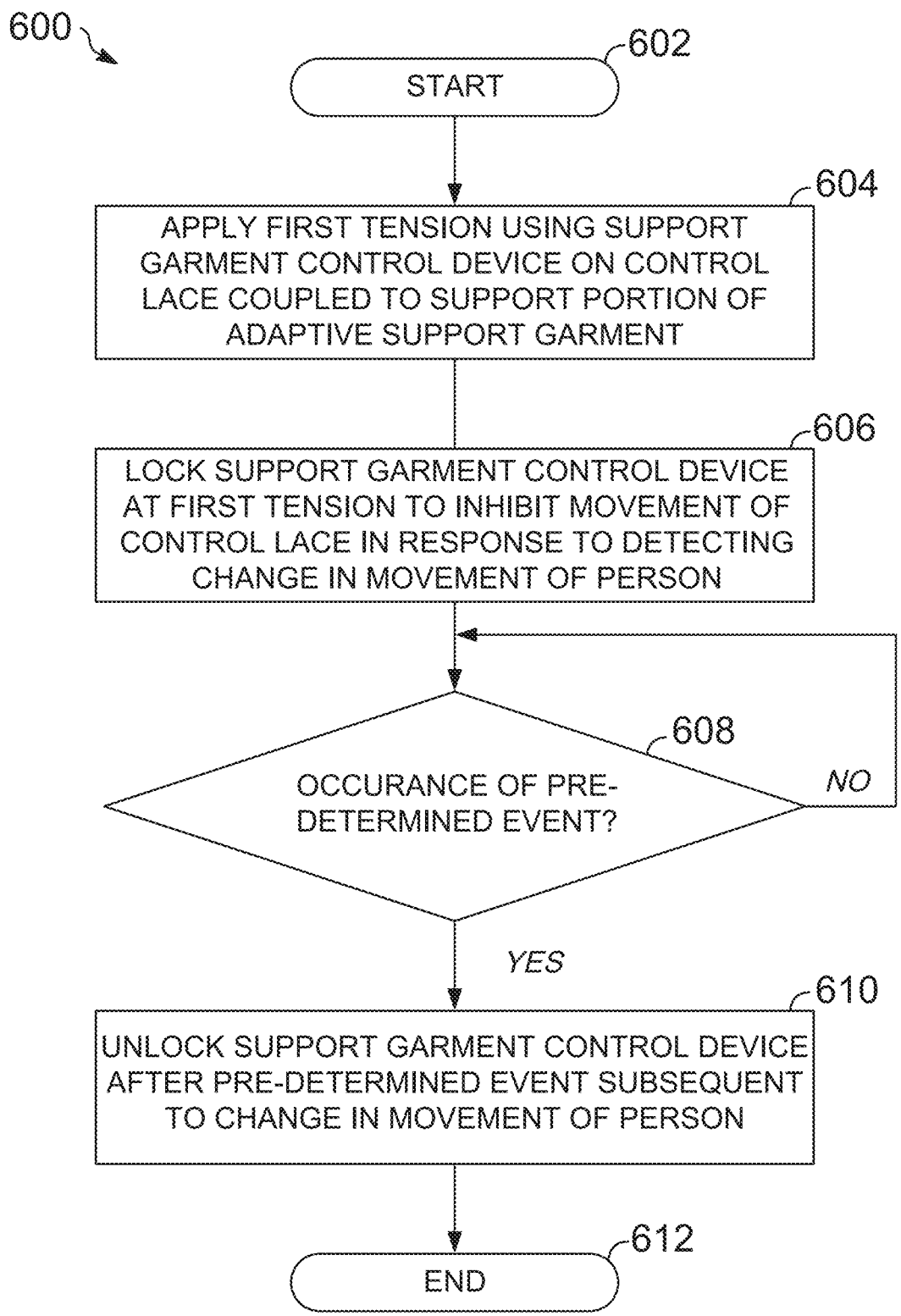
FIG. 6 is a flowchart illustrating an example technique for configuring a support garment to provide dynamic support to a wearer in accordance with some embodiments.

FIG. 6 is a flowchart illustrating an example method 600 for selectively controlling a portion of an adaptive support apparel, according to an example embodiment. The method can be performed by any of the control mechanism discussed herein with regards to FIGS. 9A-13I in cooperation with the adaptive support apparel discussed above.

In some embodiments, the method 600 includes operations for providing dynamic support for an appendage of a person. The method begins at operation 602 and at operation 604, proceeds by applying a first tension using a support garment control device on a control lace coupled to a support portion of an adaptive support garment. In some examples, at an operation preceding operation 604, a support garment control device is attached to a modular panel including a mechanical control system to be detachably integrated into the adaptive support garment (e.g., FIG. 5). Attaching the support garment control device to the modular panel may include coupling the control lace to the support garment control device. The coupling may be achieved via connectors shown in FIG. 5, via hook-and-loop mechanical fasteners, zippers, snap buttons, or any suitable mechanism allowing selective coupling of the control lace to the support garment control device.

At operation 606, the support garment control device is locked at the first tension to inhibit movement of the control lace in response to detecting a change in movement of the person. In some examples, a movement input is detected and/or received from a sensor adapted for monitoring movements of the person. The output from the sensor is evaluated to detect the change of movement of the person. The output from the sensor may be evaluated to predict a future motion of the person to preemptively apply the first tension on the control lace. Additionally, the output of the sensor may be evaluated to determine a duration of time for the control lace to remain locked at the first tension. Based on the output of the sensor, a direction and/or acceleration rate of the person can be determined. The acceleration and/or direction is used to adjust the first tension according to the direction and acceleration of the person.

For example, a person is wearing an adaptive support garment such as a sports bra. The person is training for a "mud run" competition and will be performing a series of jogging, running, jumping, and crawling exercises. Based on the detected direction, acceleration, and/or intensity of the movements of the person, the support garment control device applies a tension on a control lace (e.g., control lace system 510, 522 FIG. 5) and the support garment control device is locked to inhibit movement. When the person is running, the support garment control device is locked at a first tension. When the person is jumping, the support garment control device is locked at a second tension and possibly for a different time duration than when the person is running. Various tensions and locking intervals are possible depending on various conditions and movements of the person.

At operation 608, a determination is made whether a pre-determined event subsequent to the change in movement of the person has occurred. If yes, the method 600 continues at operation 610 to unlock the support garment control device.

In some examples, the pre-determined event includes expiration of a time delay since locking the support garment control device. In other examples, the pre-determined event includes receiving an indication (e.g., from a sensor) that the movement of the person has changed in acceleration, direction, and/or frequency. In yet other examples, the pre-determined event can include a tension on a control lace exceeding or transgressing a threshold value.

After the support garment control device is unlocked at operation 610, in some examples, the method includes applying a second tension on the control lace, the second tension being a higher tension than the first tension. The support garment control device is locked at the second tension to restrict movement of the control lace in response to detecting a second change in movement of the person. The second change in movement of the person may include an acceleration of the person in one or more directions. The support garment control device is unlocked after a second pre-determined event subsequent to the second change in movement of the person. The second pre-determined event may in some embodiments be the same pre-determined event that was detected to unlock the support garment control device at the first tension.

The method may end at operation 612 or in some examples, repeat as determined necessary to provide dynamic support for a wearer while the wearer is in motion.

Figure 7:
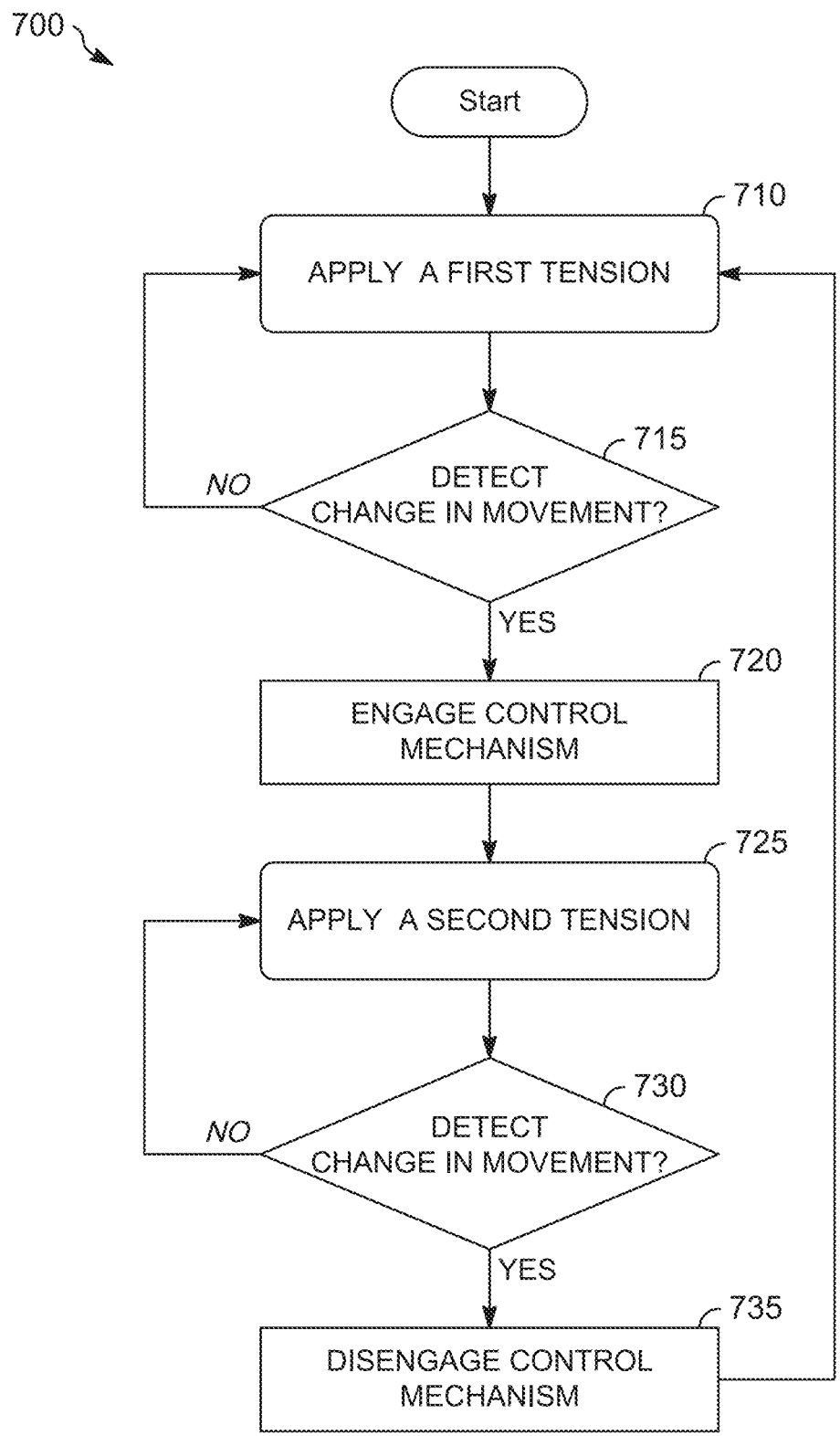
FIG. 7 is a flowchart illustrating an example technique for operating a control mechanism within an adaptive apparel system, according to various example embodiments.

FIG. 7 is a flowchart illustrating an example technique 700 for controlling a portion of an adaptive support apparel, according to an example embodiment. The technique 700 can be performed by any of the control mechanisms discussed below in FIGS. 9A-14B but will be discussed in view of the rotary damper control mechanism 1100 and the digital rotary clutch control mechanism 1200 as examples. The first example implementation of techniques 700 is discussed in view of the rotary damper control mechanism 1100 and will not involve the optional operations for detecting a change in movement at 715 and 730. The rotary damper control example is comparable to how the technique 700 applies to all analog control system discussed herein.

In an example, the technique 700 includes operations for applying a first tension on a lace cable at 710, engaging a control mechanism at 720, applying a second tension on a lace cable at 725, and disengaging the control mechanism at 735. In this example, the technique 700 begins as a user engages in an impact oriented physical activity, as indicated in the flowchart the technique 700 is cyclical and continues during the entire impact oriented physical activity. At 710, the technique 700 begins with the control mechanism, a rotary damper control mechanism 1100 in this example, applying a first tension on a lace cable that is coupled to a support portion of an adaptive support apparel, such as an adaptive bra. The rotary damper control mechanism 1100 applies the first tension in a retracting (or free) mode where the lace spool 1110 is biased by the rotary bias member 1118 to retract the lace cable (or allow for extension of the lace cable if tension on the lace cable exceeds the bias provide by the rotary bias member 1118). In this initial retracting/free mode, the locking ring 1120 rotates counter-clockwise until the lock wedge 1125 disengages the damper mechanism 1130 from the spool gear 1115 and the upper lock release tab 1126 engages a lock release housing slot (or tab) 1107 to release the friction between the locking ring 1120 and the lock ring groove 1114 (friction is generated by the locking tension member 1121). As lace is retracted by the lace spool 1110, the locking ring 1120 and lock wedge 1125 are naturally held in a position to keep the damper mechanism 1130 disengaged. However, as the lace cable is pulled out of the control mechanism by tension exceeding the rotary bias member 1118, the technique 700 transitions to operation 720.

At 720, the technique 700 can continue with the rotary damper control mechanism 1100 engaging the damper mechanism 1130 due to the locking ring 1120 rotating clockwise to position the lock wedge 1125 in a neutral position that allows the damper mechanism 1130 to engage the lace spool 1110 (via either the damper gear 1136 or a drive gear 1140 engaging the spool gear 1115). Upon activation of the damper mechanism 1130, the technique 700 transitions to operation 725 by applying a second tension on the lace cable, which increases the tension required to extract additional lace cable from the control mechanism. At 725, the damper mechanism 1130 is engaged to apply the second tension on the lace cable as the lace cable is pulled from the control mechanism via the lace guide 1150. During operation 725, the lower lock release tab 1127 on the locking ring 1120 can engage a lock release housing tab 1106 extending from the lower housing 1101 to release friction between the locking ring 1120 and the lock ring groove 1114.

At 735, the technique 700 completes a cycle by disengaging the control mechanism. The rotary damper control mechanism 1100 can disengage when the lace spool 1110 rotates sufficiently counter-clockwise to engage the lock wedge 1125 portion of the locking ring 1120, which pivots the damper mechanism 1130 away from engagement with the lace spool 1110. Disengagement can occur as the lace cable retracts back into the control mechanism as the cycle of the impact oriented exercise enters a state that unloads the adaptive support apparel and release tension on the lace cable. After the technique 700 has disengaged the control mechanism at 735, the technique loops back to restart the cycle at operation 710 by applying the first tension on the lace cable. The technique 700 will continue to cycle through the operations in coordination with the impact oriented exercise, as transitions between the various operations is driven by tension on the lace cable induced by the forces experienced by the adaptive support apparel.

In an optional example of technique 700, the digital rotary clutch control mechanism 1200 (also referred to as control mechanism 1200) is the control mechanism performing the technique. In this example, the optional operations for detecting a change in movement 715 and 730 are included. As discussed above, the control mechanism 1200 includes a circuit board 1260 that can receive information from sensors coupled to an adaptive support apparel or the user. The sensors can be configured to detect changes in movement associated with the user that can be used by the control mechanism as triggers to transition between modes of operation. In this example, the digital rotary clutch control mechanism transitions between a free mode (ratchet disengaged) and a ratcheting mode (ratchet engaged).

The technique 700 can begin at 710 with the control mechanism 1200 applying a first tension to the lace cable. At 710, the control mechanism 1200 is in a free mode with the ratchet mechanism 1230 disengaged by the solenoids 1240A, 1240B (collectively referred to as solenoids 1240). In this mode, the lace spool 1210 is free to rotation in either direction, but is biased by the rotary bias member 1218 to apply a first tension on the lace cable. In this mode, the control mechanism 1200 is generally allowing the lace cable to extend outward. Similar to the rotary damper control mechanism 1100 discussed above, in the free mode within the control mechanism 1200 the locking ring 1220 rotates in a clockwise direction (as viewed from the device shown in FIGS. 12A-12B) until the upper lock release tab 1226 engages the lock release housing slot (or tab) (see e.g., FIG. 11C, 1107 for illustration of a similar structure) on the upper housing 1202 to release friction between the locking ring 1220 and the lock ring groove 1214. Releasing the friction between the locking 1220 and the lock ring groove 1214 allows the lace spool 1210 to apply more of the tension generated by the rotary bias member 1218 to the lace cable.

At 715, the technique 700 can continue with the control mechanism 1200 detecting a change in movement. In this example, the circuit board 1260 can receive a signal from one or more sensors worn by the user that can be interpreted to detect the change in movement. In other examples, detecting a change in movement may simply be a trigger signal received by the circuit board 1260 that does not require any additional processing or interpretation. Upon detecting the change in movement at 715, the technique 700 continues at 720 by transitioning to engage the control mechanism 1200. Engaging the control mechanism 1200 includes deactivating the solenoids 1240 to engage the ratchet mechanism 1230. Deactivating the solenoids 1240 retracts the solenoid shafts 1245A, 1245B and allows the ratchet tooth 1234 to engage the spool gear 1215. In the ratcheting mode, the control mechanism 1200 only allows for lace cable retraction. Accordingly, upon engagement of the control mechanism 1200, the technique 700 transitions to applying a second tension on the lace cable at 725. In this example, applying the second tension includes preventing extraction of additional lace cable from the control mechanism 1200 due to engagement of the ratchet mechanism 1230. In the ratcheting mode, the locking ring 1220 rotates with the lace spool 1210 in a counter-clockwise direction until the lower lock release tab 1227 engages the lock release housing tab (see e.g., FIG. 11E, 1106 for illustration of a similar structure) on the lower housing 1201. When the lower lock release tab 1227 engages the lock release housing tab, the friction between the locking ring 1220 and the lock ring groove 1214 is released (or reduced) by relieving tension between the tension interfaces 1222A, 1222B generated by the locking tension member 1221.

At 730, the technique 700 can continue by detecting another change in movement. Again, the detection of change in movement can arise from sensor data or be sent in as a trigger signal from an outside source. Alternatively, operation 730 can be triggered by a programmed time delay within the circuit board 1260 rather than any sort of sensor data. In some examples, the system can analyze cyclical sensor data to predict when the technique 700 should transition from operation 725 to operation 735 (e.g., perform operation 730). In this example, detecting the change in movement is based on a prediction algorithm analyzing past cycles to trigger the detection of the change in movement just prior to the actual change in movement, which can provide improved (or at least different) support characteristics.

Upon detecting the change in movement, the technique 700 transitions to operation 735 to disengage the control mechanism 1200. Disengaging the ratchet mechanism 1230 involves activating the solenoids 1240, which causes the solenoid shafts 1245A, 1245B to extend and push the ratchet solenoid arm 1235 and shift the ratchet tooth 1234 away from engagement with the spool gear 1215. After the ratchet mechanism 1230 is disengaged, the technique 700 cycles back to operation 710 and applies the first tension on the lace cable.

Control Systems

The following sections outline a number of control systems/devices that can be integrated into an adaptive support apparel, such as the adaptive bra discussed above. In these examples, the control systems are designed to assist in reducing movement of soft tissue, such as breast tissue, during moderate to high impact activities. The control systems are not necessarily designed to eliminate motion of the soft tissue, but rather reduce and/or alter the motion to make it more comfortable for the wearer of the support apparel.

Figure 8:
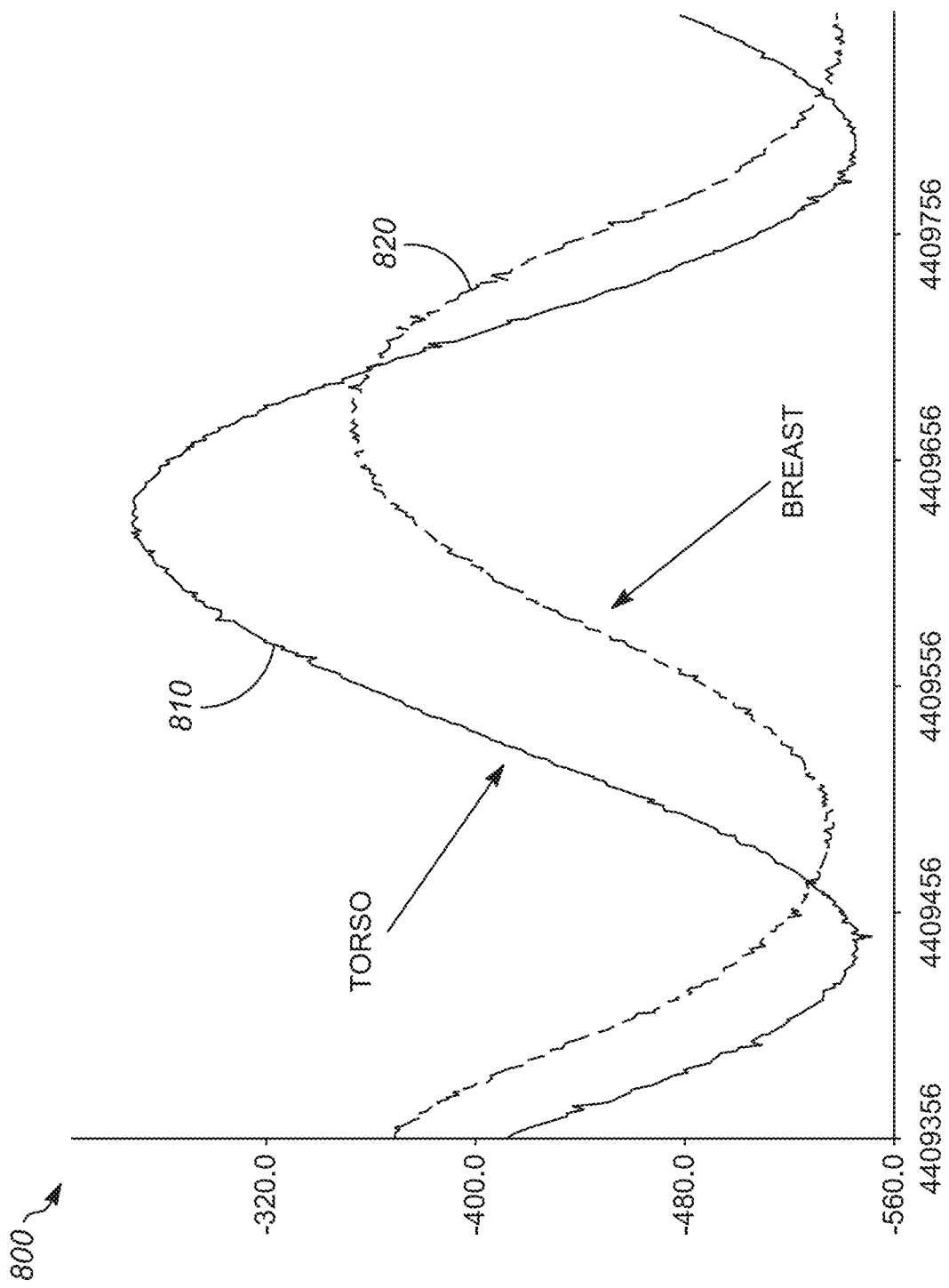
FIG. 8 is graph illustrating example effects of an adaptive support apparel using a control system to control soft tissue movement, in accordance with various example embodiments.

In the adaptive bra example, the control system can be utilized to reduce and/or offset the cyclical movement of breast tissue as compared to the center of mass. FIG. 8 illustrates exemplary results from an example implementation of one of the following control systems to control movement of breast tissue with respect to the center of mass of the wearer while running. The graph includes two lines, the center of mass line 810 (also marked TORSO) and the soft tissue line 820 (e.g., breast tissue). Each line illustrates movement of the respective object in reference to a fixed observation point. As illustrated by a comparison of the two lines, the soft tissue line 820 traces a cyclical pattern that includes lower amplitude and is offset from the center of mass line 810. The inventors have discovered that both attributes can contribute to improved comfort for a user. The lower amplitude is indicative of less movement, which results in lower acceleration forces during transition from movement in different directions. It is believed that the shift in the cycle of the soft tissue line 820 can also further reduce the compounding of forces on the soft tissue when moving in synchronization with the center of mass.

In contrast to an adaptive bra according to any of the discussed examples, using a typical sports bra during similar activity results in the amplitude of the breast tissue exceeding the amplitude of the torso. Reducing movement of the breast tissue, as demonstrated with the adaptive bra, results in less acceleration which results in less inertia that must be counteracted thereby increasing running efficiency. Using one of the adaptive bra examples discussed herein is comparable to carrying less weight while running or engaging in other high impact activities.

In these examples, the control system operates to dynamically adjust tension on straps that connect to the cups supporting the breast tissue. For the sake of discussion, the structure controlled by the control systems is discussed herein as a lace or lace cable, but could other structures suitable for incorporation into the various control systems. In these examples, the lace couples to the support structure of the adaptive apparel, such as straps of the adaptive bra. The control systems in various manners operate to retract, retain, and then release the lace in a particular time sequence to alter or restrict movement of the targeted soft tissue.

In this example, the control systems were programmed or designed to retract the lace for a time during or just after the propulsion phase through the swing phase. Retraction is typically timed to occur while the soft tissues are raising or neutral. Upon or just after the highest point of breast motion (or middle of the swing phase), the control system locks the lace to maintain the retracted position of the support structures and limit movement of the supported soft tissue. The control system locks for a pre-determined time period, based on sensor inputs, or until a threshold tension is exceed at which time the lace is released. The lace tension is held during impact (torso trough) in order to support the breast in this more neutral position since it is the most painful time in the gate (running cycle). A typical sports bra produces the greatest breast tissue deflection in a similar portion of the gate. The lace tension is then released just after impact in order to prevent the breast tissue from being thrown upwards by the rigid (high) lace tension. Control systems typically maintain a certain tension on the lace even upon release to continue to provide some level of control of the support structure.

In certain examples, the following triggers can be used for when and how to control the lace tension. Measurements of acceleration of the torso, such as by an accelerometer, can be used to time lace release and retraction. Detection of deflection of the breast tissue relative to the torso using devices such as a strain gauge, a linear potentiometer, or other positional sensors can be used to control lace tension. The devices discussed can also be configured to dampen motion with a dashpot or variable clutch, which can be used to further reduce the impact of the breast tissue at the bottom of the motion cycle.

FIGS. 9A-9D are various drawings illustrating aspects of an air damper analog control system 900, according to an example embodiment. In this example, the air damper can function as an analog control device with lace cable 901 coupled to a support structure of an adaptive support apparel. In this example, the air damper 900 can include structures such as an air cylinder 910, a piston 920, a bias member 930, a housing 940, a check valve 950, and control valve 960. The lace cable 901 couples to the piston 920 through a lace port 916 on the proximal end 914 of the housing 940. The piston 920 is biased towards the distal end 911 of the air cylinder 910 by the bias member 930, in this example a coil spring. Tension on the lace cable 901 presses the piston 920 proximally against both air pression within the air cylinder 910 as well as the bias member 930. The control valve 960 controls the amount of air pressure within the air cylinder 910, while the check valve 950 is a one-way valve that allows air to escape upon retraction of the piston 920.

In this example, the housing 940 includes components such as a cylinder holder 941, an upper housing 942, and a lower housing 944. The upper housing 942 is coupled to the lower housing 944 with housing fasteners 946A, 946B extending through fastener bores 943A, 943B (illustrated in at least FIGS. 9B and 9D). The housing 940 can be affixed to the support apparel via mounting holes 948A, 948B.

Figure 9A:
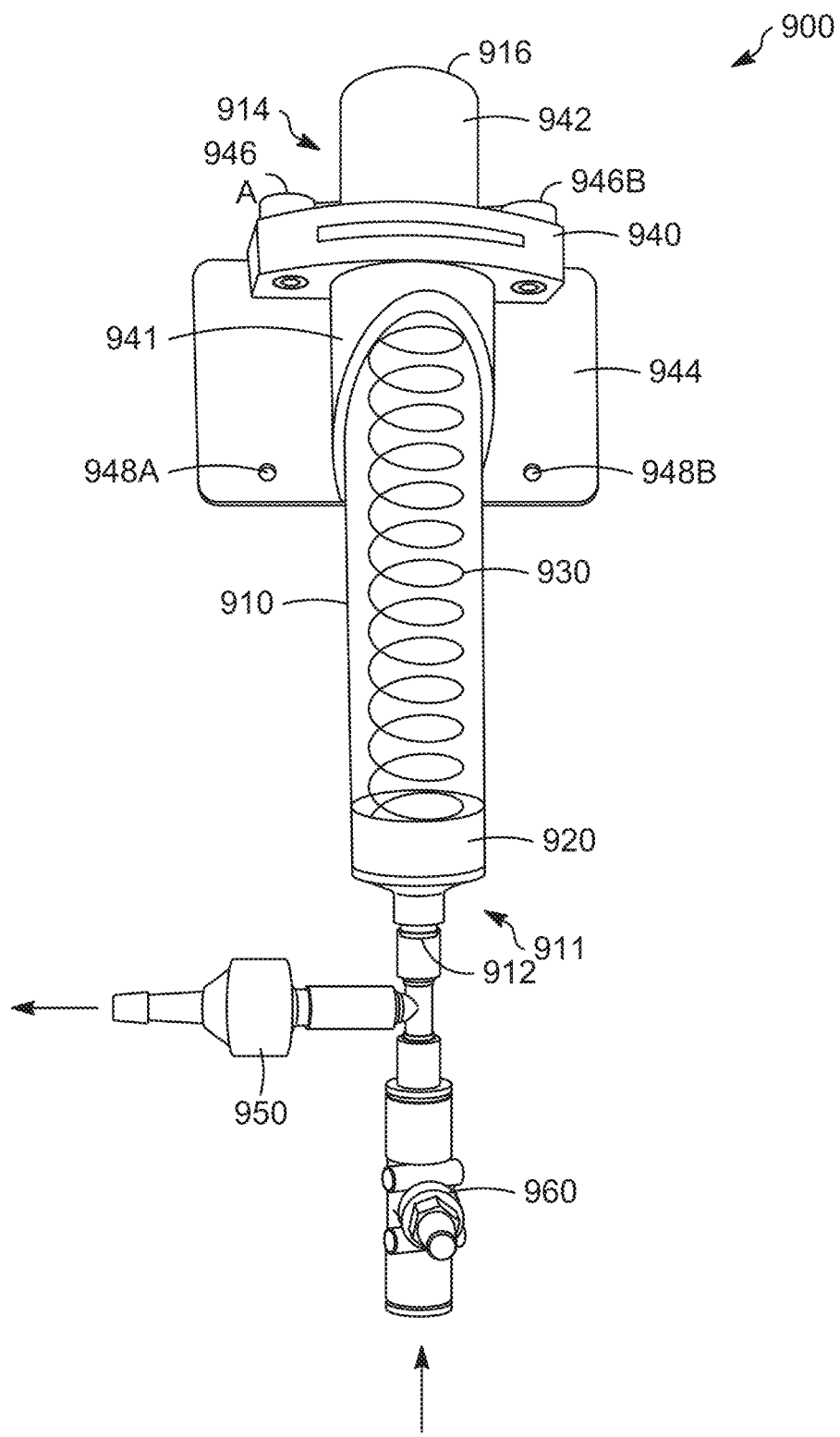
FIGS. 9A-9D are various drawings illustrating aspects of an air damper analog control system, according to an example embodiment.
Figure 9B:
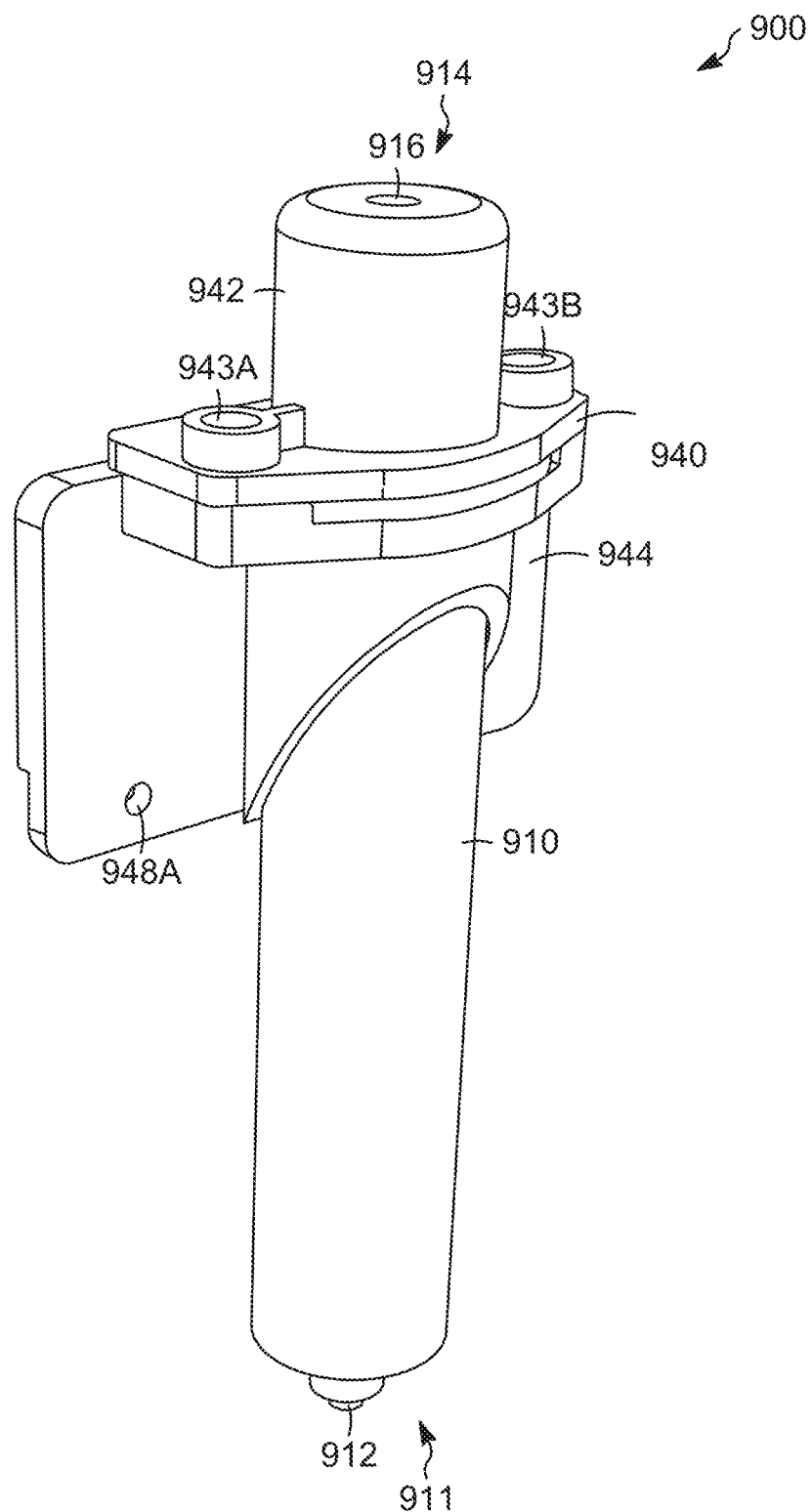
Figure 9C:
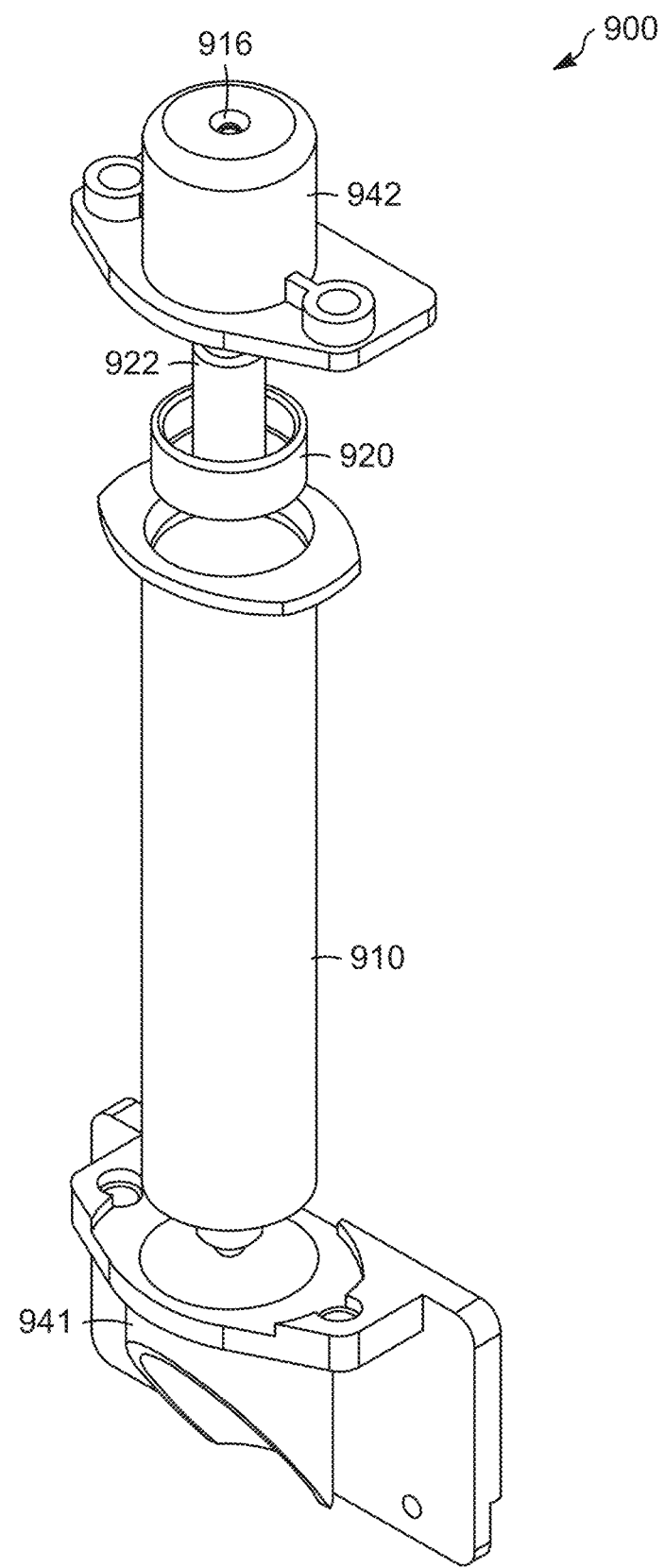
Figure 9D:
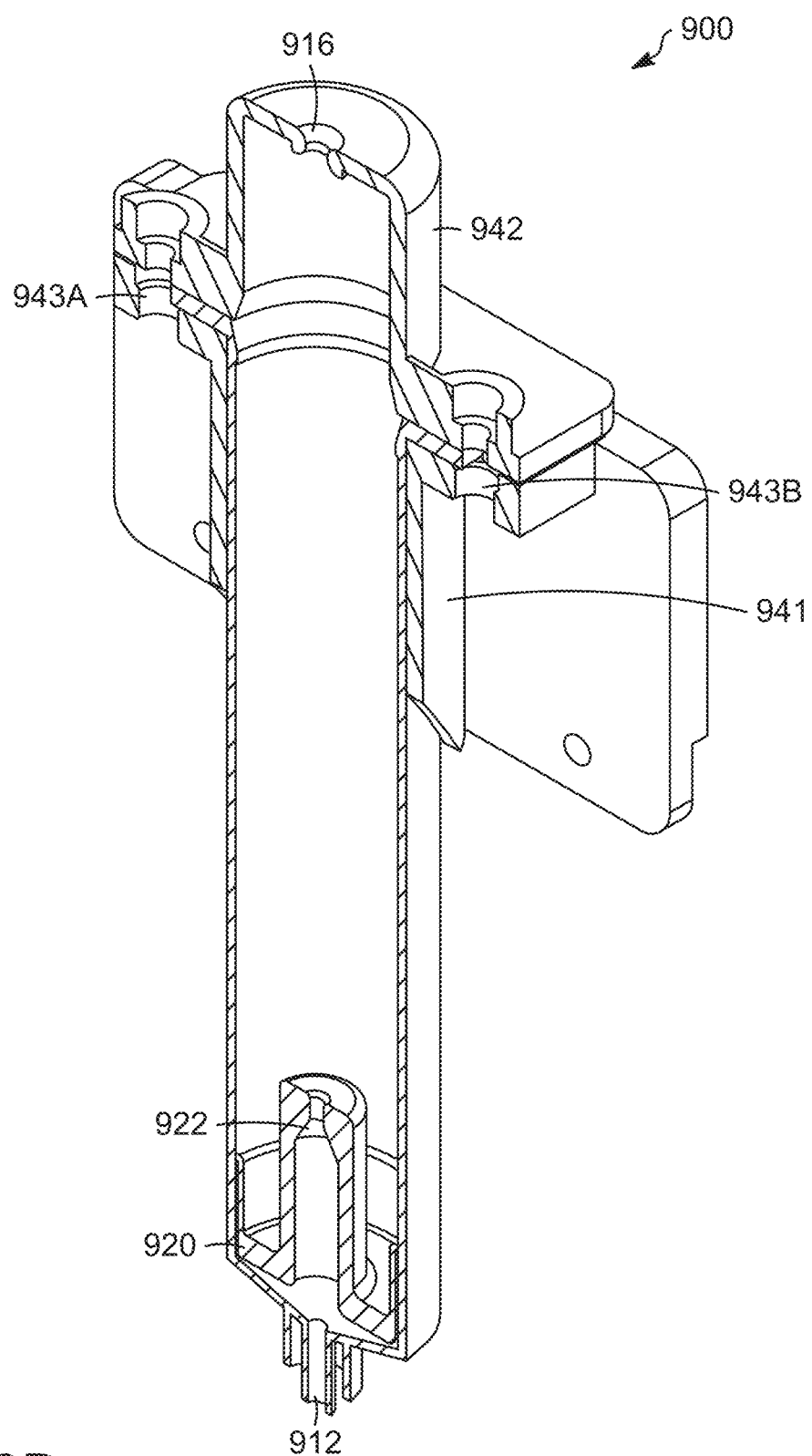

As illustrated in the cross-sectional view in FIG. 9D, the piston 920 includes a lace anchor 922 that captures the lace to provide control. The piston 920 also includes a cylindrical pocket to receive the bias member 930 (illustrated in FIG. 9A). As noted above, in this example the bias member 930 is a helical coil spring, but other suitable bias members could be implemented, such as wave washers. The cross-section also illustrates the damper control port 912 on the distal end 911 of the air cylinder 910. In this example, the control valve 960 and the check valve 950 couple to the damper control port 912. In other examples, the control valve 960 and the check valve 950 can be integrated into the distal end 911 of the air cylinder 910.

As shown in the exploded perspective view in FIG. 9C, the air damper 900 can be assembled by threading the lace 901 through the lace port 916 and affixing the lace 901 to the lace anchor on the piston 920. After affixing the lace 901, the piston 920 is inserted into the proximal end of the air cylinder 910, and the air cylinder 910 is inserted into the cylinder holder 941. Once the air cylinder 910 is in the cylinder holder 941, the upper housing 942 can be coupled to the lower housing 944 using housing fasteners 946A, 946B.

The air damper 900 is illustrated in a cylindrical configuration, but similar air damping concepts can be implemented in other configurations using a controlled air chamber, piston and biasing member.

FIGS. 10A-10I are various drawings illustrating aspects of a power harvesting control system, according to an example embodiment. In this example, the control system 1000 includes a power harvesting component (generator mechanism 1030) that operates to apply tension to the lace during certain portions of its operation cycle. In this example, the power harvesting component is a motor 1032 and reduction gearing 1033 that applies regenerative braking through a series of gears coupled to the lace spool 1010. When engaged the generator mechanism 1030 applies a tension to a lace unwinding from the lace spool 1010 and back drives the motor 1032 to produce power that can be used to operate sensors, lights or other components of an adaptive support system.

In this example, the primary components of the regenerative control system 1000 include a lower housing 1001, an upper housing 1002, a lace spool 1010, a locking ring 1020, a generator mechanism 1030, and a lace guide 1050. The lower housing 1001 includes a mounting flange 1003 within mounting holes 1004. The lower housing 1001 and upper housing 1002 each include a lace guide recess 1005 through which the lace guides 1050 extends. In this example, the upper housing 1002 also includes an opening for a portion of the generator mechanism 1030 (see FIG. 10B).

The lace spool 1010 operates to hold the lace that couples the regenerative control mechanism 1000 to support structures within the adaptive support apparel. The lace spool 1010 operates to control extension and retraction of the lace in a manner intended to control certain targeted soft tissues, such as breast tissue in the adaptive bra example. The lace spool 1010 includes a lace anchor 1011, which is a location for the lace to terminate and be secured to the lace spool 1010. In this example, the lace anchor 1011 includes two adjacent bores extending through a recessed portion of the superior side of the lace spool 1010. The lace spool 1010 includes two circumferential grooves, the first and larger groove is the lace groove 1012, which is where the lace is accumulated upon retraction into the regenerative control mechanism 1000. The second groove formed by a lower portion of the lace spool 1010 and an upper portion of the lace gear 1015 is the lock ring groove 1014, which retains the locking ring 1020. The lower portion of the lace spool 1010 is coupled to the spool gear 1015, which interfaces with the generator mechanism 1030 via the drive gear 1040. The lace spool 1010 and lace gear 1015 rotate on a spool shaft 1017, which is an extension of the lower housing 1001 in this example.

The locking ring 1020 performs a critical function within the regenerative control mechanism 1000 (as well as within all of the similar control mechanisms discussed below) by engaging and disengaging the generator mechanism 1030 via operation of the lock wedge 1025. The locking ring 1020 rotates with the lace spool 1010 based on tension created by the locking tension member 1018 biasing the tension interfaces 1022A, 1022B together and creating increased friction between the locking ring 1020 and the lock ring groove 1014. The locking tension member 1018 can be an O-ring or similar biasing member. The locking ring 1020 also includes an upper lock release tab 1026 and a lower lock release tab 1027, which operate to release friction between the locking ring 1020 and the lock ring groove 1014 at certain points in the rotation of the lock ring 1020 by reducing the tension on the tension interfaces 1022A, 1022B and expanding the locking ring 1020 diameter. The upper lock release tab 1026 and lower lock release tab 1027 engage features on the lower housing 1001 or upper housing 1002 to release tension on the lock ring 1020. In some examples, the upper lock release tab 1026 can ride within a slot in the upper housing and operate by engaging end points on the slot. Alternatively, the upper lock release tab 1026 can engage a lock release housing tab extending from the underside of the upper housing. In some examples, the lower lock release tab 1027 can engage a lock release housing tab extending up from the inside surface of the lower housing. These different configurations are illustrated below in various figures.

Figure 10A:
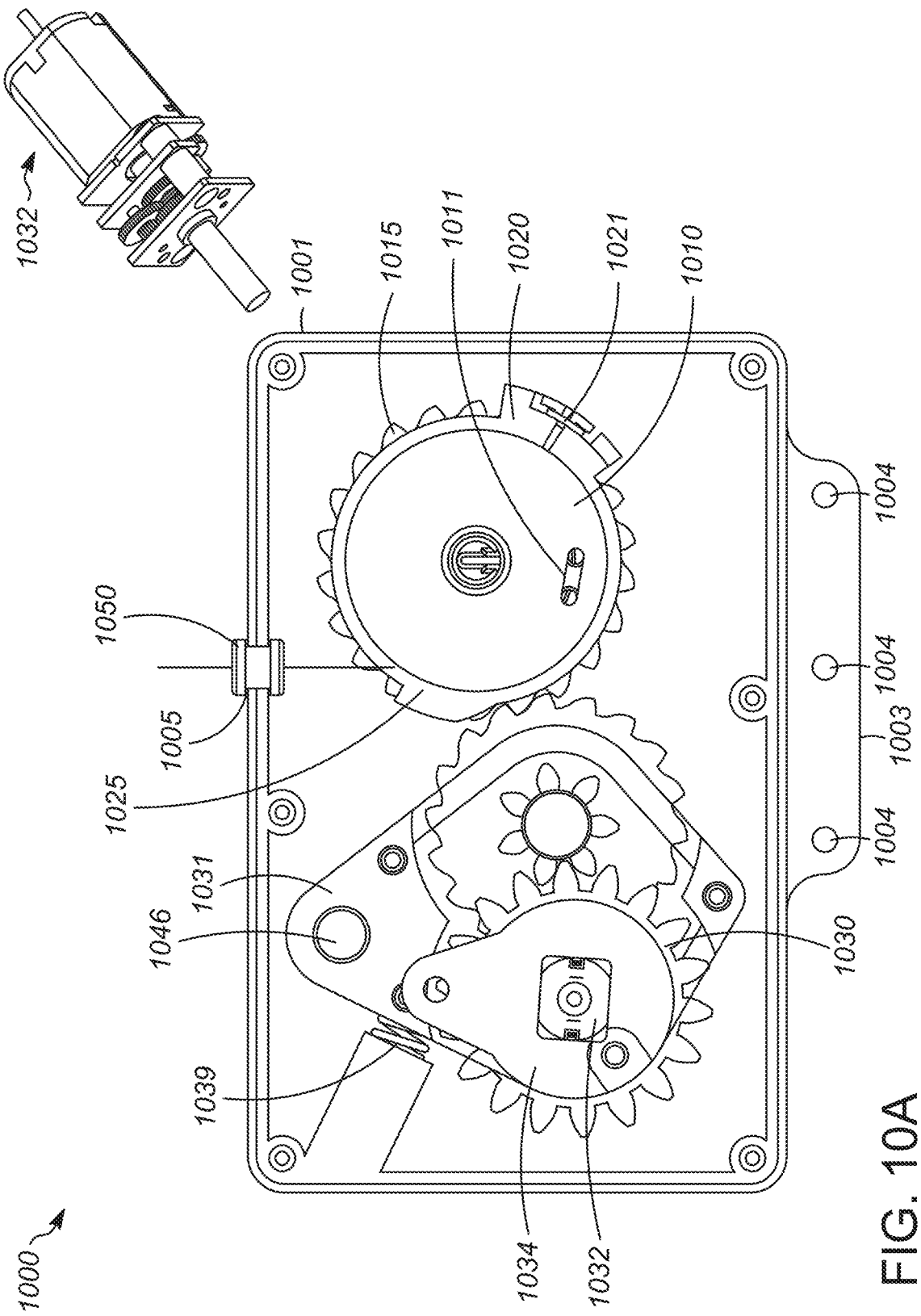
FIGS. 10A-10I are various drawings illustrating aspects of a power harvesting control system, according to an example embodiment.
Figure 10B:
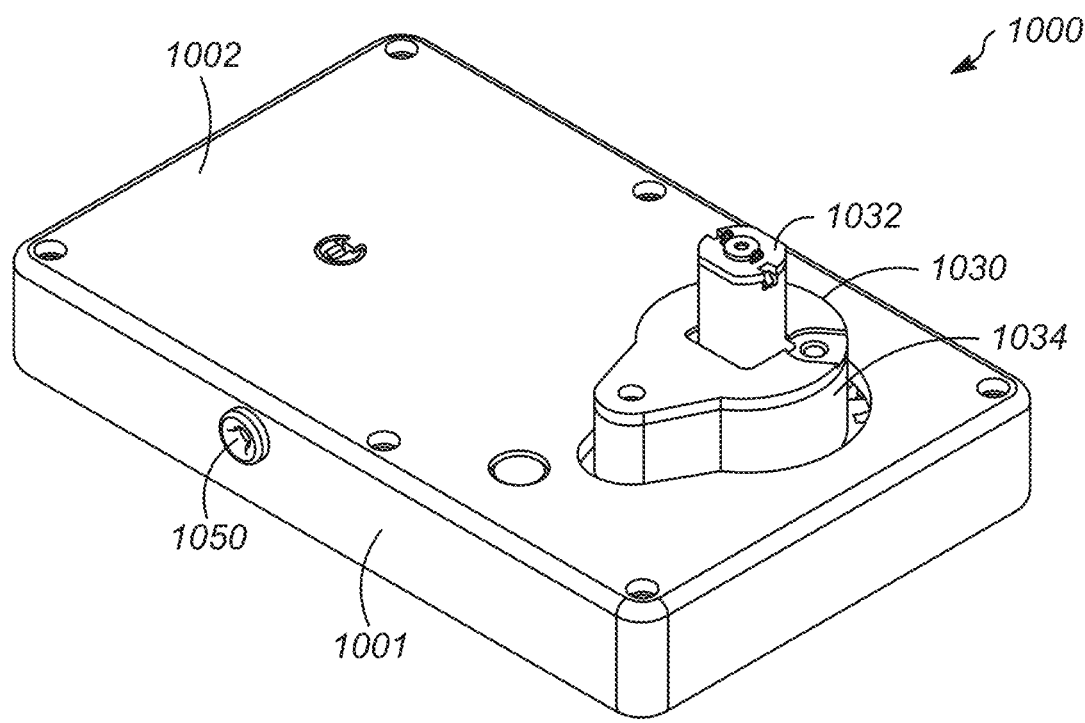
Figure 10C:
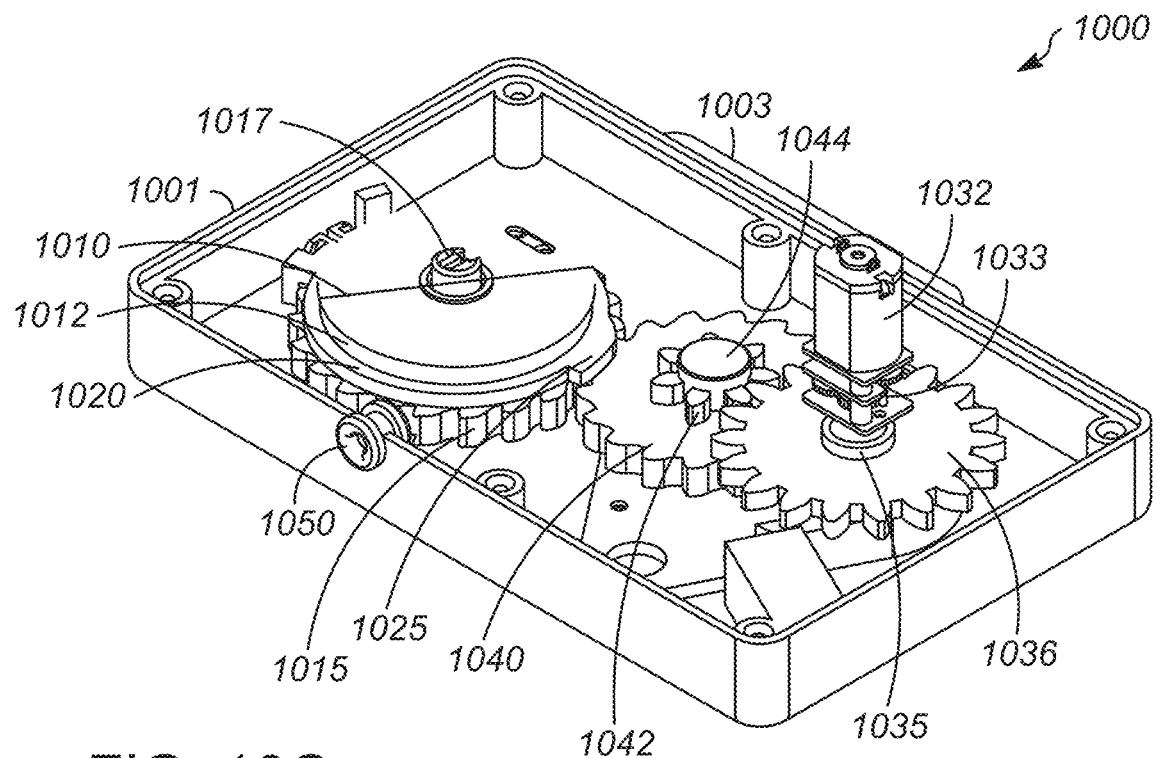
Figure 10D:
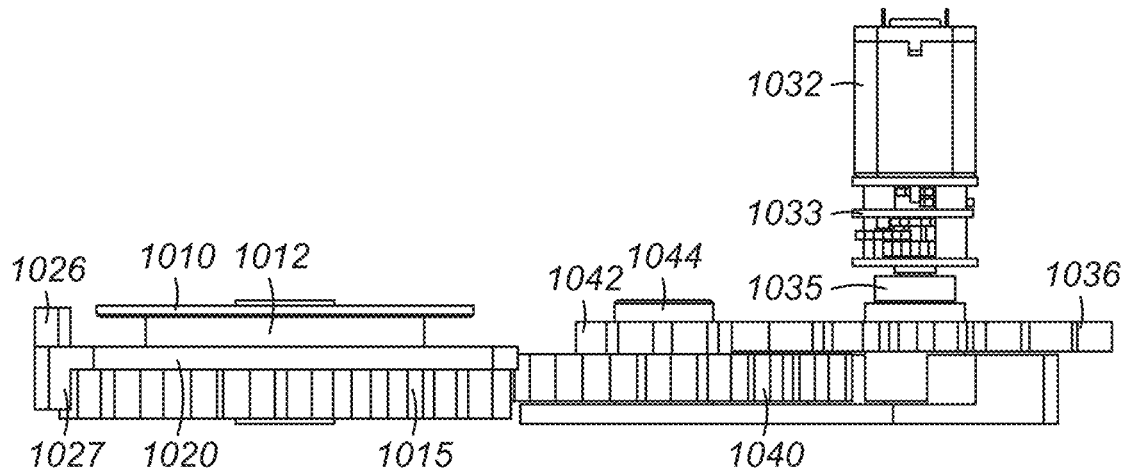
Figure 10E:
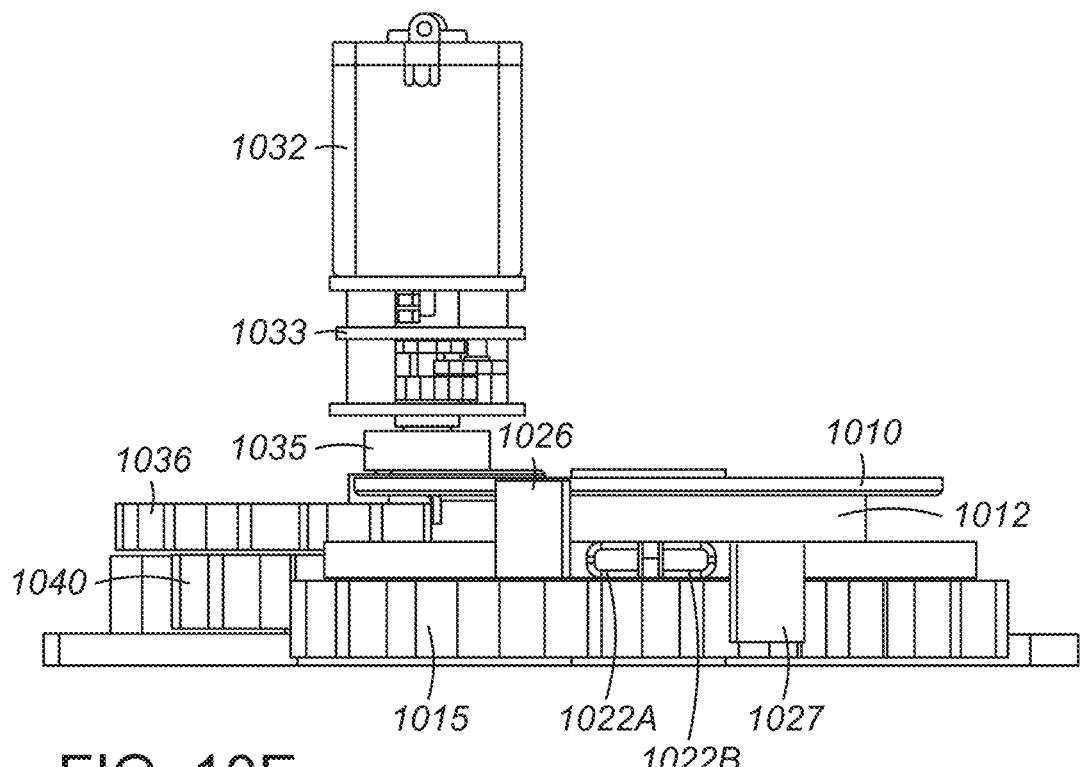
Figure 10F:
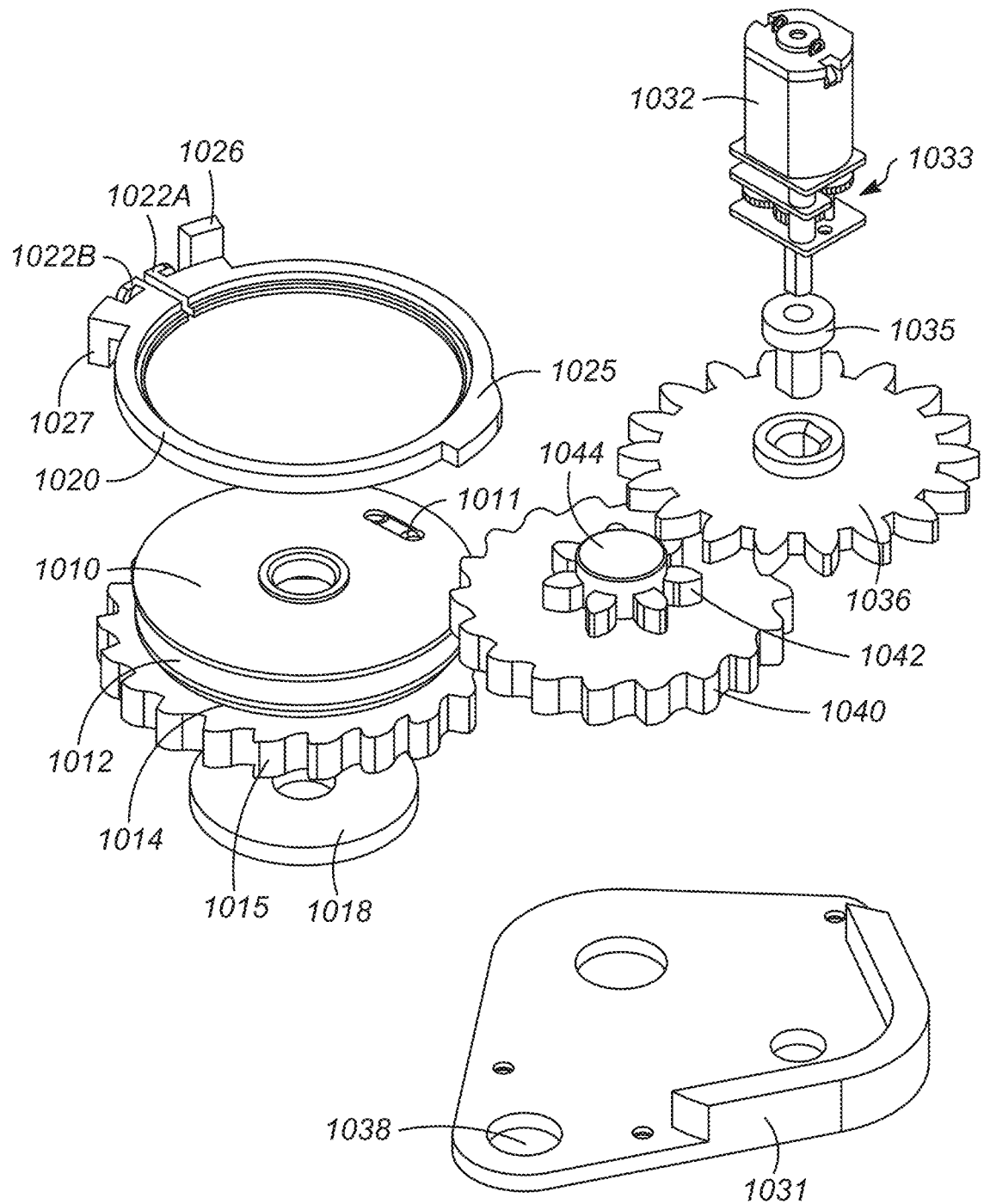
Figure 10G:
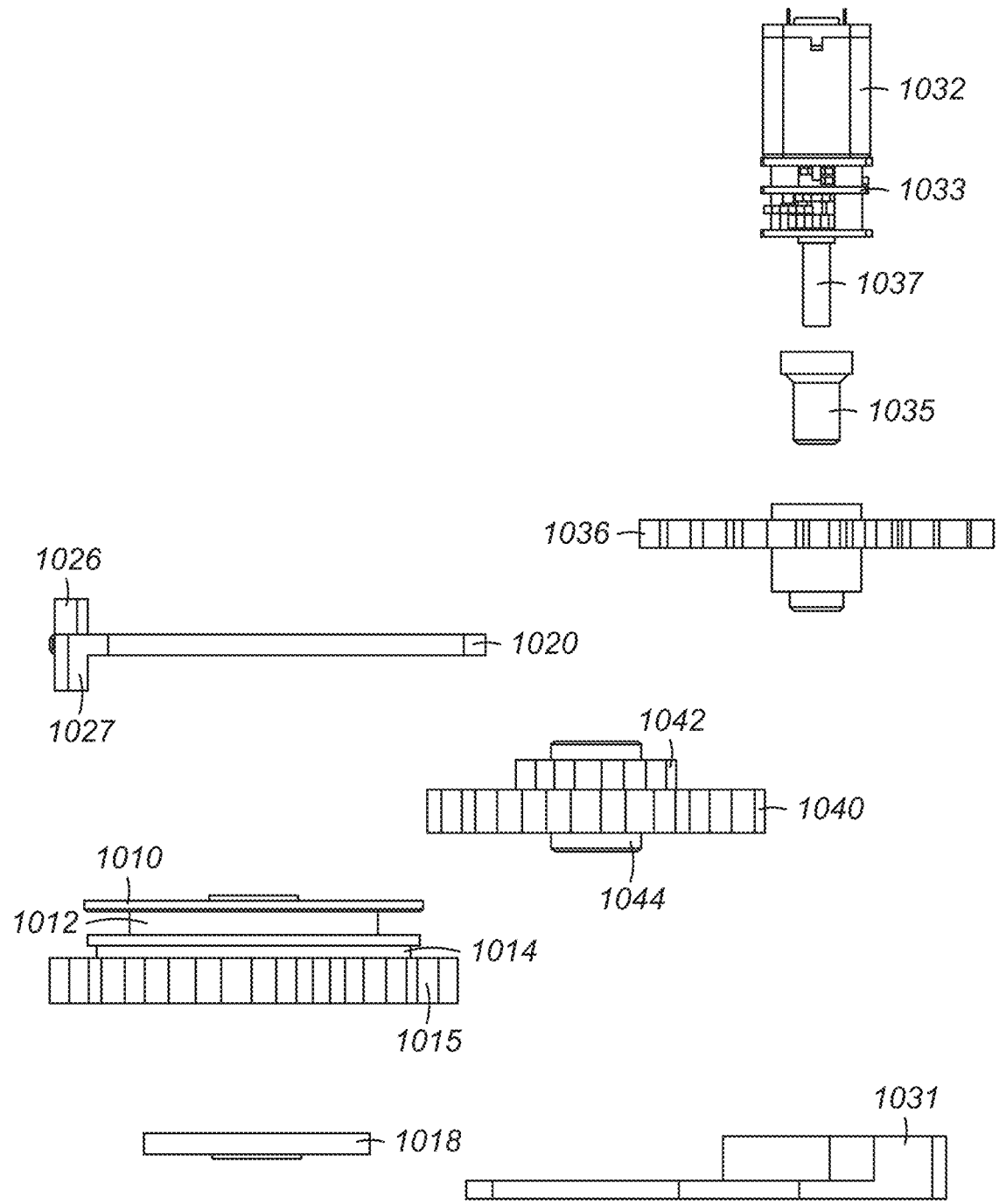
Figure 10H:
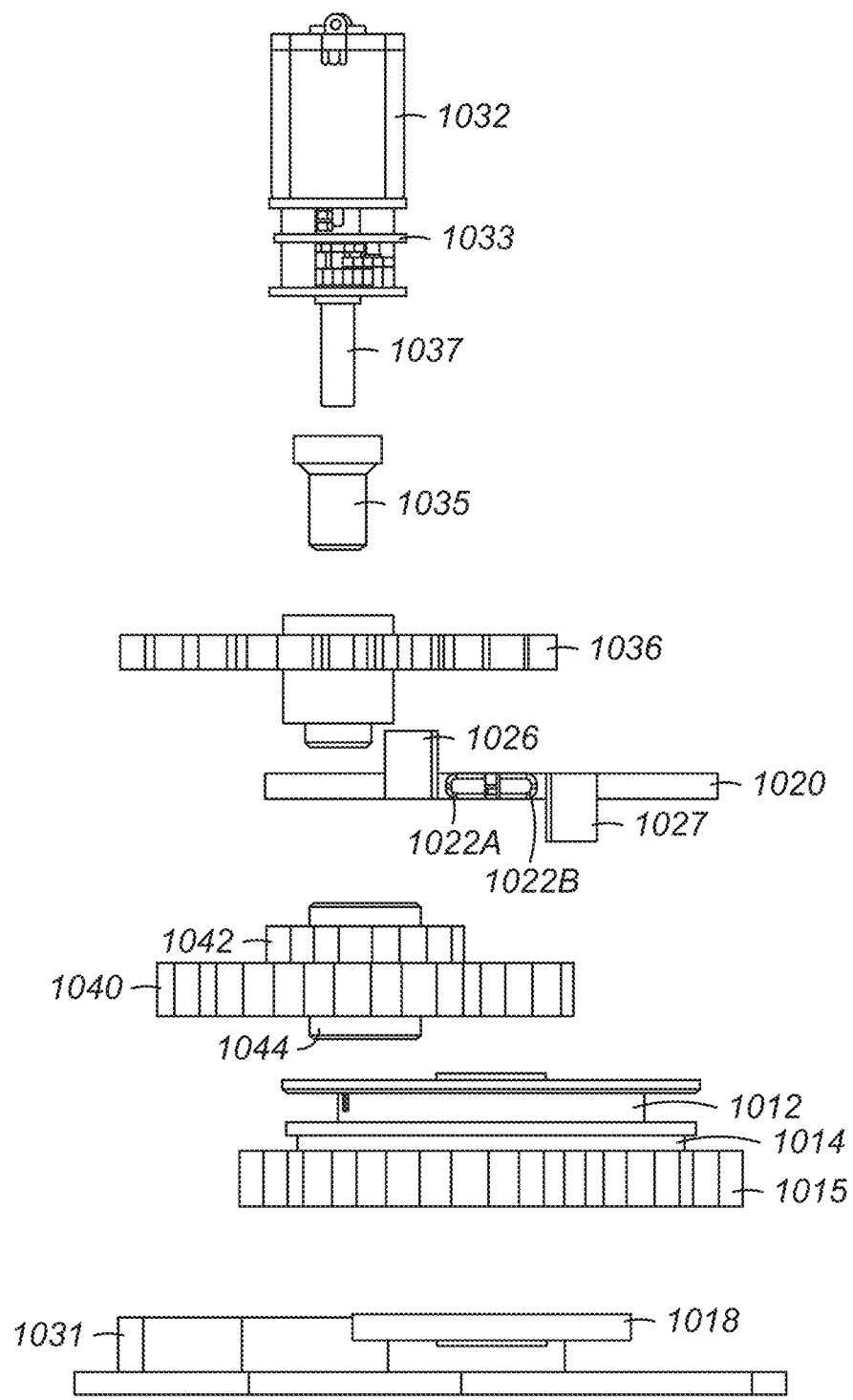
Figure 10I:
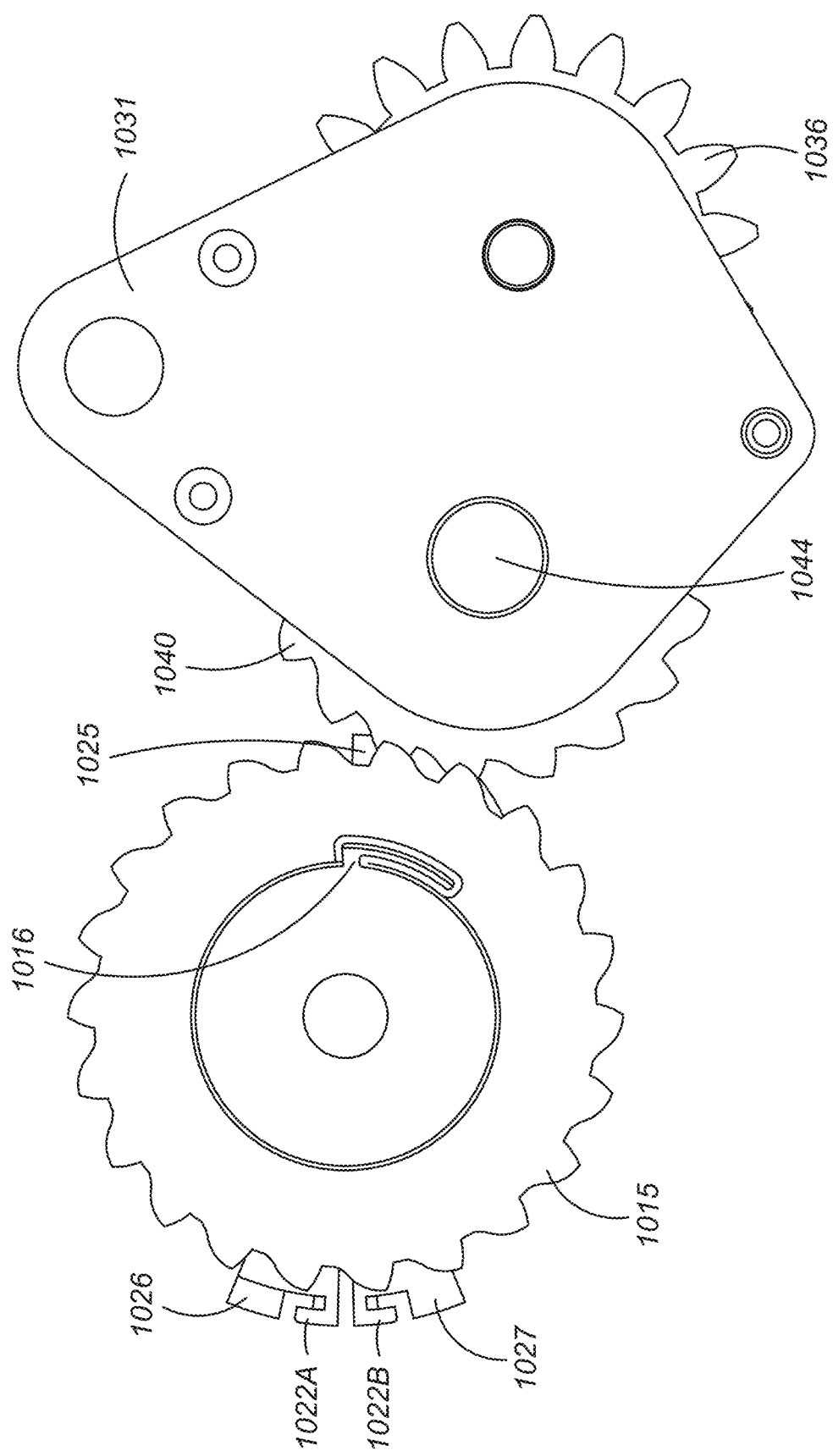
Figure 11A:
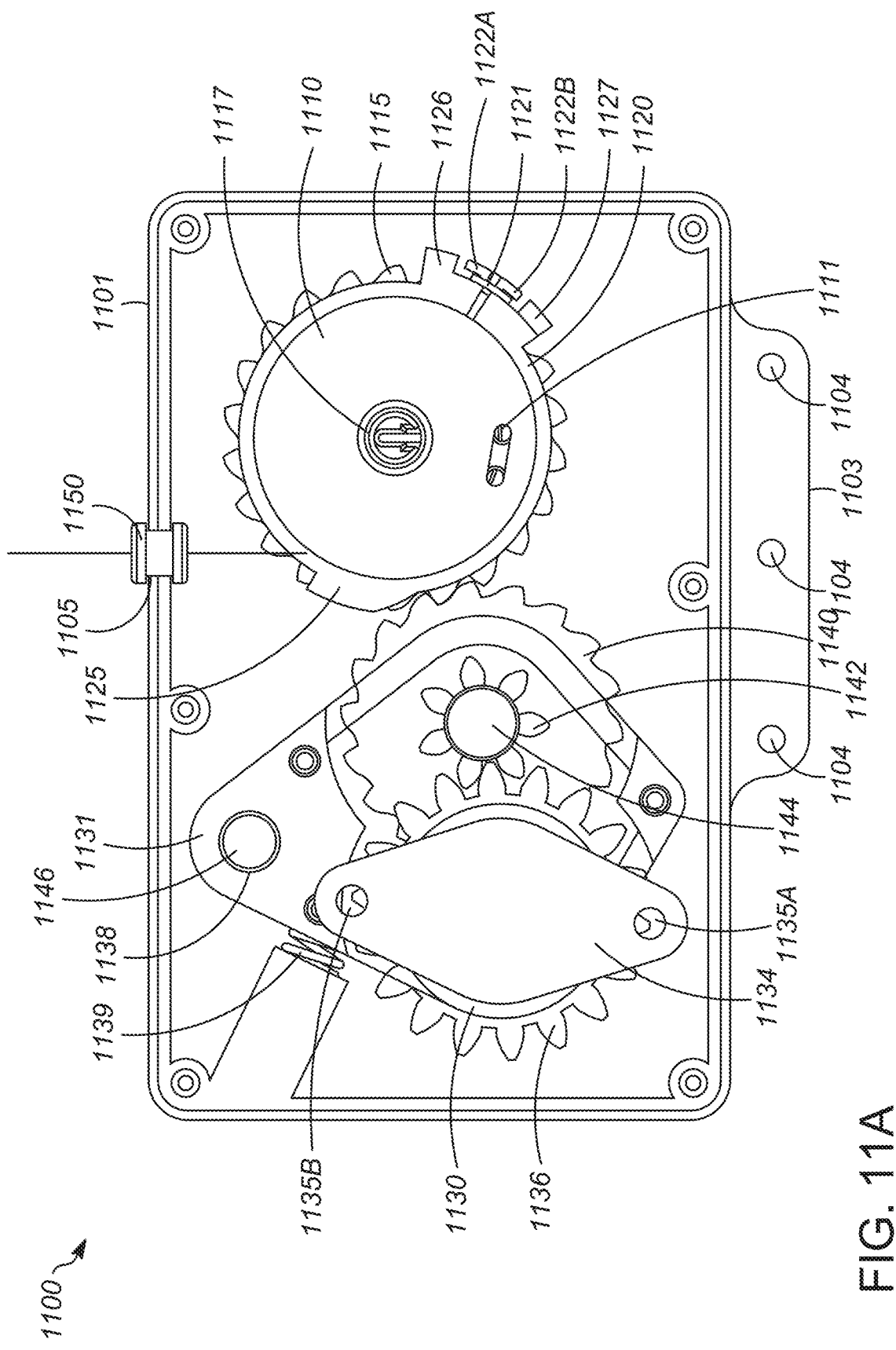
FIGS. 11A-11J are various drawings illustrating aspects of a rotary damper analog control system, according to an example embodiment.
Figure 11B:
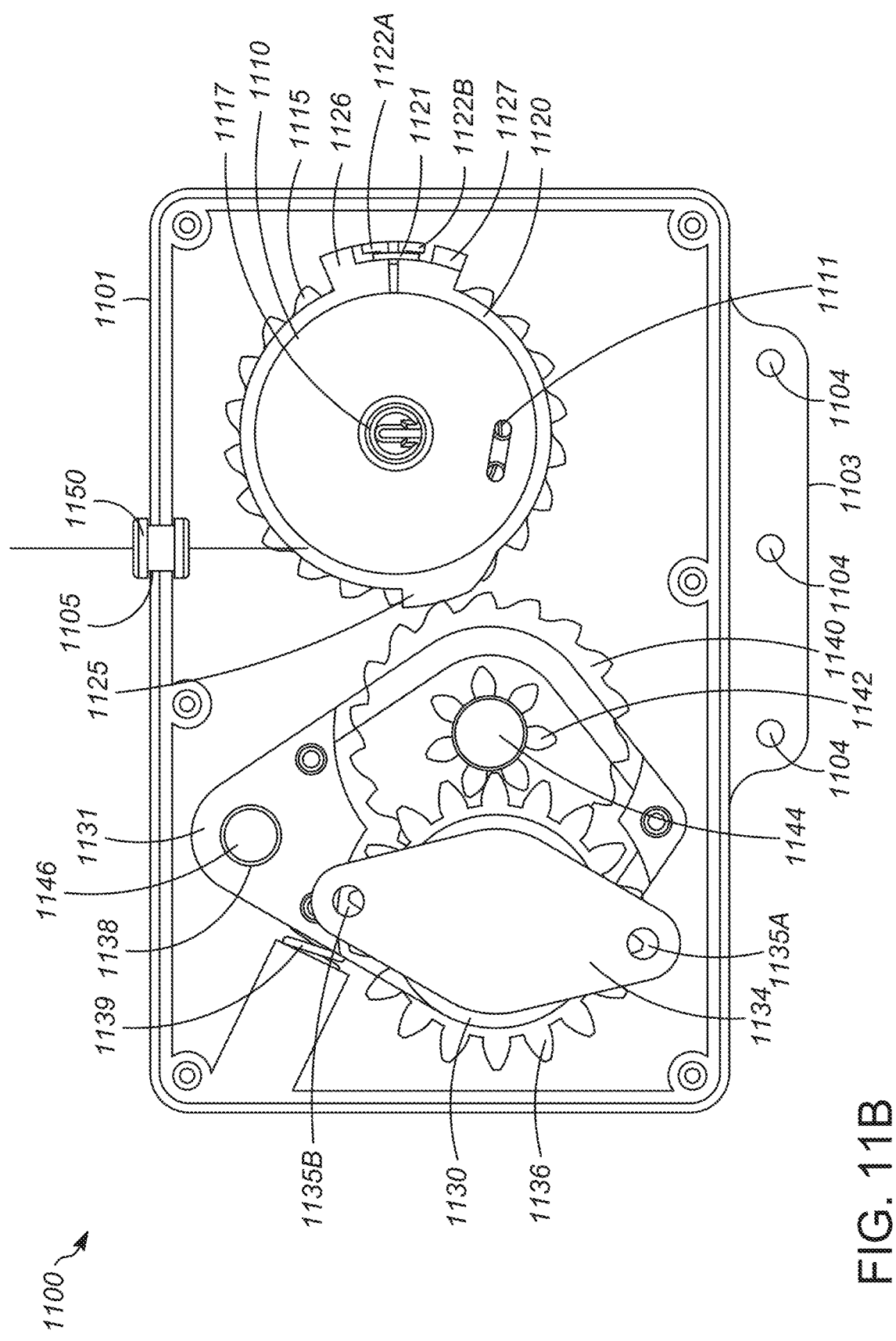
Figure 11C:
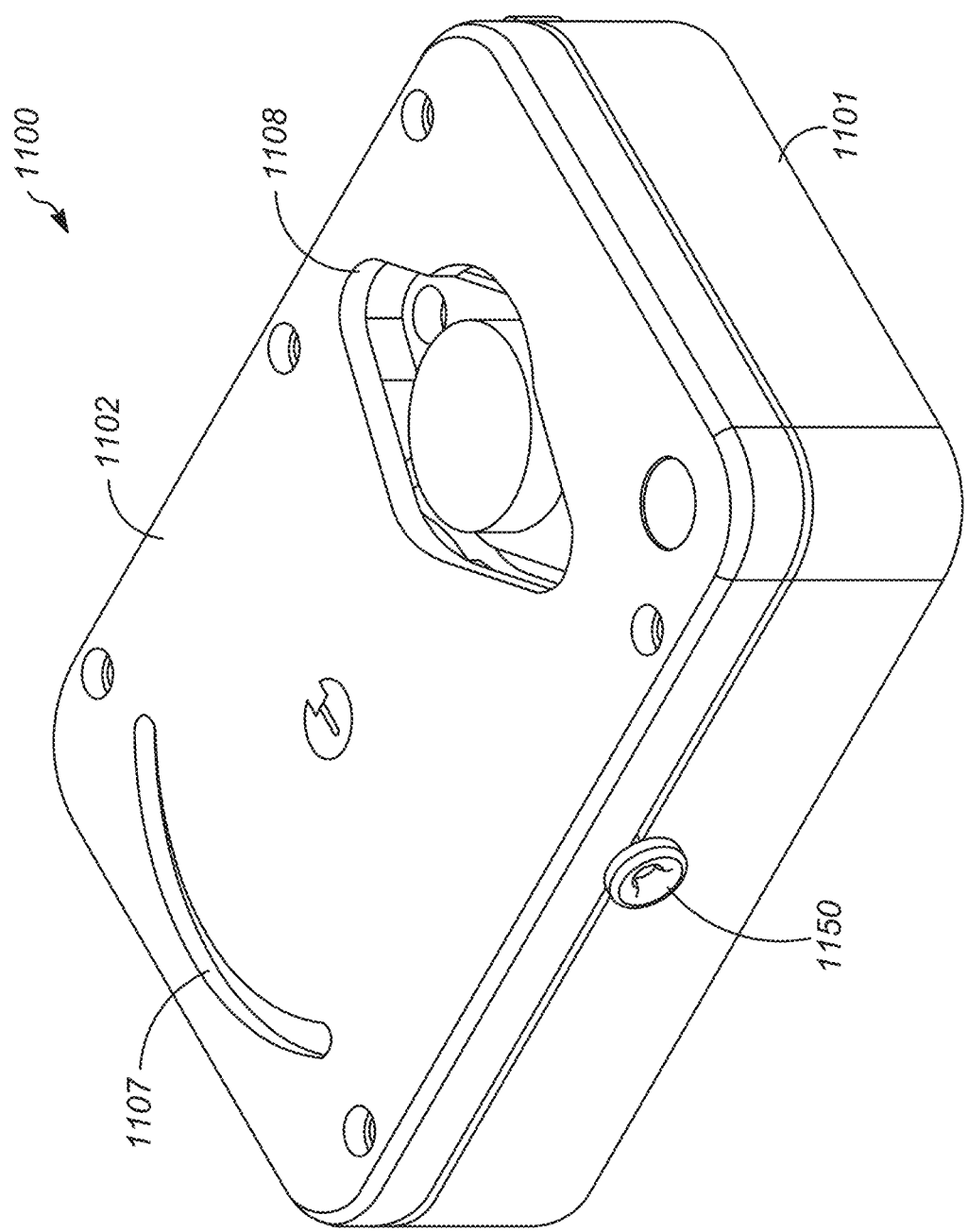
Figure 11D:
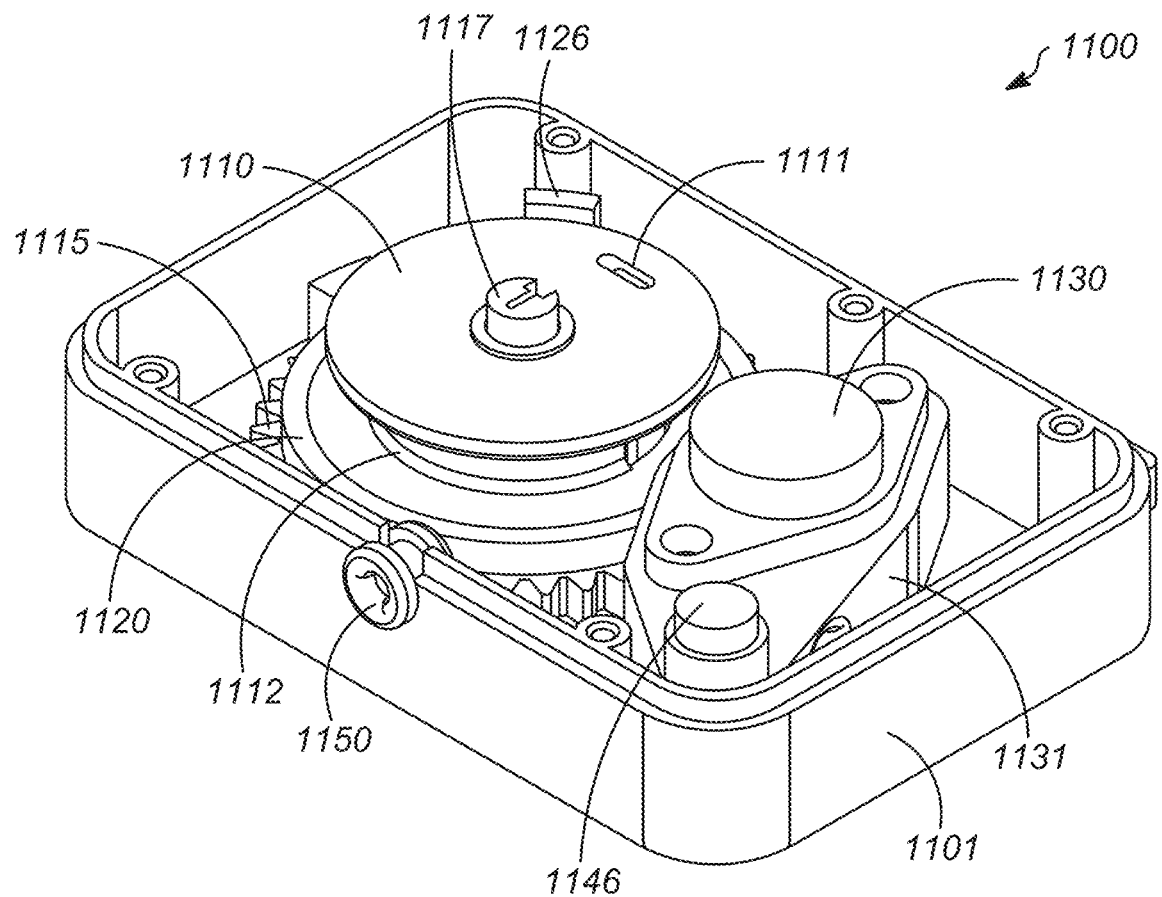

Overall operation of the lock ring 1020 is best illustrated by FIGS. 11A and 11B, which include a comparable lock ring 1120 with similar structures and operation as are included in the regenerative control mechanism 1000. As shown in FIG. 11A, the lock ring 1120 is in an unlocked state where the lock wedge 1125 is disengaged from the drive gear 1140, which allows the damper mechanism 1130 (comparable to generator mechanism 1030) to be engaged via interaction between the drive gear 1140 and spool gear 1115 (comparable to spool gear 1015). The unlocked state illustrated in FIG. 11A can also be considered a damping state (or generating state in the example of FIGS. 10A-10I). The lock ring 1120 is rotated into the unlocked state upon extension (e.g., unwinding) of the lace from the lace spool 1120. In this state, the lower lock release tab 1127 can engage a lock release housing tab 1106 to release the friction between the lock ring 1120 and the lock ring groove 1114 of the lace spool 1110 (stretching the locking tension member 1121 and opening the diameter of the lock ring 1120).

Upon retraction of the lace back onto the lace spool 1110, the lock ring 1120 will rotate in a counter-clockwise direction into a locked state as illustrated in FIG. 11B. The locked state illustrated in FIG. 11B is also known as the retracting state or mode, where the lace is retracted back onto the lace spool 1110 through operation of a rotary bias member 1118 within the lace spool 1110. In the retracting mode, the lock ring 1120 is rotated such that the lock wedge 1125 disengages the damping mechanism 1130 (disengaging the drive gear 1140 from the spool gear 1115). In the retracting mode, the upper lock release tab 1126 engages a lock release housing slot 1107 (or lock release housing tab extending inferiorly from the underside of the upper housing 1102 in some examples) to release tension on the lock ring 1120 and allow the lace spool 1110 to rotate more freely. The operating principals of the locking ring 1120 discussed in view of FIGS. 11A and 11B apply similarly to all of the control mechanisms in FIGS. 10A through 13I, with some variations as noted below for the locking ring in FIGS. 12A-12I.

Back to the discussion of specifics of the generator control mechanism 1000, the generator mechanism 1030 can include a pivoting mounting plate 1031, a motor 1032, reduction gearing 1033, a generator housing 1034, a generator gear 1036, a drive gear 1040, and a pinion gear 1042. The motor 1032 is directly coupled to the reduction gearing 1033 which includes a motor shaft 1037 extending into a generator gear coupler 1035. The motor 1032 and reduction gearing 1033 are driven through rotation of the generator gear 1036, which is driven by the drive pinion 1042 coupled to the drive shaft 1044 of the drive gear 1040. The drive gear 1040 engages with the spool gear 1015 (as discussed above in reference to the locking ring 1020), which controls rotation of the lace spool 1010. The entire generation mechanism 1030 pivots on the pivoting mounting plate 1031 and is biased against the spool gear 1015 via the generator bias member 1039. In this example, the generator bias member 1039 is a coil spring, but the coil spring could be replaced by any comparable bias member. Pivoting of the generation mechanism 1030 engages disengagement of the generation mechanism under certain operating conditions. The generation mechanism 1030 pivots around pivot point 1038 that corresponds with the pivot shaft 1046 that extends through a portion of the pivoting mounting plate 1031.

FIG. 10I is a bottom view illustration of a portion of the internal mechanism within the regenerative control system 1000. In this example, the lace spool 1010 includes a bias member interface 1016 where the rotary bias member 1018 is secured to the lace spool 1010 and lace gear 1015. In this example, a portion of a rotary (torsional) spring extends into a slot in the side of an inner recess of the lace spool 1010 that holds the rotary bias member 1018.

Many of the components discussed above are replicated in the following control systems. Accordingly, the discussion of those components provided above apply similarly to the similar components introduced below. The following discussion will focus on differences in the various control systems, such as the tension mechanism (e.g., regenerative braking, analog damper, ratchet system, and rotary friction mechanism). Individual components will be introduced as discussed at least briefly within each embodiment.

FIGS. 11A-11J are various drawings illustrating aspects of a rotary damper analog control system, according to an example embodiment. In this example, the control system uses a rotary damper to impart extra tension on the lace. The rotary damper control system 1100 can include a lower housing 1101, an upper housing 1102, a lace spool 1110, a spool gear 1115, a locking ring 1120, a damper mechanism 1130, a drive gear 1140, and a lace guide 1150. The housing includes the lower housing 1101 coupled to the upper housing 1102 with the lower housing 1101 including a mounting flange 1103 with mounting holes 1104. Similar to other embodiments, the housing also includes a lace guide recess 1105. In this example, the housing also includes a lock release housing tab 1106, a lock release housing slot 1107, and a damper housing opening 1108.

Figure 11E:
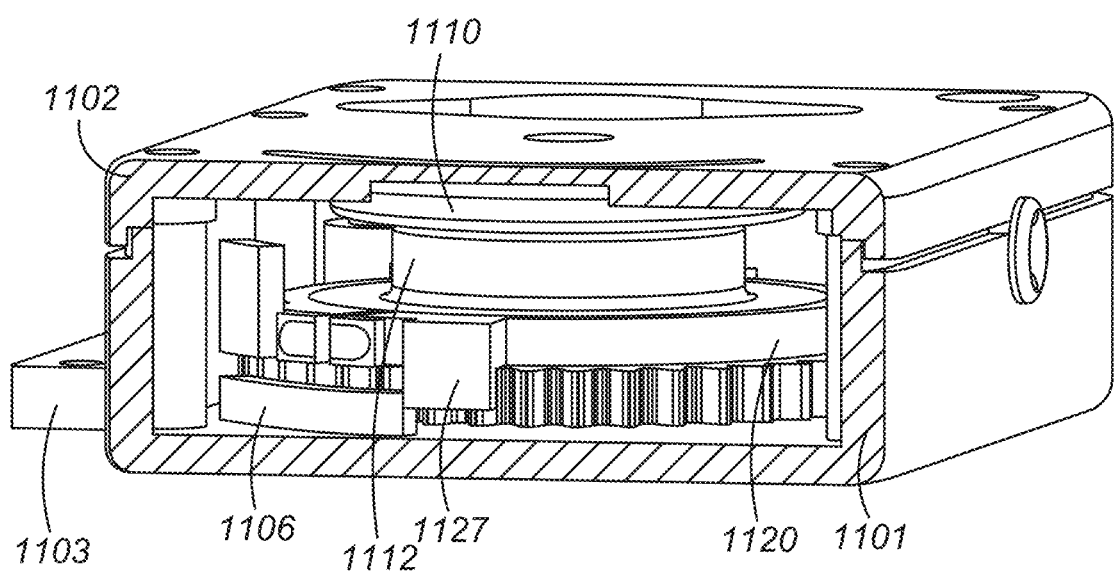
Figure 11F:
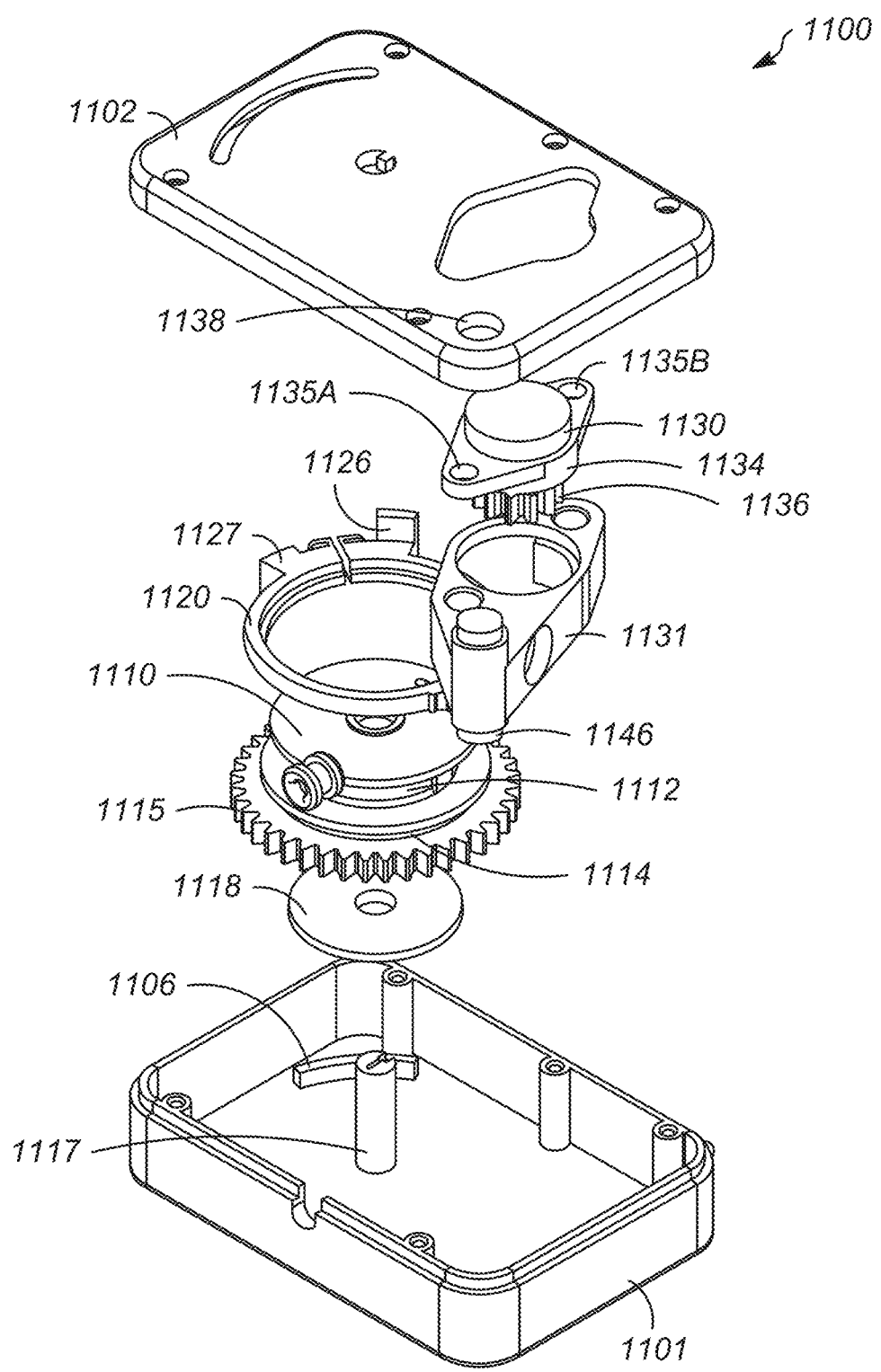
Figure 11G:
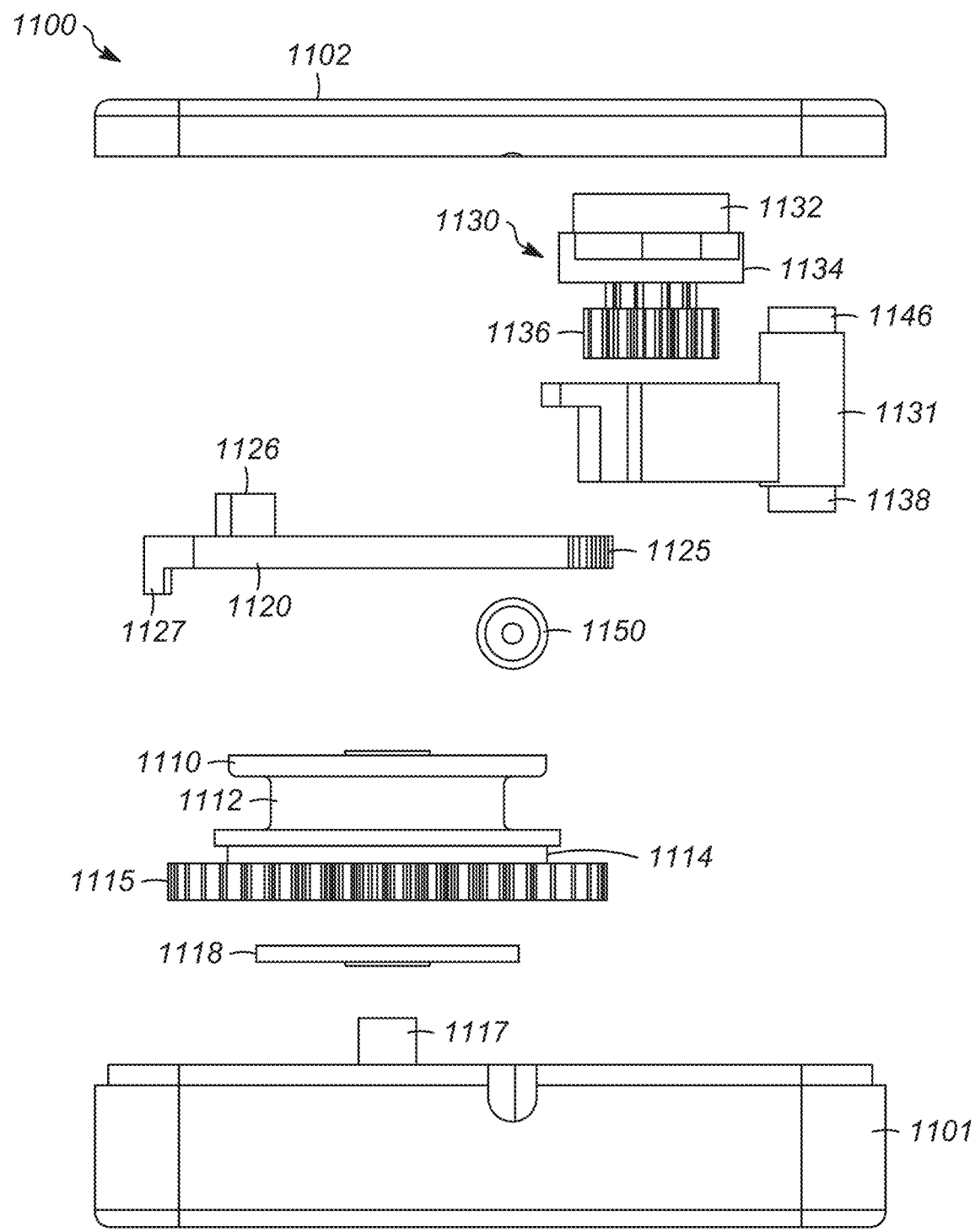
Figure 11H:
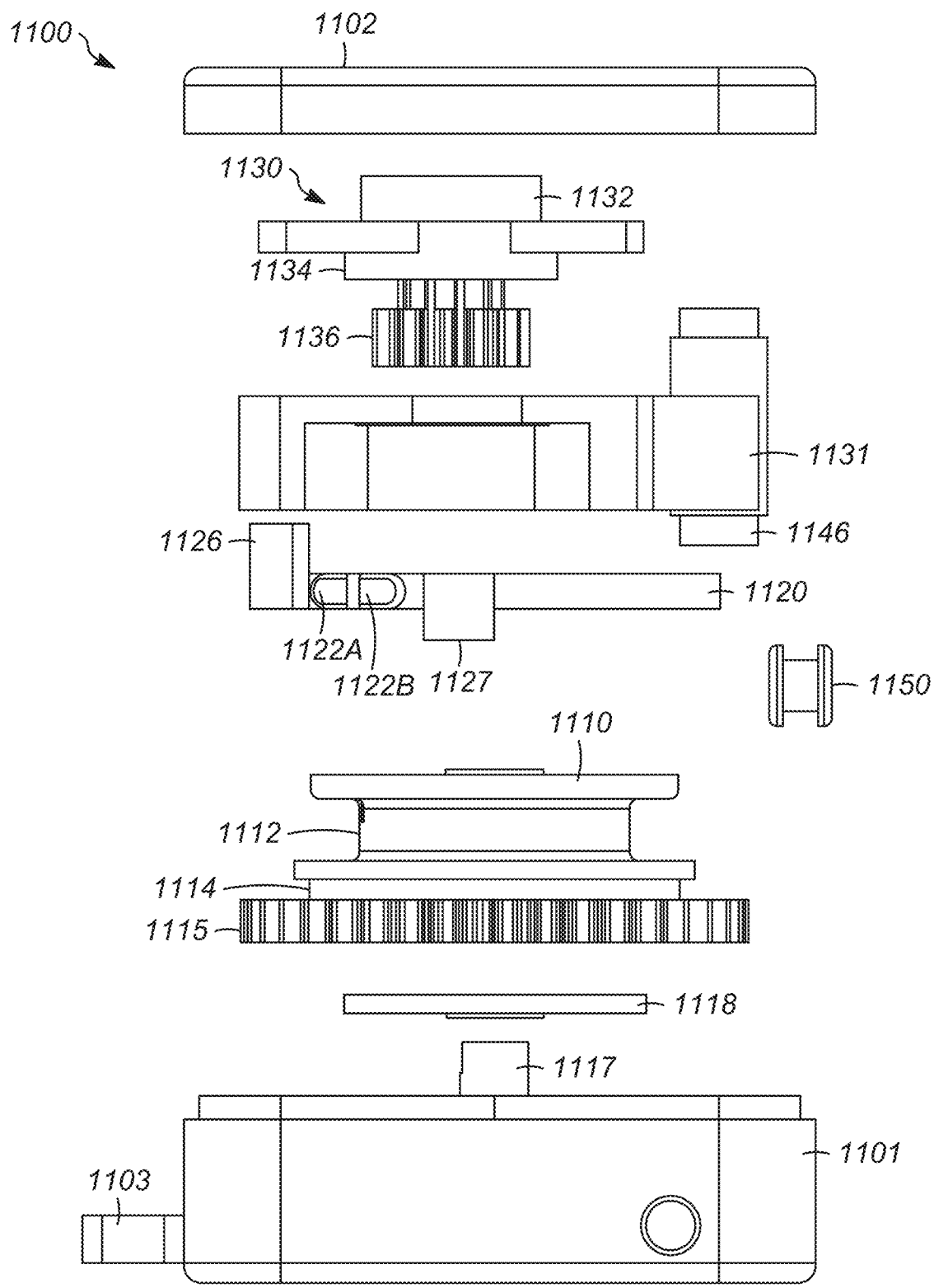
Figure 11I:
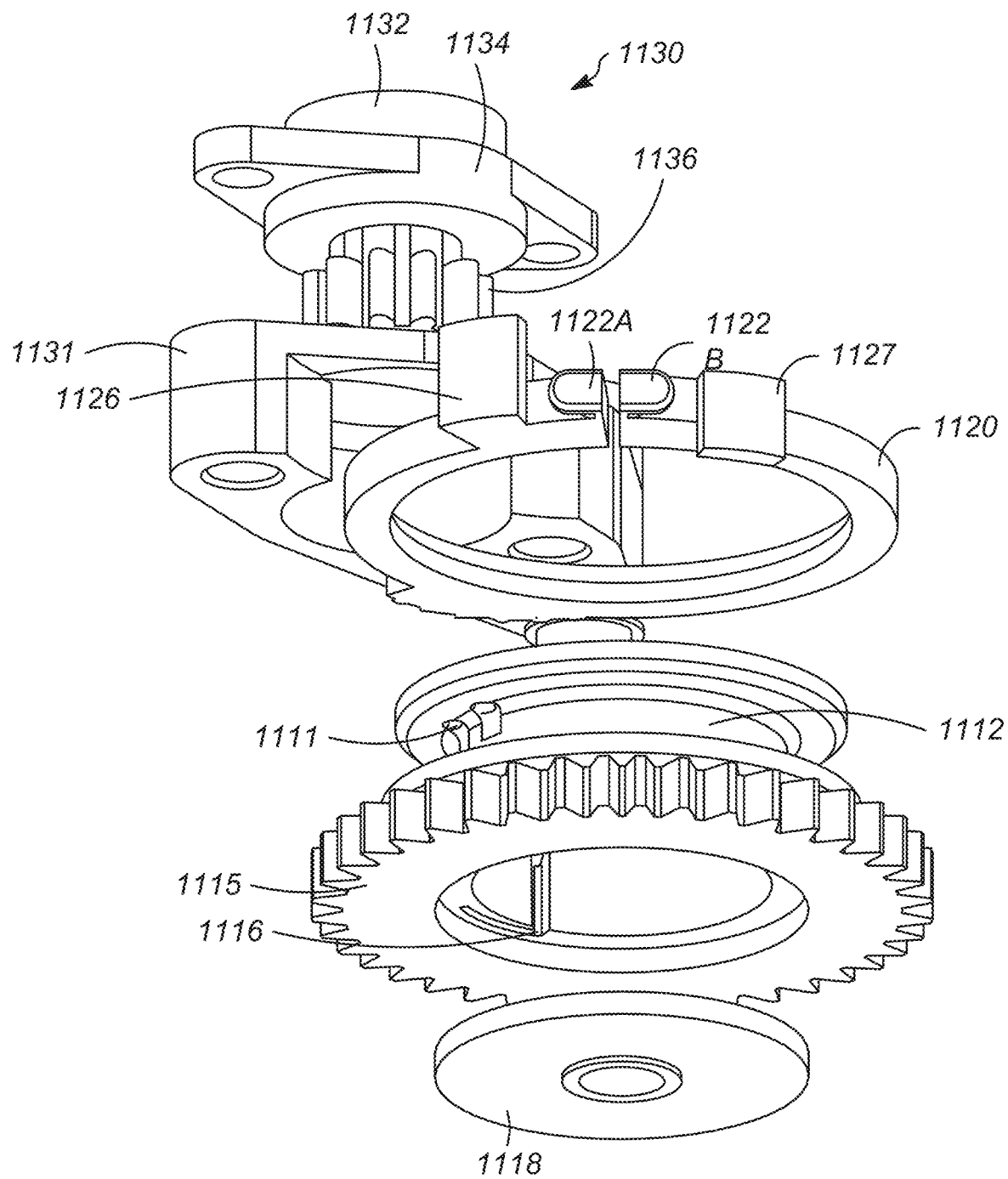
Figure 11J:
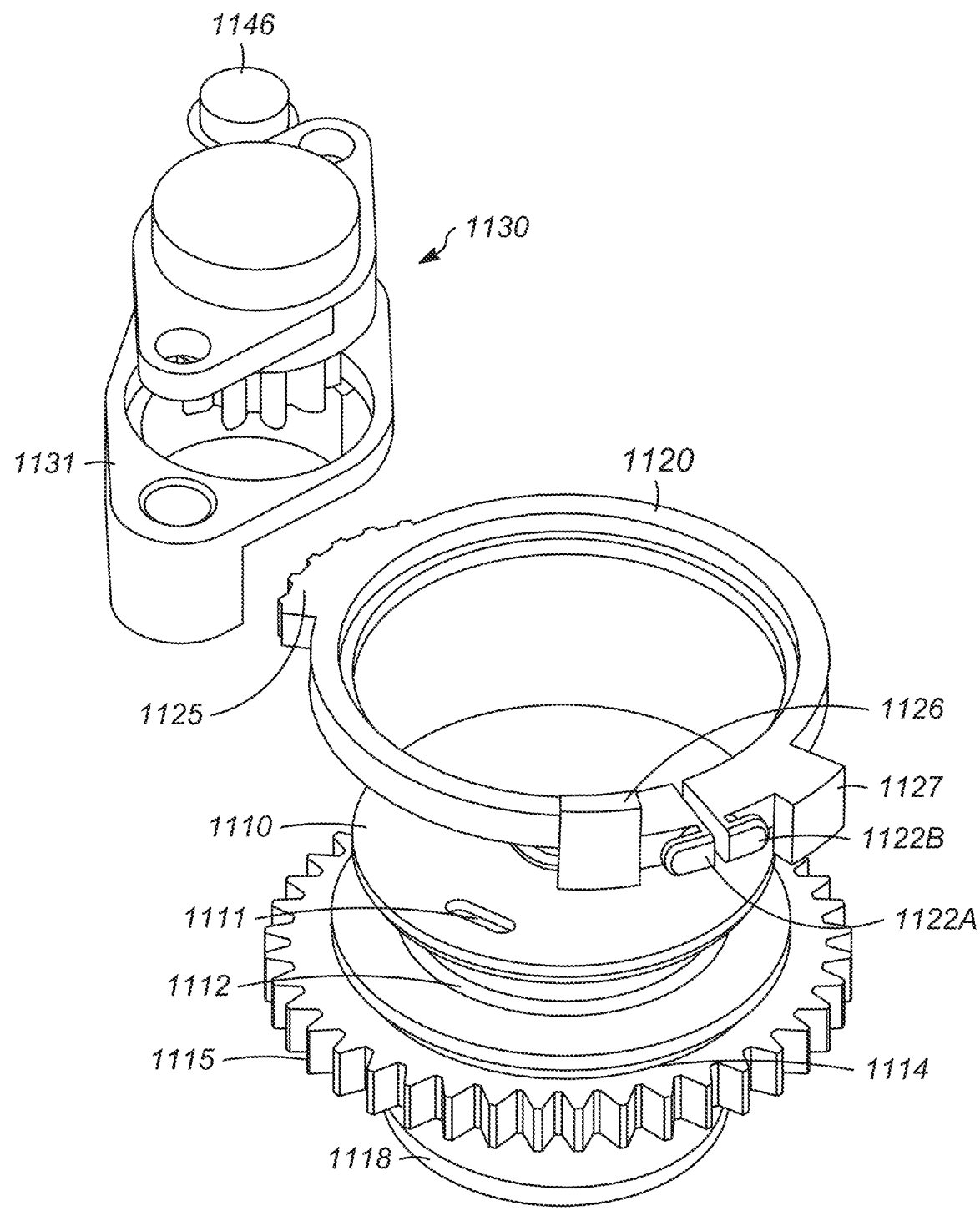

In this example, the lace spool 1110 includes a lace anchor 1111, a lace groove 1112, a lock ring groove 1114, a bias member interface 1116 and is coupled to a spool gear 1115. The lace spool 1110 also houses a rotary bias member 1118 that couples to the lace spool 1110 via the bias member interface 1116. As with the other embodiments, the locking ring 1120 fits into the lock ring groove 1114 on the lace spool 1110. Operation of the lace spool 1110 and locking ring 1120 are discussed above in reference to FIGS. 11A and 11B. FIG. 11E is a cross-section perspective view illustrating how the lower lock release tab 1127 on the locking ring 1120 engages with a lock release housing tab 1106. As the locking ring 1120 rotates clockwise (engaging damping mode—unlocked mode) the lower lock release tab 1127 engages the end of the lock release housing tab 1106 to release tension on the locking ring 1120. The upper lock release tab 1126 can engage a similar structure (or a housing slot) to release tension on the locking ring 1120 in the retracting mode.

The damper mechanism 1130 is introduced in FIG. 11A, and further detailed in FIGS. 11F-11J (in particular). In this example, the damper mechanism 1130 can include components such as a pivoting damper mount 1131, a damper housing 1134, a damper 1132, damper mounting holes 1135A, 1135B, and a damper gear 1136. The damper 1132 can be mounted on the pivoting damper mount 1131, which pivots about the damper pivot point 1138 on the pivot shaft 1146 extending from the pivoting damper mount 1131. As illustrated in FIGS. 11A-11B, the pivoting damper mount 1131 is biased by the damper bias member 1139. The example illustrated in FIGS. 11A-11B includes a drive gear 1140, a drive pinion 1142 that interfaces with the damper gear 1136, and a drive shaft 1144. However, the example illustrated in FIGS. 11C-11J has the damper gear 1136 directly interfacing with the spool gear 1115.

The damper mechanism 1130 in these examples operates to increase the drag on the extension of the lace by adding mechanical resistance to the rotation of the lace spool 1115 when the locking ring 1120 is rotated such that the lock wedge 1125 is not engaged with the damper gear 1136 (or drive gear 1140), so the damper gear 1136 can engage with the spool gear 1115. The damping mechanism 1131 is illustrated in the damping mode in FIG. 11A. As shown in FIG. 11B, the damping mechanism 1130 is disengaged during the retraction mode of operation, where the rotary bias member 1118 drives the lace spool 1115 to retract the lace back onto the lace spool 1115. In certain examples, the damper 1132 can be an adjustable analog damping device with a rotary (or similar) input that allows for adjustment of the amount of damping generated by the damping mechanism 1130.

FIGS. 12A-12I are various drawings illustrating aspects of a digital clutch control system 1200, according to an example embodiment. The digital clutch control system 1200 allows for complete locking of lace extension upon activation of the ratchet mechanism 1230. The ratchet mechanism 1230 is designed to lock-out extension (or release) of the lace, but still allow for additional lace retraction through ratcheting of the lace spool 1210. In this example, the digital clutch control system 1200 includes structures such as a lower housing 1201, an upper housing 1202, a lace spool 1210, a spool gear 1215, a locking ring 1220, a ratchet mechanism 1230, solenoids 1240A, 1240B, a lace guide 1250, a circuit board 1260, a battery 1270, and an on/off switch 1280.

In this example, the lace spool 1210 has similar components to the examples discussed above, but interacts with other components a bit differently. The lace spool 1210 includes a lace anchor 1211, a lace groove 1212, a spool bearing 1213, a lock ring groove 1214, and a spool gear 1215. The lace anchor 1211 is a U-shaped groove in the superior surface with two through holes extending into the lace groove 1212. The spool bearing interfaces the lace spool 1210 with a spool shaft 1217 that extends inferiorly to couple with a rotary bias member 1218 and the spool gear 1215. Both the lace spool 1210 and the spool shaft 1217 include an interface to couple with the rotary bias member 1218. The rotary bias member 1218 interface, the spool shaft bias member slot 1219, in the spool shaft 1217 is a vertical slot in the center of the shaft. While the bias member interface 1216 in the lace spool 1210 is an L-shaped slot formed in the inferior side of the lace spool 1210 (see FIG. 12I).

Figure 12A:
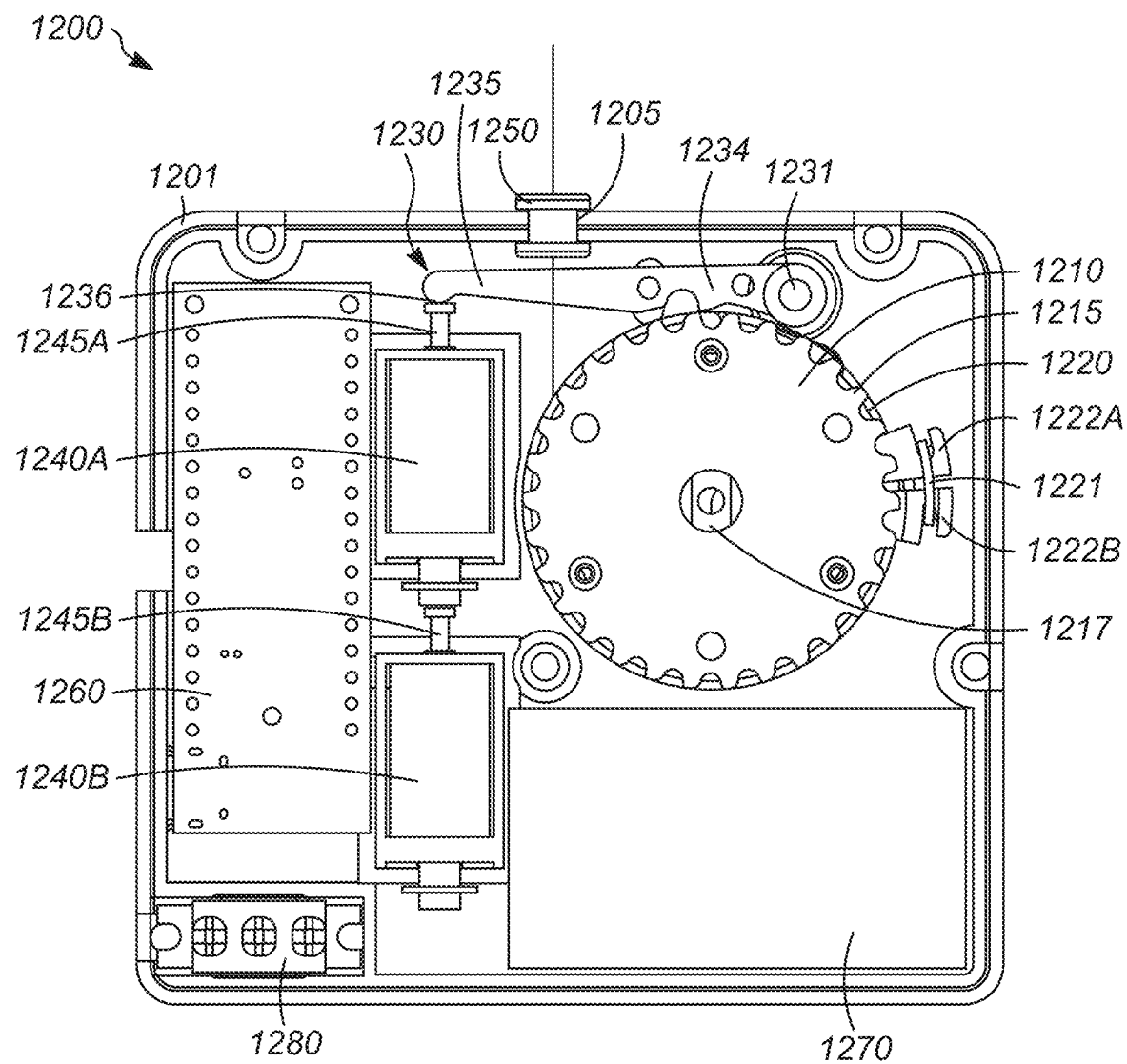
FIGS. 12A-12I are various drawings illustrating aspects of a digital clutch control system, according to an example embodiment.
Figure 12B:
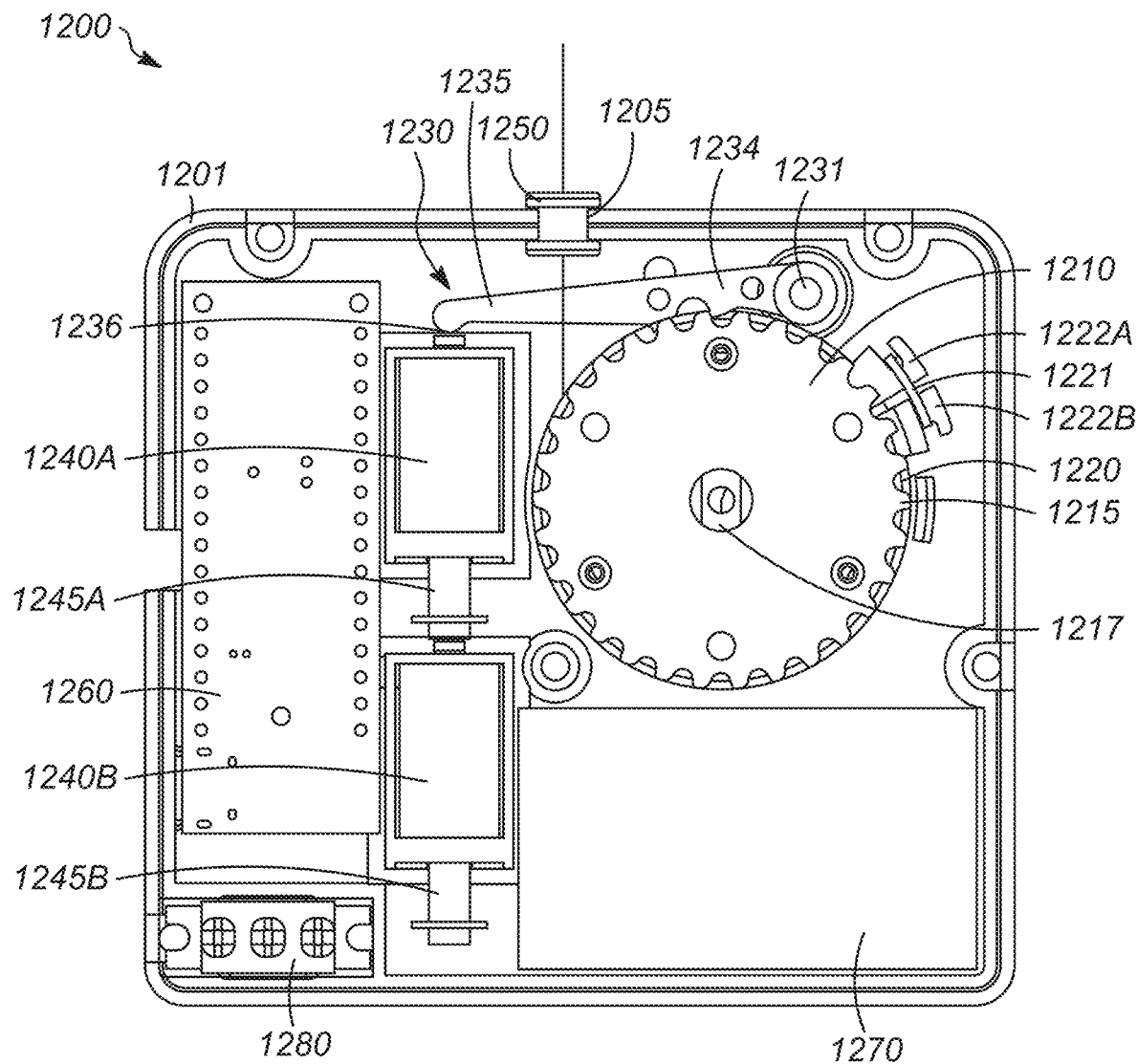
Figure 12C:
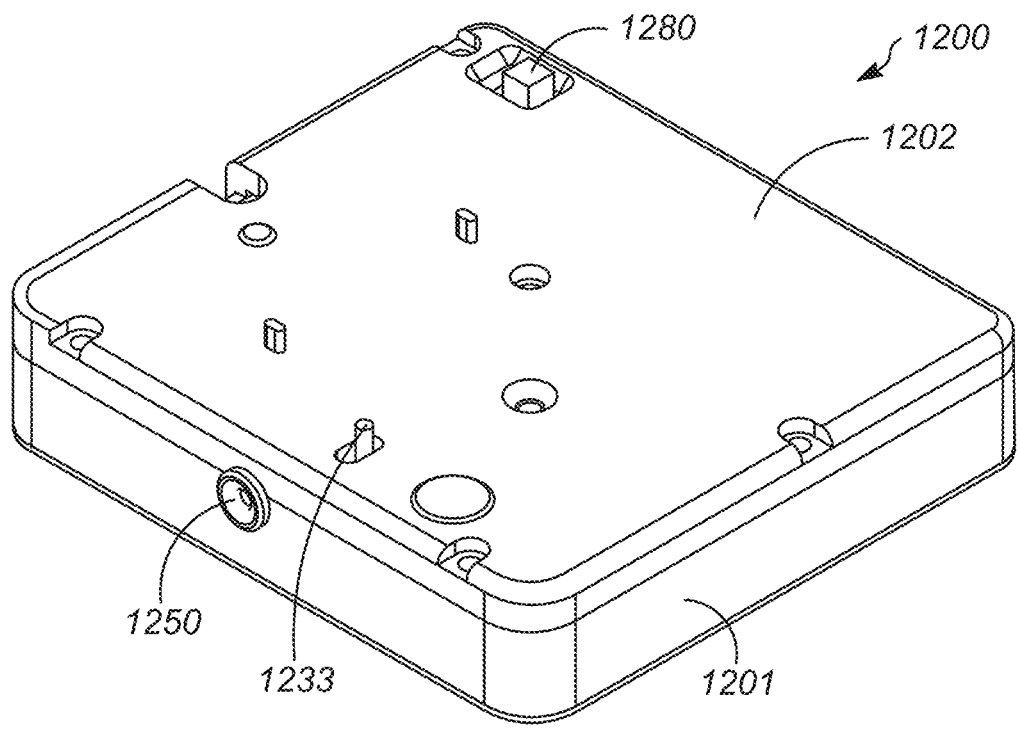
Figure 12D:
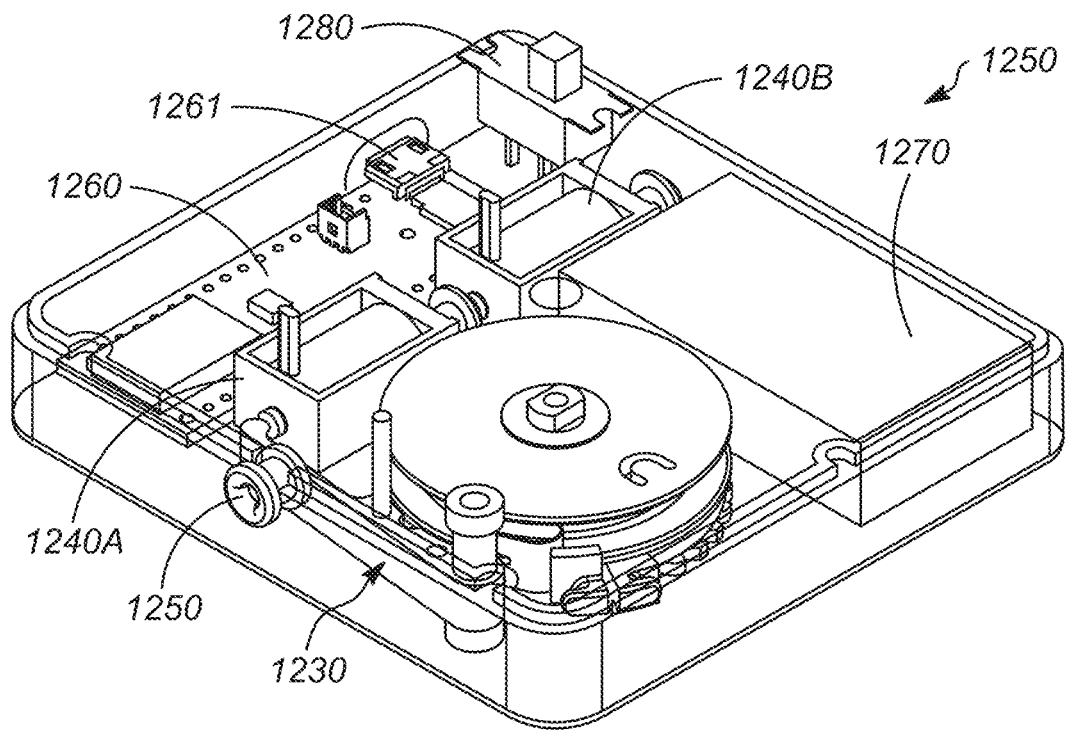
Figure 12E:
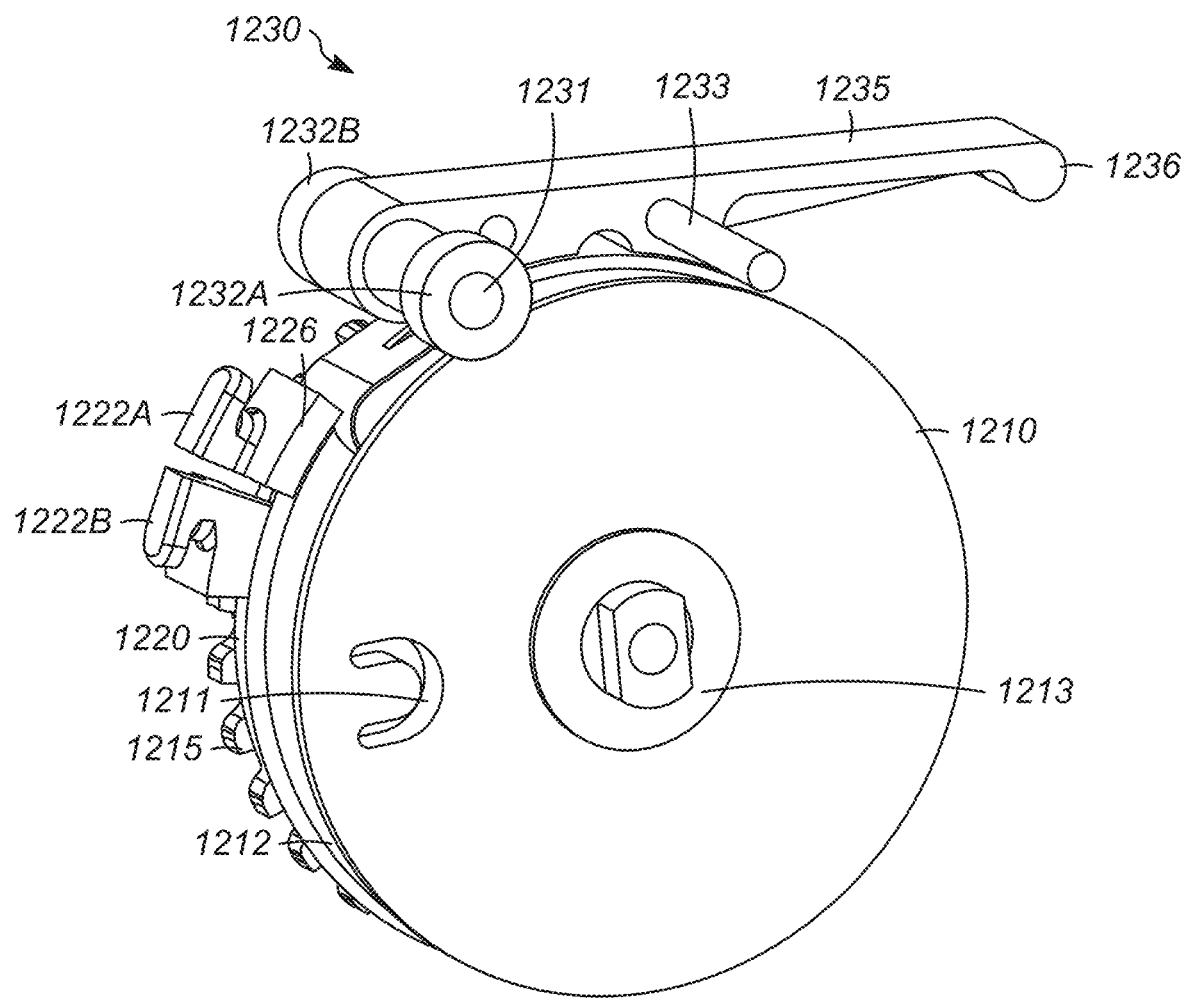
Figure 12F:
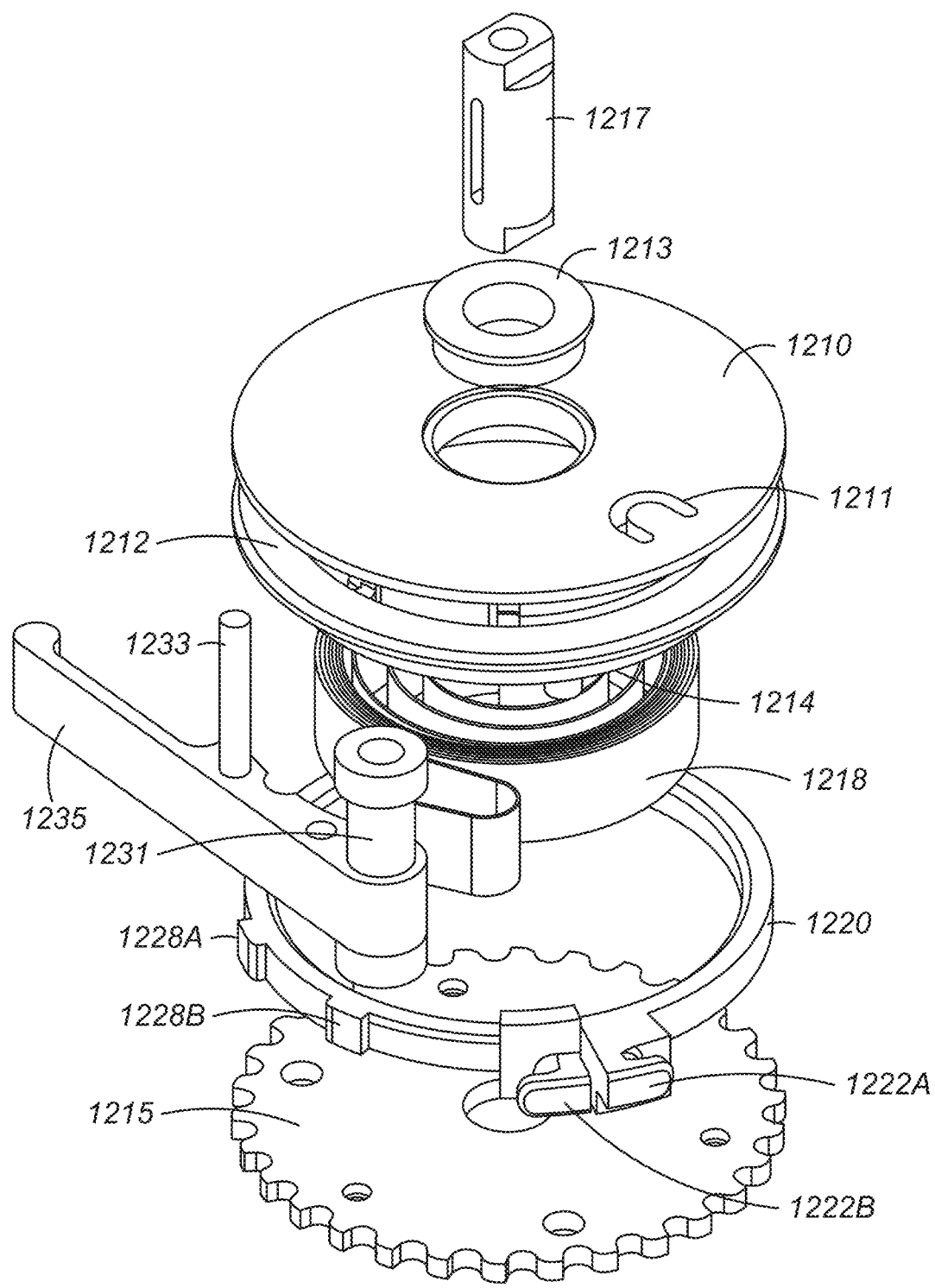
Figure 12G:
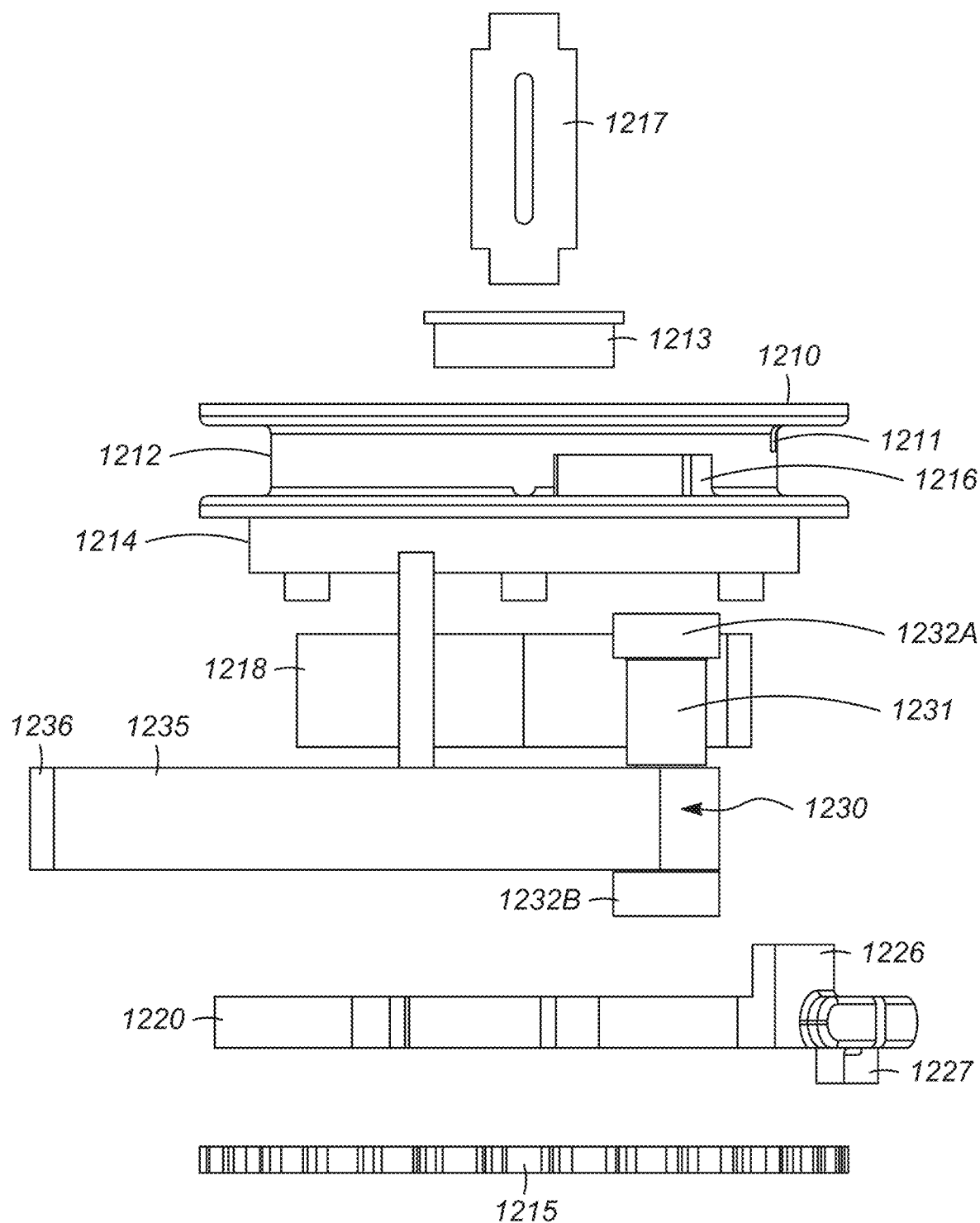
Figure 12H:
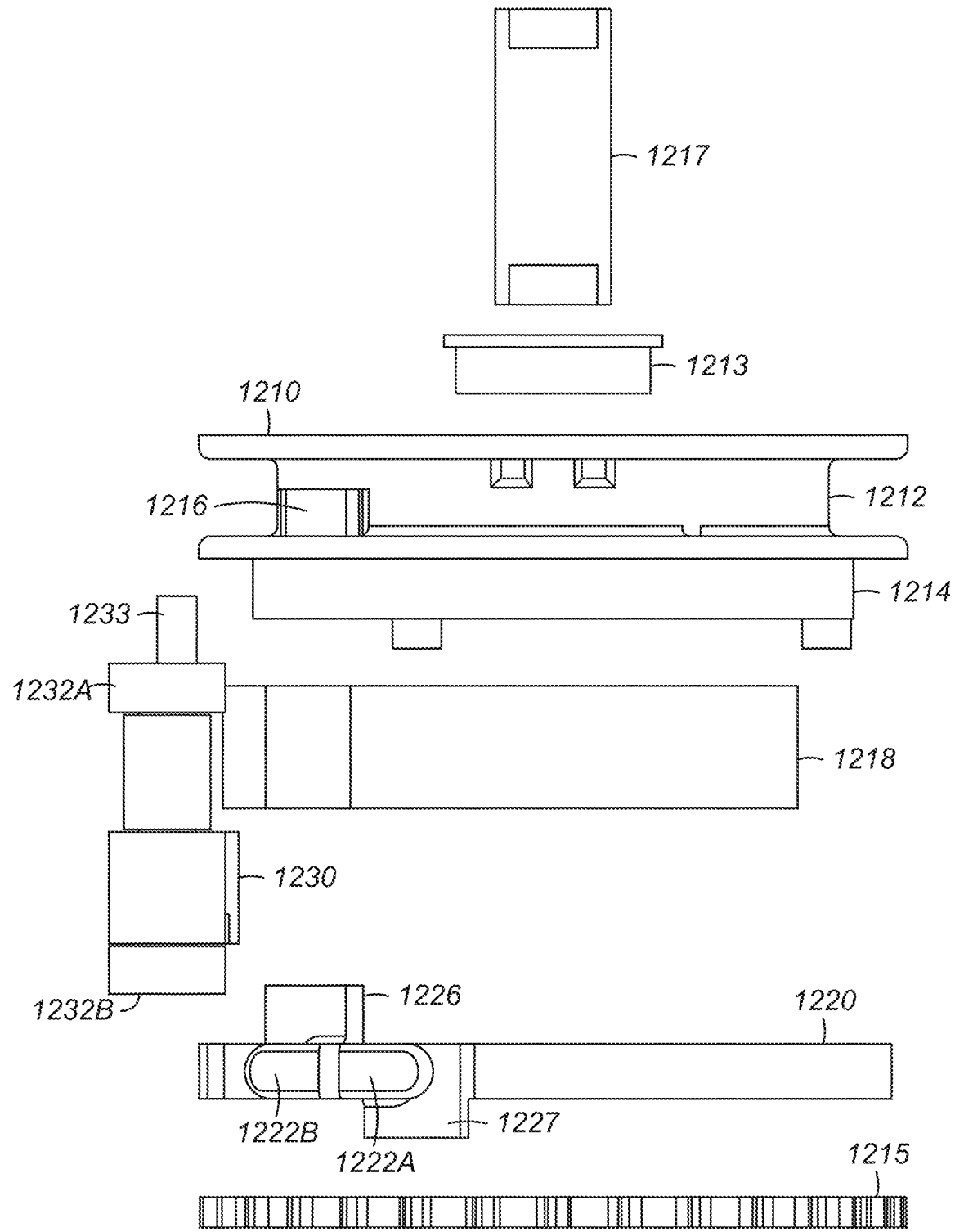
Figure 12I:
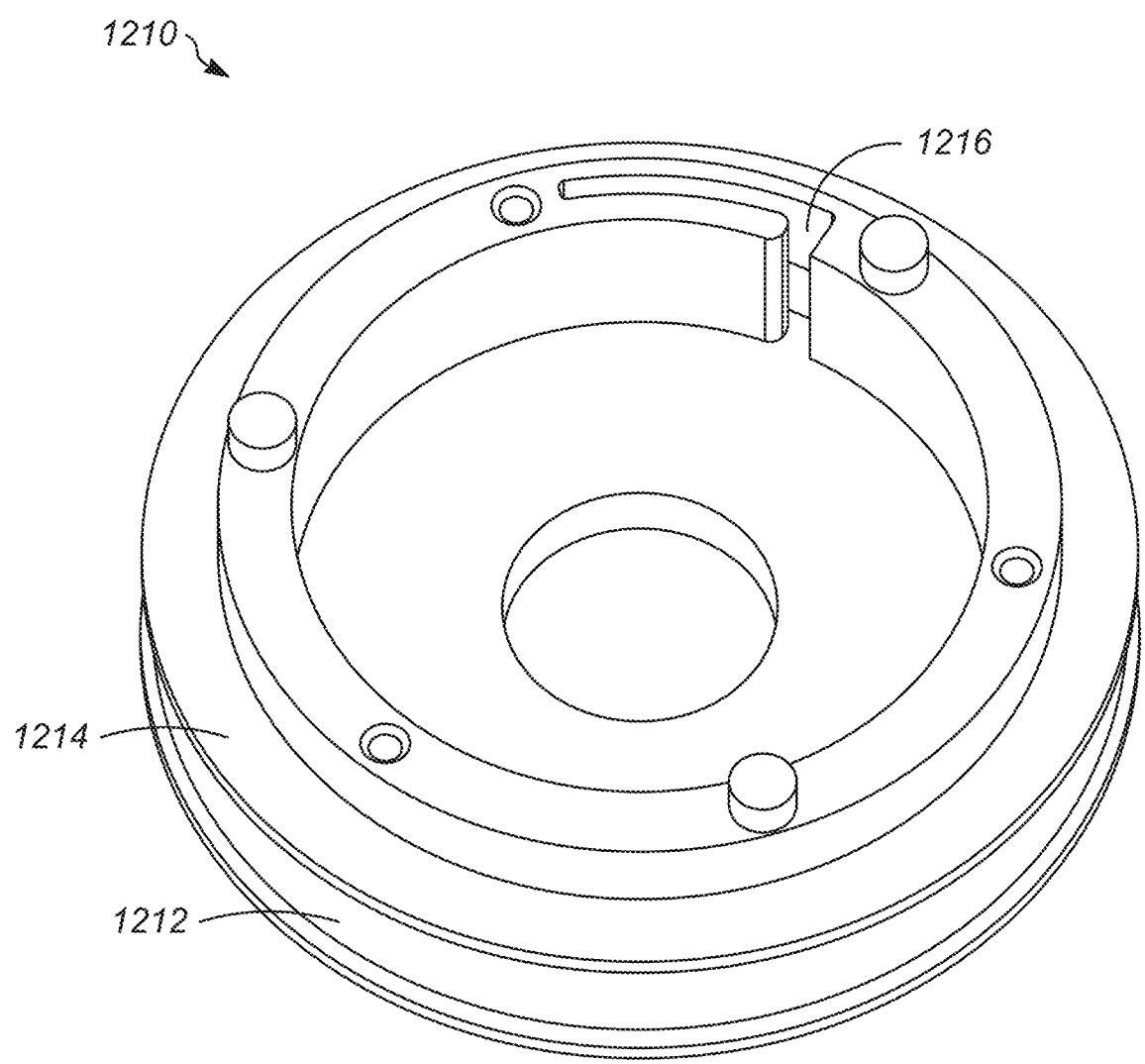
Figure 13A:
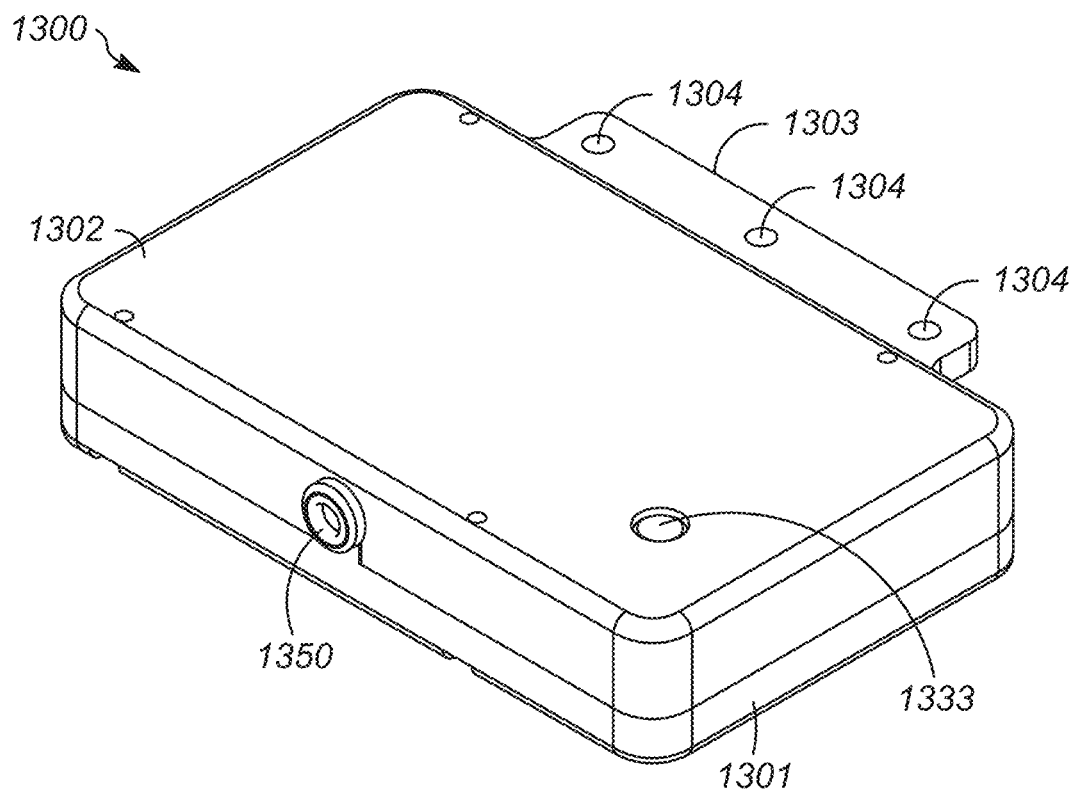
FIGS. 13A-13I are various drawings illustrating aspects of a rotary friction analog control system, according to an example embodiment.
Figure 13B:
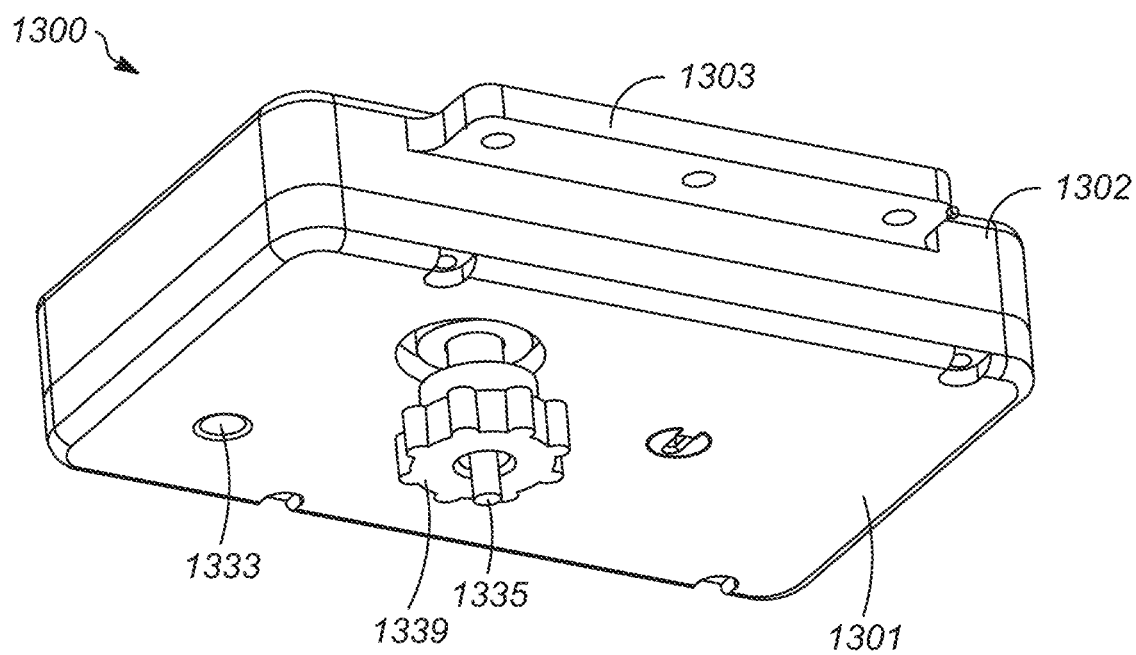
Figure 13C:
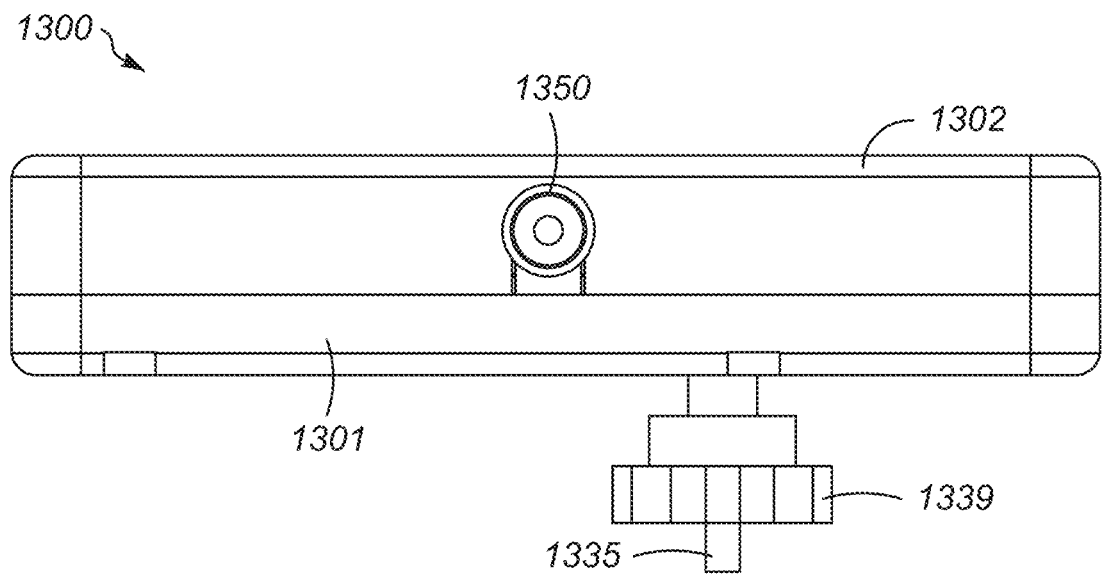
Figure 13D:
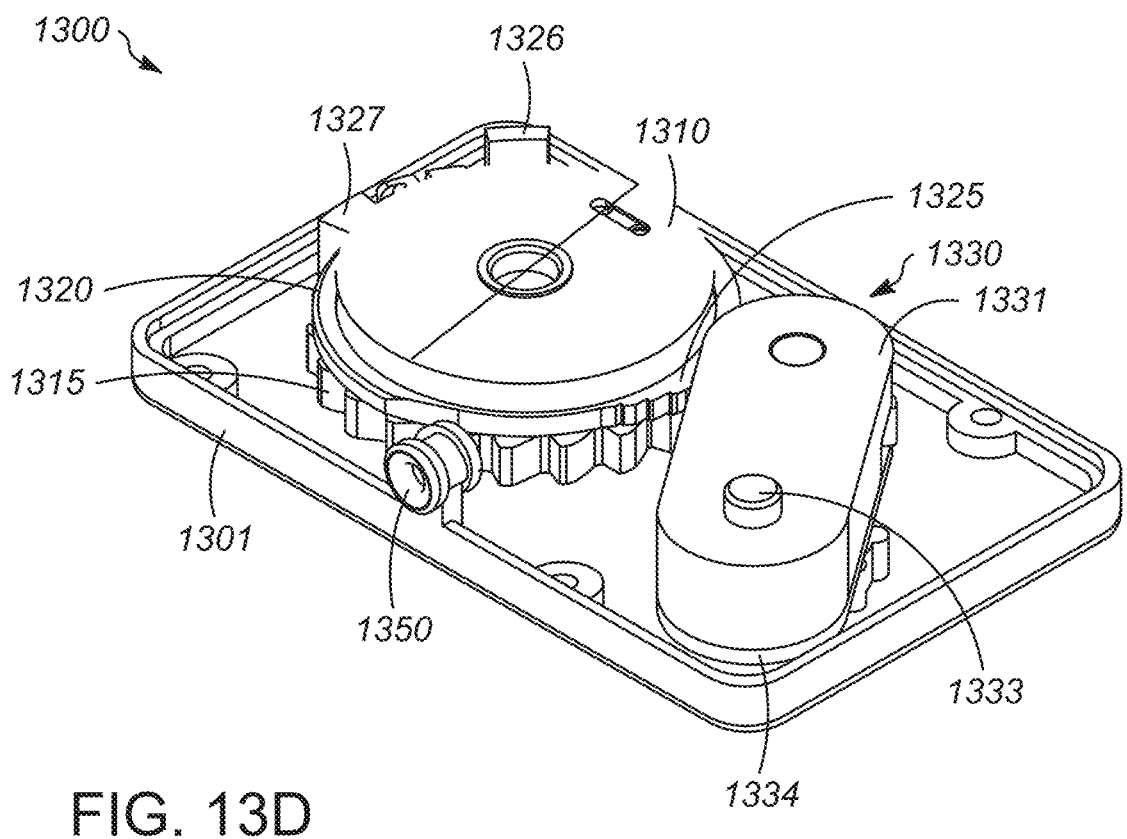
Figure 13E:
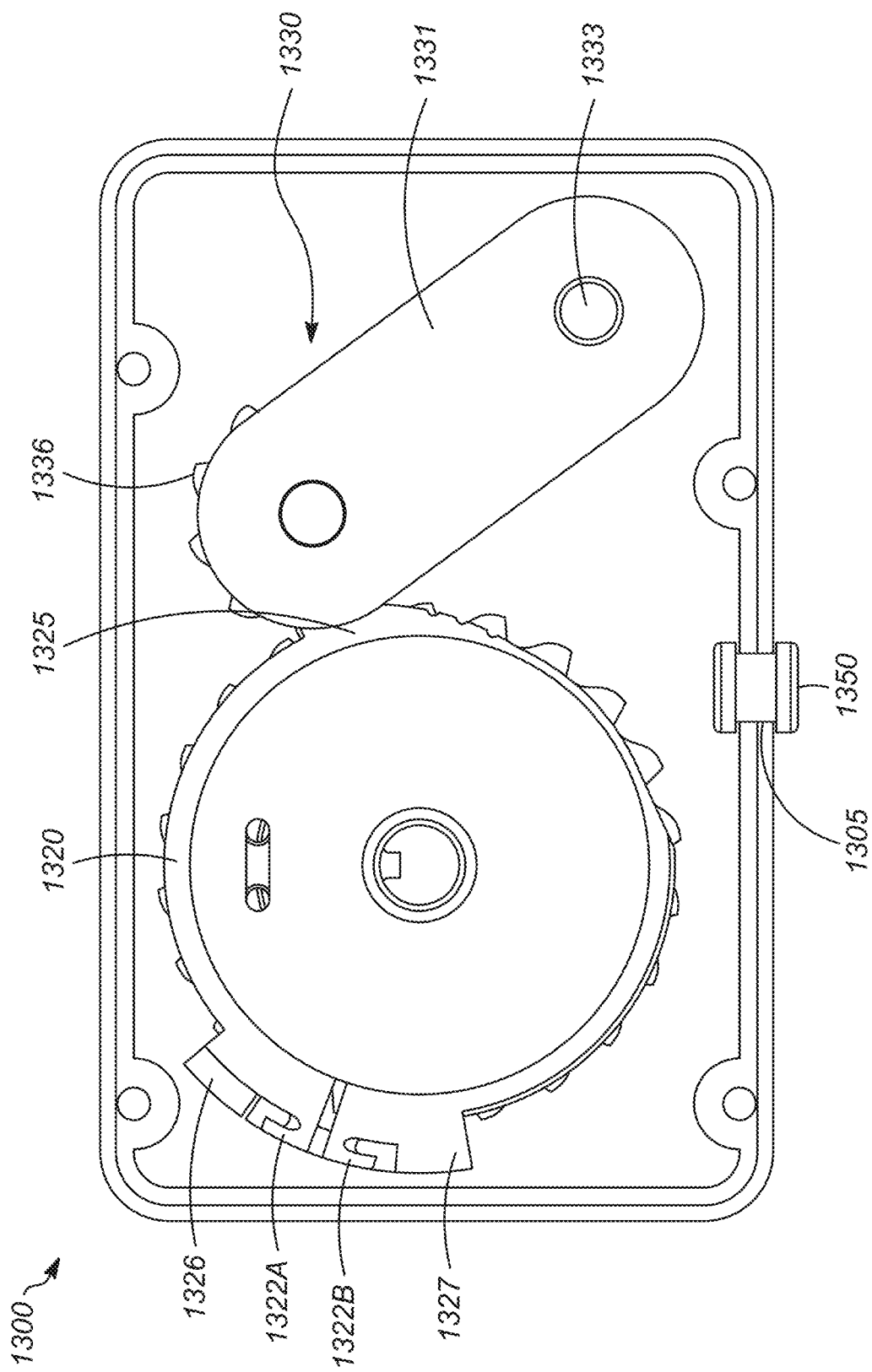
Figure 13F:
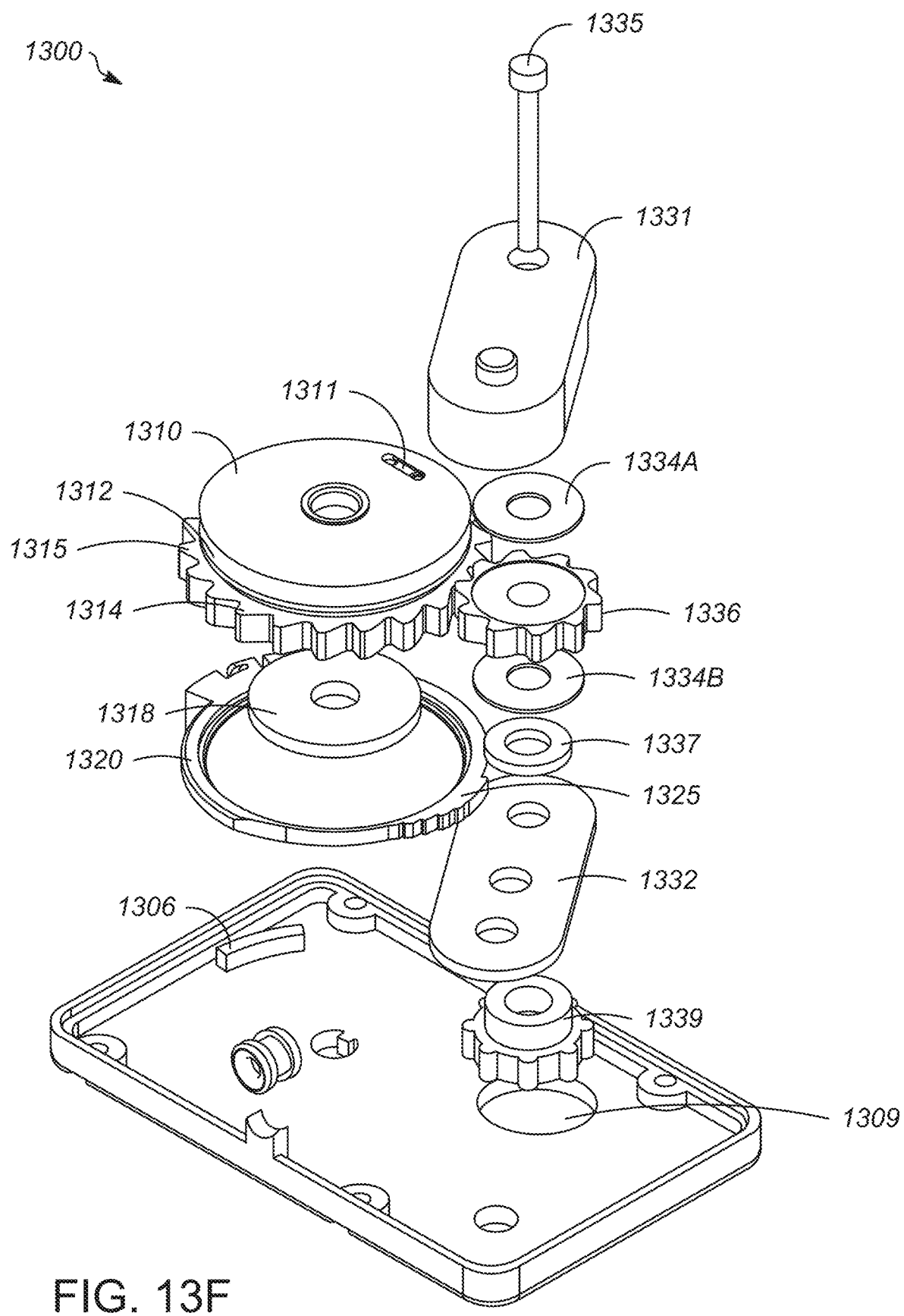
Figure 13G:
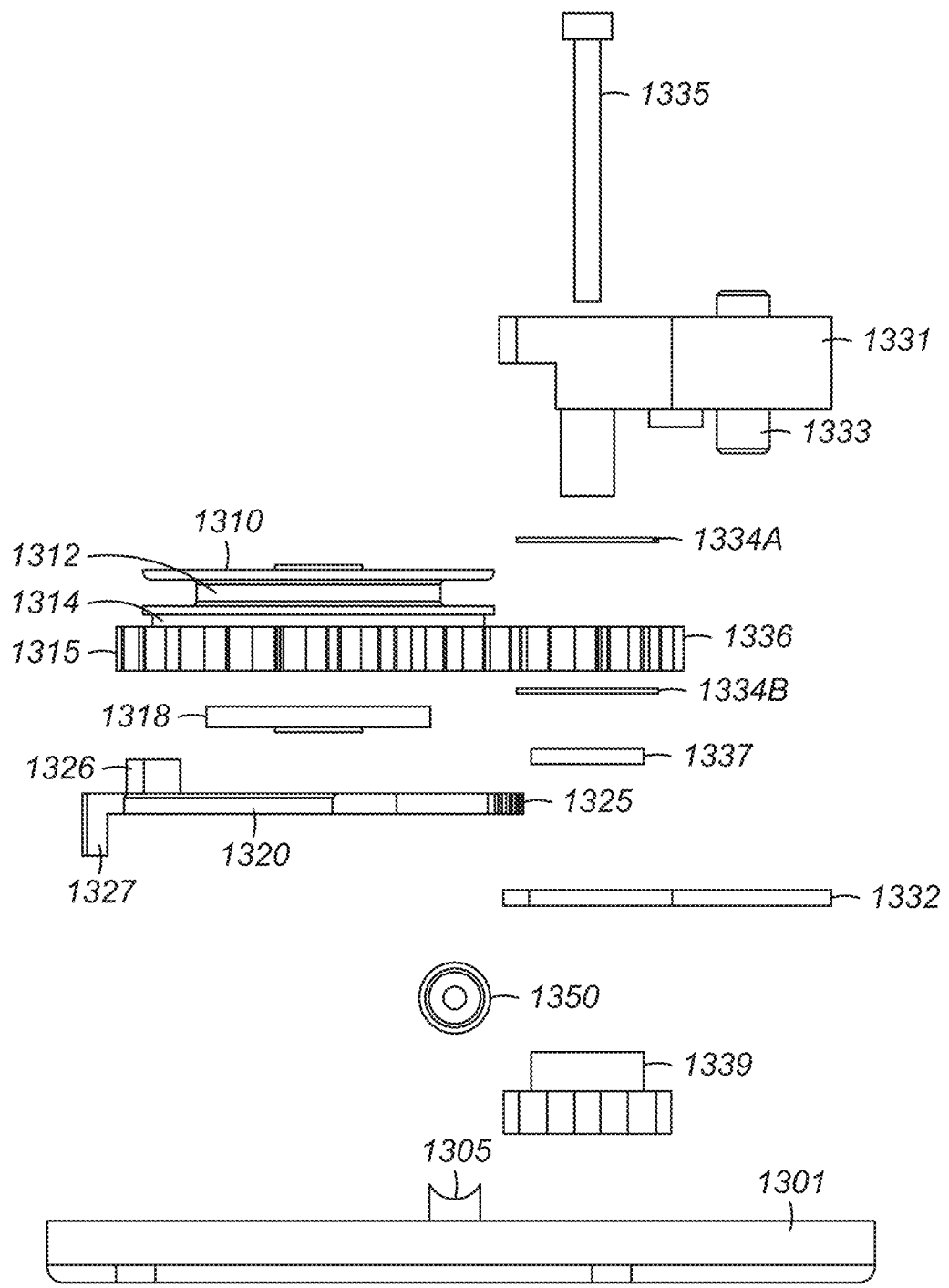
Figure 13H:
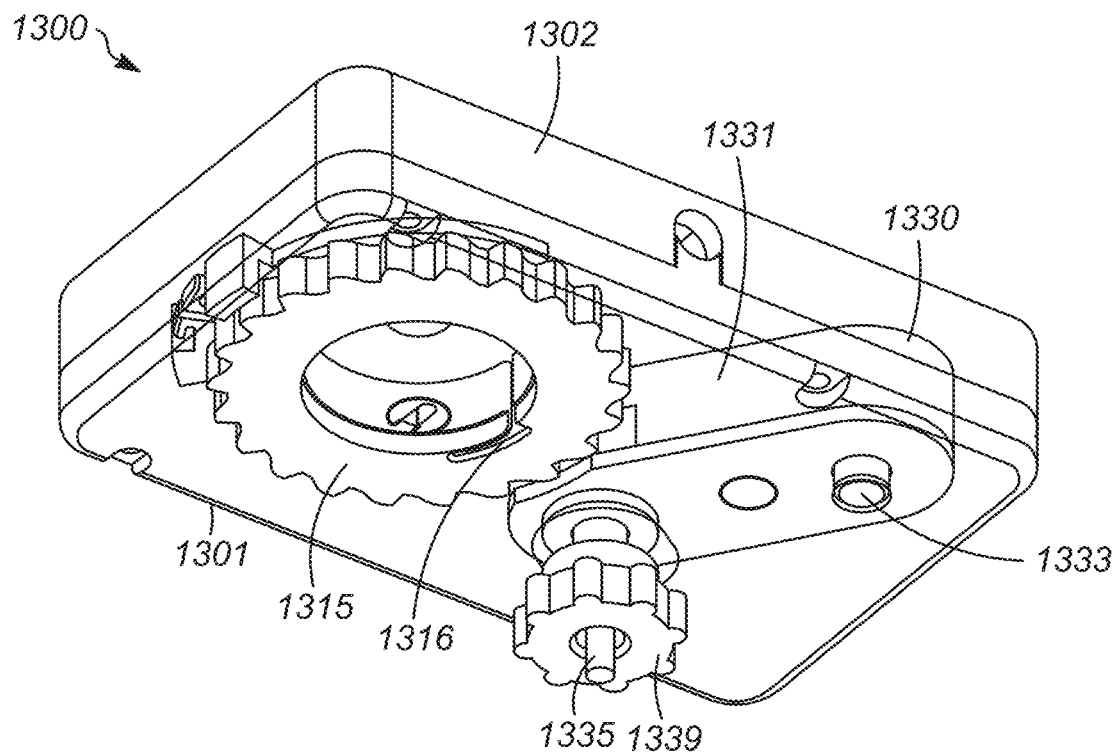
Figure 13I:
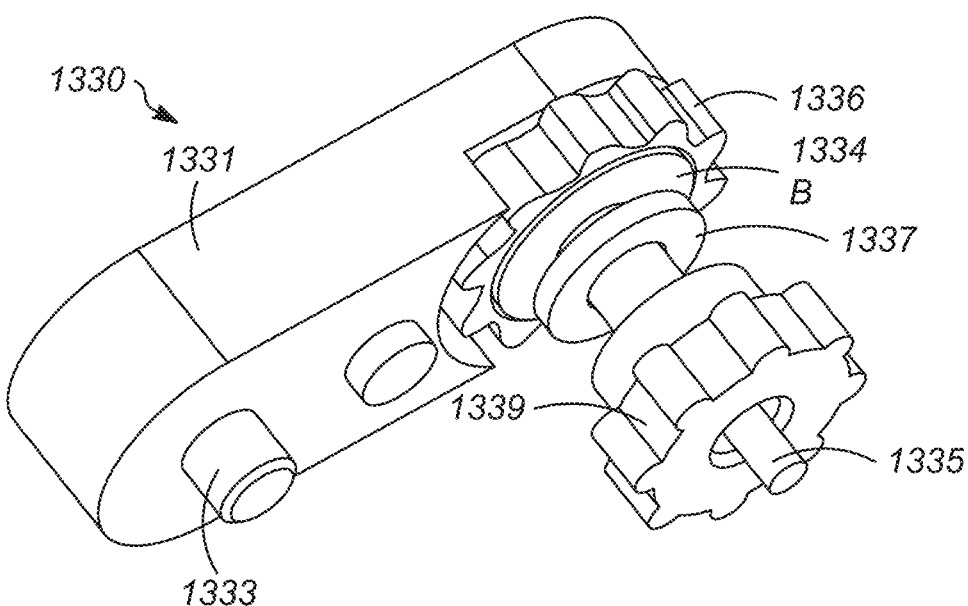

The ratchet mechanism 1230 interacts with the spool gear 1215 and the solenoids 1240A, 1240B, to form a digital clutch mechanism that can be activated based on inputs, such as from an external sensor monitoring user activity or timing circuitry within the circuit board 1260. The digital clutch mechanism is control via timing or sensors by the circuit board 1260 with power from the battery 1270. The ratchet mechanism 1230 includes a ratchet pivot shaft 1231, pivot shaft bearings 1232A, 1232B, a ratchet manual release 1233, a ratchet tooth 1234, a solenoid arm 1235 and a solenoid interface 1236. The ratchet mechanism 1230 is biased by a bias member either a rotary bias member built into the ratchet pivot shaft 1231 or by a coil spring (or similar bias member) positioned between the lower housing 1201 and the ratchet solenoid arm 1235 (omitted from figures for clarity purposes). Accordingly, the ratchet tooth 1234 is biased against the spool gear 1215 as illustrated in FIGS. 12A-12B (FIG. 12B in particular illustrates the digital control mechanism 1200 in ratcheting mode). The ratchet tooth 1234 includes an angled surface that rides on corresponding rounded tooth surfaces on the spool gear 1215 teeth, with opposing catch surfaces to prevent the spool gear 1215 from rotating in a clock-wise direction with the digital rotary clutch control mechanism 1200 is in ratcheting mode.

To activate free mode, and disable the ratchet mechanism 1230, the circuit board 1260 triggers the solenoids 1240A, 1240B to activate, which results in extending the solenoid shafts 1245A, 1245B. Note, the system illustrated includes two solenoids to increase the overall strength of the solenoid activation, other examples can utilize one or more than two solenoids as needed to achieve the desired power. Upon activation, the solenoid shafts 1245A, 1245B (through 1245A) push on the ratchet solenoid arm 1235 at the solenoid interface 1236 to pivot the ratchet mechanism 1230 away from engagement with the spool gear 1215. In free mode, the locking ring 1220 can rotate to position one of the ratchet lock-out tabs 1228A, 1228B into position adjacent the ratchet tooth 1234. In the example illustrated in FIG. 12A, ratchet lock-out tab 1228A is positioned adjacent the ratchet tooth 1234. The other ratchet lock-out tab 1228B operates to lock-out the ratchet mechanism 1230 under certain conditions without activation of the solenoids 1240A, 1240B—for example after a certain amount of ratcheting (retraction of lace) occurs and the locking ring 1220 has rotated into a position where the lower lock release tab 1227 engages lock release housing tab (not illustrated—see e.g., FIG. 11E, 1106) on the lower housing 1201. In free mode, the upper lock release tab 1226 engages the lock release housing slot (or tab) (see e.g., FIG. 11C, 1107) to release tension on the locking ring 1220 and allow the lace spool 1210 to rotate more freely.

In some examples, the primary purpose of the locking ring is to limit the amount of time the solenoid needs to be energized to reduce power consumption. Once the solenoid releases the pawl (ratchet), the spool starts to spin which in turns spins the locking ring. The locking ring prevents the pawl from re-engaging even with power to the solenoid (or similar digital/powered control device) turned off. Another benefit provided by the locking ring involves preventing noise during retraction. For example, once the spool starts to retract, the locking ring can impedes the motion of the pawl to prevent chatter on the gear teeth.

FIGS. 13A-13I are various drawings illustrating aspects of a rotary friction analog control system 1300, according to an example embodiment. The rotary friction analog control system 1300 operates in a manner similar to the rotary damper control mechanism 1100 discussed above. The rotary friction analog control system 1300 substitutes a friction mechanism 1330 for the damper mechanism 1130 discussed above. Otherwise, other components of the rotary friction analog control system 1300 are designed and function similarly to those discussed above in reference to the rotary damper control mechanism 1100, for example the lace spool 1310 and related components are comparable to the lace spool 1110 and related components. Additionally, the locking ring 1320 functions in a manner comparable to the locking ring 1120 including the lock wedge 1325 operating to disengage the friction mechanism 1330 by pushing the friction fear 1336 away from the spool gear 1315. As is the case throughout this disclosure, components with similar numbering schemes (e.g., lace spool 1110 and lace spool 1310) are comparable structures with similar features and functions (except where noted).

In this example, the friction mechanism 1330 introduces drag into the lace spool 1310 mechanism to slow the extension of the lace out of the control system under certain conditions (similar to the damping mechanism 1130). The friction mechanism 1330 can include a pivoting friction housing 1331, a pivoting friction mount plate 1332, a pivot shaft 1333, friction washers 1334A, 1334B, a friction shaft 1335, a friction gear 1336, a friction bearing 1337, and a friction adjustment knob 1339. The majority of the friction mechanism 1330 is contained within the pivoting friction housing 1331. The pivoting friction housing 1331 couples to the pivoting friction mount plate 1332 to hold the friction washers 1334A, 1334B, the friction gear 1336, and the friction bearing 1337 with the friction shaft 1335 running through those components. The pivoting friction housing 1331 and pivoting friction mount plate 1332 form an assembly that pivots on the pivot shaft 1333 around pivot point 1338. In an example, the friction shaft includes a threaded inferior end that extend through a friction housing opening 1309 in the lower housing 1301 to receive the friction adjustment knob 1339. The friction adjustment knob 1339 interacts with the friction bearing 1337 to compress the friction washers 1334A, 1334B against the friction gear 1336 to generate an adjustable amount of friction resisting rotation of the friction gear 1336.

While not specifically illustrated in FIGS. 13A-13I, the pivoting friction housing 1331 and pivoting friction plate 1332 are biased by a bias member, such as a coil spring, to force the friction gear 1336 into engagement with the spool gear 1315. An arrangement similar to that illustrated in FIG. 11A, where the damper bias member 1139 is shown biasing the damping mechanism 1130 with a coil spring disposed between a portion of the lower housing 1101 and the pivoting damper mount 1131, could be utilized within this embodiment. Alternatively, a rotary bias member, such as a torsional spring, could be integrated into the pivot shaft 1333 to bias the friction mechanism 1330 against the spool gear 1315. To engage pivoting of the friction mechanism 1330, the friction housing opening 1309 in the lower housing 1301 is an oblong hole of sufficient size to enable the friction adjustment knob 1339 and friction shaft 1335 to move freely.

Similar to the locking ring 1120, the locking ring 1320 includes a lock wedge 1325 that operates to disengage the friction mechanism 1330 from the spool gear 1315 when rotated into a certain position. The lock wedge 1325 includes a grooved ramped surface to engage the friction gear 1336 as the locking ring 1320 rotates in a clockwise direction (as viewed from above (e.g., FIG. 13E). In some examples, the lock wedge 1325 portion of the locking ring 1320 engages another portion of the friction mechanism 1330, such as the pivoting friction mount plate 1332 or the pivoting friction housing 1331, to pivot the friction mechanism 1330 away from engagement with the lace spool 1310. The lock wedge portion of the locking ring discussed above in other examples can also, similarly, engage portions of the damping mechanism 1130 or generator mechanism 1030 other than the respective gears (e.g., damper gear 1136 or drive gear 1040).

FIGS. 14A-14D are various drawings illustrating aspects of a friction-based analog control system 1400A that utilizes opposing directional fabrics, according to an example embodiment. The following example utilize a mohair material with directional hairs in a friction-based analogy control system. The mohair mechanism is modeled on the concept used by back country skiers using ski skins to ascend a mountain on downhill skis. Original ski skins were produced from seal skins that have stiff directional hairs. Today, most ski skins utilize a synthetic approximation of seal skin, such as mohair fabric.

Figure 14A:
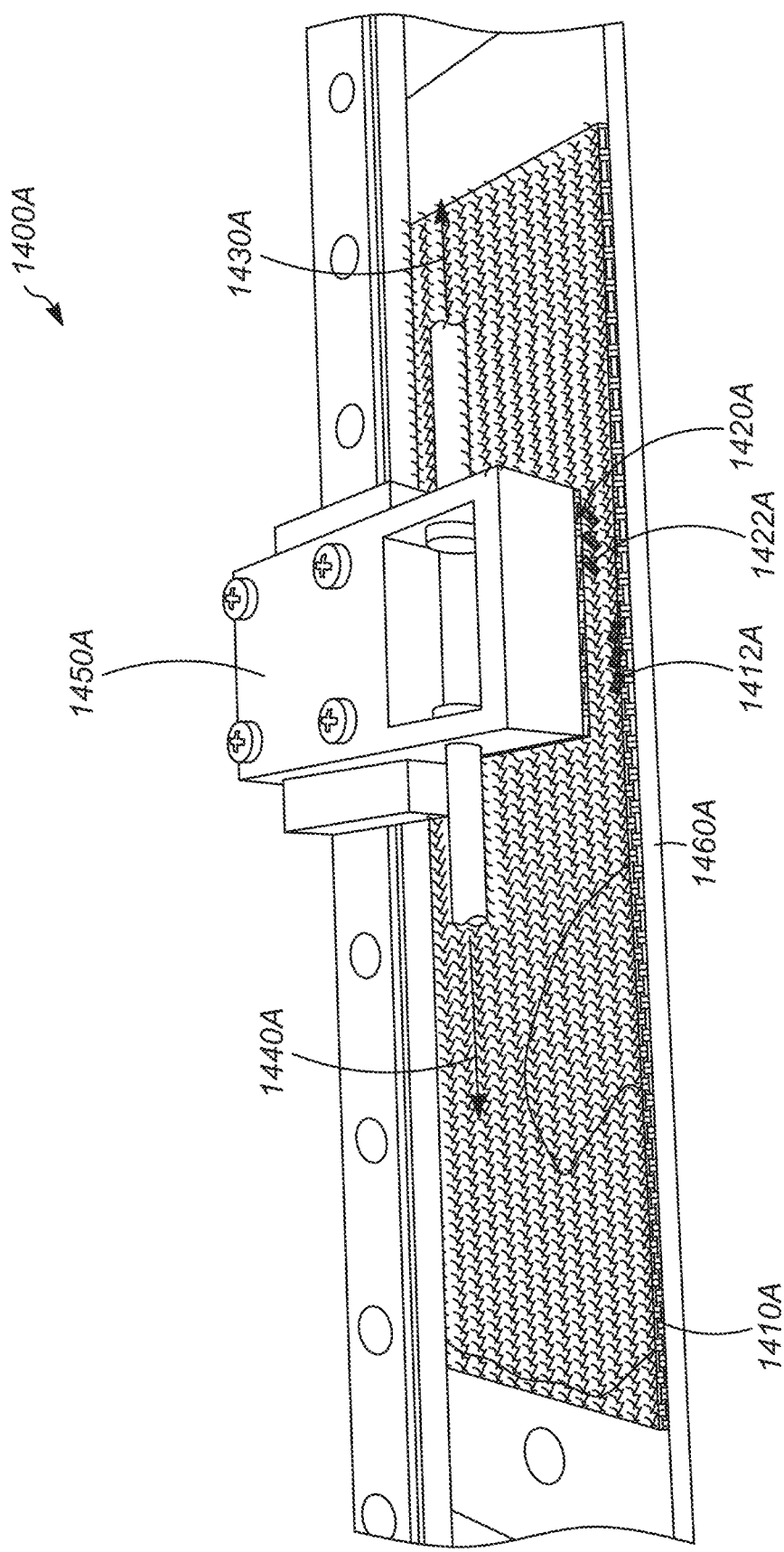
FIGS. 14A-14D are various drawings illustrating aspects of a friction-based analog control system using a friction fabric-based control system, according to an example embodiment.

FIG. 14A illustrates a test rig used in testing the mohair friction-based analog control system 1400A. In this example, a first directional fabric 1410A is adhered to a housing 1460A, which is intended to represent a housing of a control device to be affixed to a person's torso or a fixed portion of an adaptive support apparel. A second directional fabric 1420A is adhered to an inferior surface of a control structure 1450A, which is representative of the control device or mechanism that is applying various tensions on a lace or lace cable attached to a support portion of the adaptive apparel, such as a bra strap on an adaptive bra. In this example, down force vector 1440A is representative of the soft tissue weight (e.g., breast tissue weight) plus gravity, while up force vector 1430A is representative of a constant support force. Note, the terms "up" and "down" are used in a relative sense, but are representative of the effect that would be applied to a support portion of an adaptive apparel during use such as running. Also, in an actual control device, the down force vector 1440A is a control lace or similar structure attached to a support portion of the adaptive apparel. Similarly, the up force vector 1430A is a tension device, such as a spring to provide a constant support force to the control lace. In this example, the constant support force (up force vector) 1430A is similar to the breast tissue weight.

Each of the directional fabrics include directional hair or fibers, represented by first directional fibers 1412A and second directional fibers 1422A. As illustrated, these directional fibers are oriented in opposing directions to generate a much greater friction force in the opposing direction and allow easier movement between the opposing fabrics in the other direction. In this example, the first and second directional fabrics 1410A, 1420A altered induced different force levels to produce direction changes as detailed in Table 2 (referencing down force vector 1440A (DOWN) and up force vector 1430A (UP)):

TABLE 2

| Direction | Force (lbs) (mohair only, 720 mm²) |
|---|---|
| DOWN TO DOWN | 0.5 |
| DOWN TO UP | 0.8 |
| UP TO UP | 0.5 |
| UP TO DOWN | 2.4 |

As illustrated by the example testing measurements, the transition that requires overcoming the opposing directional fibers on the first and second directional fabrics 1410A, 1420A is the only transition where the fabrics create a significant increase in the required force. In this example, the DOWN is representative of extension of a lace cable from a control mechanism and UP is representative of retraction of a lace cable from a control mechanism. The arrangement of opposing directional fabrics functions as a dampening mechanism on the supported soft tissue, such as breast tissue in an adaptive bra. The friction-based analog control mechanism in FIG. 14A can produce results similar to those shown in FIG. 8, where the cycle for the breast tissue (e.g., 1450A moves comparably to 820) is reduced in amplitude and shifted in comparison to the torso (e.g., 1460A moves comparably to 810) cycle.

Figure 14B:
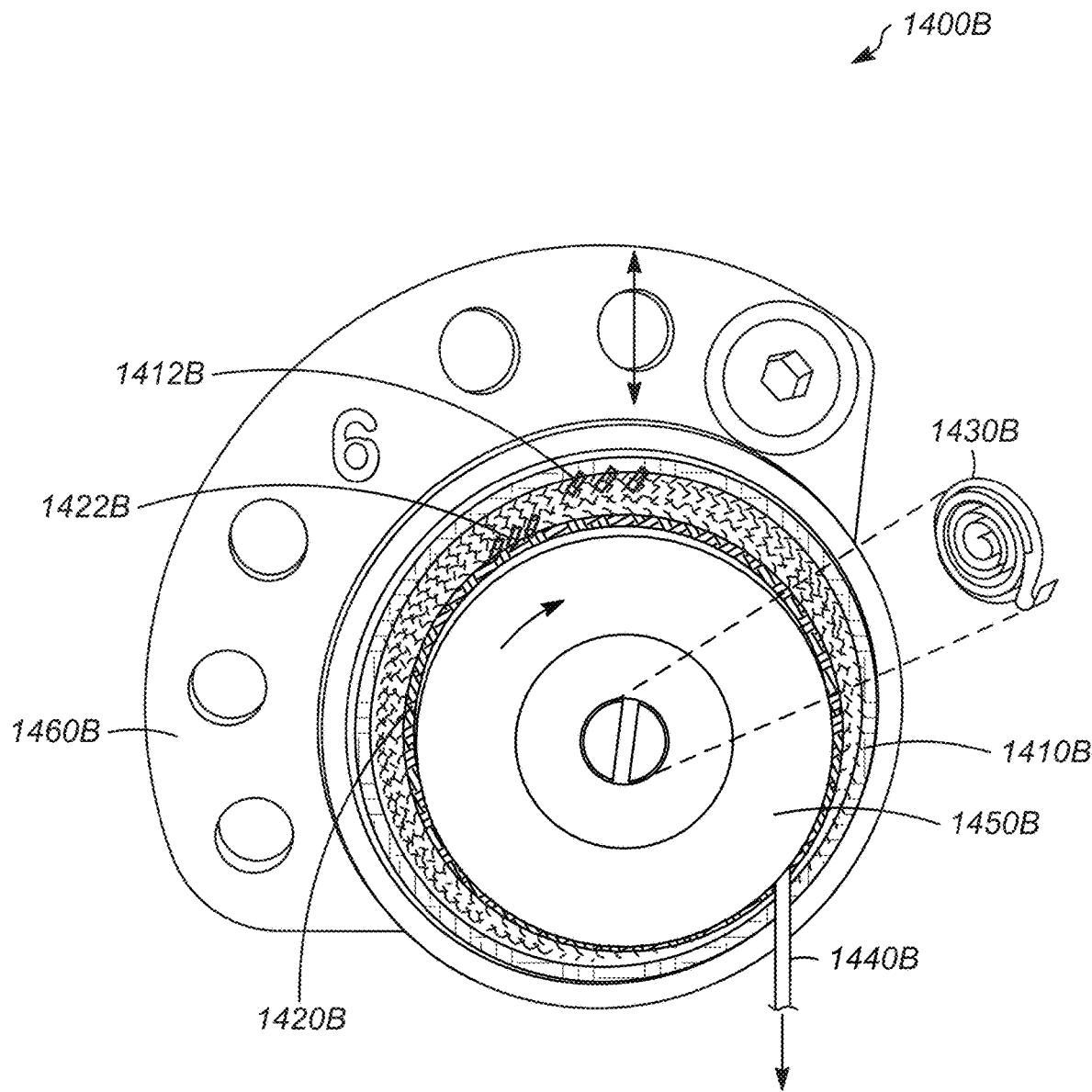

FIG. 14B illustrates a friction-based analog control mechanism 1400B, according to an example embodiment. In this example, opposing directional fabrics are used in a rotary control mechanism designed to be integrated into a piece of adaptive apparel, such as an adaptive bra. The friction-based analog control mechanism 1400B includes a first directional fabric 1410B affixed to an inner cylindrical surface of housing 1460B. The friction-based analog control mechanism 1400B also includes a second directional fabric 1420B affixed to an outer cylindrical surface of a control structure 1450B that applies a tension to control lace 1440B generated in part by a tension device 1430B. In this example, the tension device 1430B is a torsion spring positioned within the hub of the control structure 1450B. The control structure 1450B is a lace spool in this example, that moves rotationally with respect to the housing 1460B to release or retract the control lace 1440B.

Again, the first and second directional fabrics 1410B, 1420B are positioned opposing each other with directional fibers 1412B, 1422B angled in opposing directions. The opposing directions create an increased friction between the housing 1460B and rotation of the control structure (lace spool) 1450B when in a transition between retracting (counter-clockwise rotation) and extending (clockwise rotation) of the control structure 1450B.

Figure 14C:
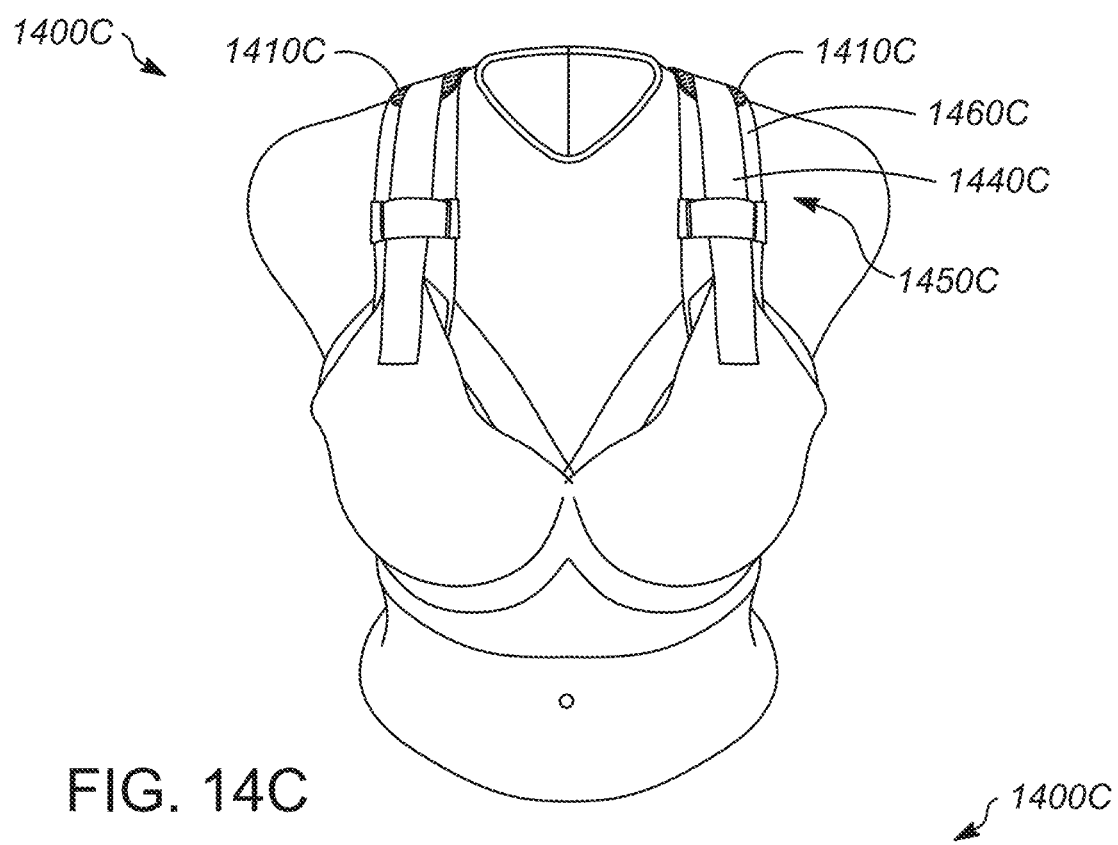
Figure 14D:
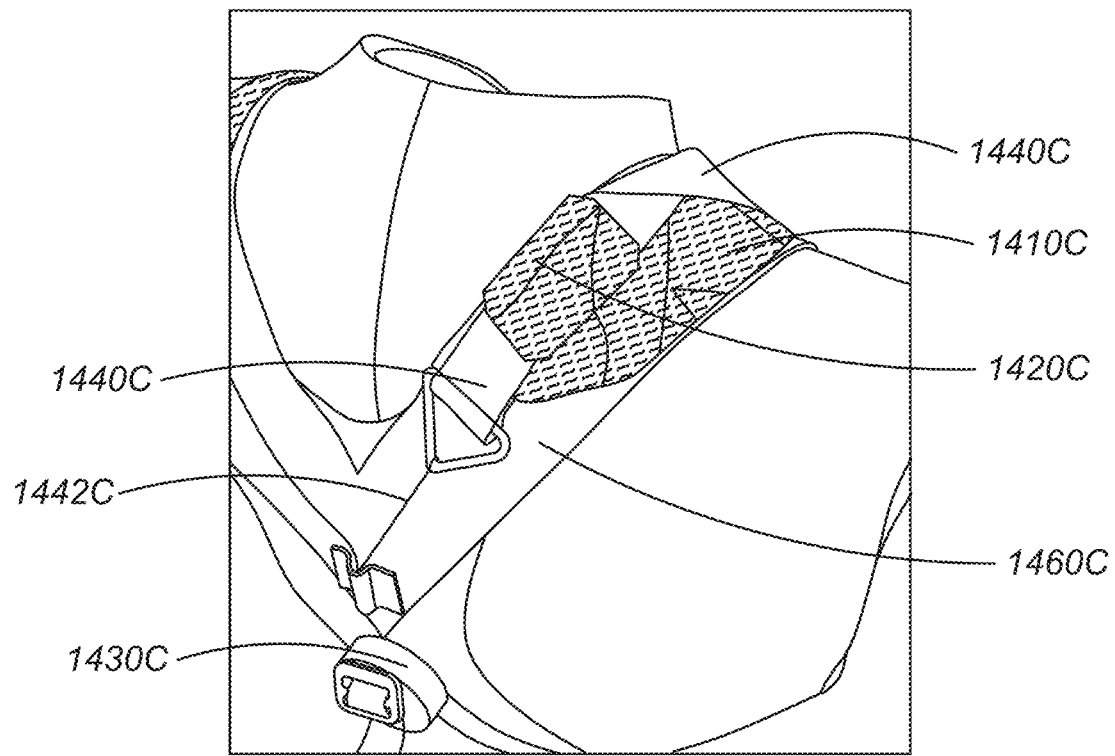

FIGS. 14C and 14D illustrate integration of a friction-based analog control device 1400C into an adaptive bra. In this example, a control structure 1450C includes the first directional fabric 1410C that is affixed to a fixed portion of a bra strap (e.g., housing 1460C or fixed shoulder strap 1460C). The control structure 1450C further includes a second directional fabric 1420C affixed to a moveable portion of the bra strap 1440C coupled to a support portion of the adaptive bra. In this example, the moveable bra strap 1440C portion of the control structure 1450C is coupled to a control lace 1442C (shown in FIG. 14D) which receives a constant tension from tension device 1430C.

In this example, the tension device 1430C applies a constant tension on the control lace 1440C to provide support to the support portion of the adaptive bra. The first and second directional fabrics 1410C, 1420C operate to increase friction between the control structure 1450C and the fixed bra strap (housing) 1460C when the control structure is transitioning from retracting (pulling up on the support portion of the adaptive bra) to extending (e.g., allowing the support portion of the adaptive bra to move downward). In other words, the first and second directional fabrics 1410C, 1420C, operate to increase the break-away force needed to transition between retracting and extending (e.g., a change in direction between the first and second directional fabrics that move against the opposing fibers). As discussed above, the interaction between the first and second directional fabrics operates within the adaptive support garment to modify the support characteristics, such as reducing amplitude of the cycle and/or shift the cycle with respect to the center of mass.

Figure 15A:
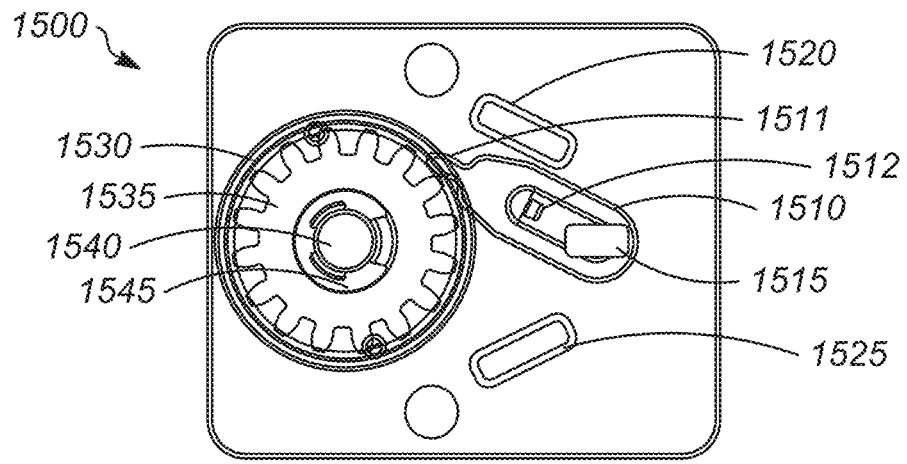
FIGS. 15A-15C are various drawings illustrating aspects of an analog control system, according to an example embodiment.
Figure 15B:
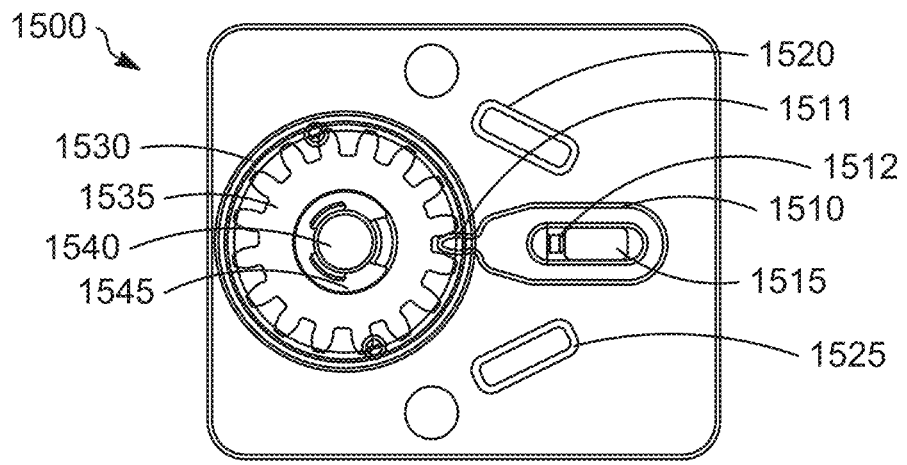
Figure 15C:
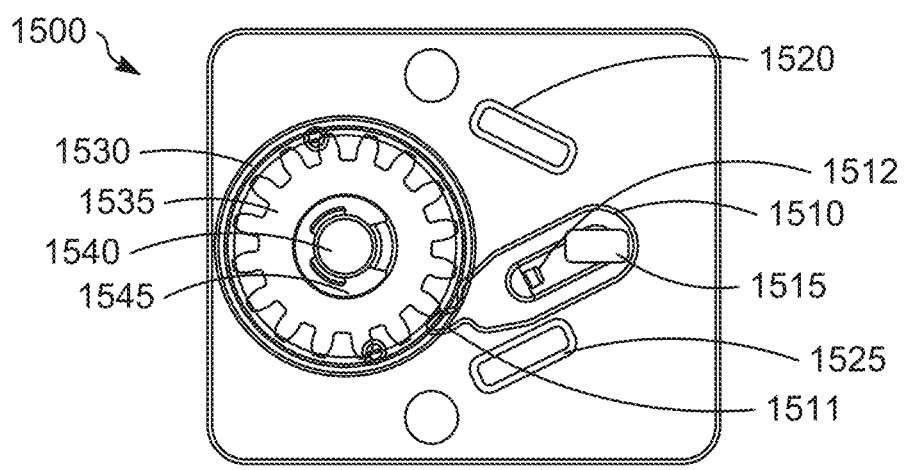

FIGS. 15A-15C are various drawings illustrating aspects of an analog control system 1500 that utilizes a spool gear and tensioned tooth member, according to an example embodiment. The analog control system 1500 is a modular control device designed to mimic the function of the directional fabric system discussed above. In this example, the analog control system 1500 includes components, such as a tensioned tooth member 1510, a lock stop 1515, an extension stop 1520, a retraction stop 1525, a lace spool 1530, a spool gear 1535, a spool hub 1540, and spool retention washer 1545. FIG. 15A illustrates the analog control system 1500 in an extension state where the lace spool 1530 is free to rotate in a counter-clockwise direction to allow extension of a lace cable (not illustrated). FIG. 15B illustrates the analog control system 1500 in a locked state where a gear tooth 1511 of the tensioned tooth member 1510 is engaged with spool gear 1535 and tension device 1512 is engaged with the lock stop 1515. FIG. 15C illustrate the analog control system 1500 in a retraction state where the lace spool 1530 is free to rotation in a clockwise direction to retract the lace cable. In the retraction state the lace spool 1530 is biased to move in the clockwise direction by a tension spring embedded within (or around) spool hub 1540.

In operation, the analog control system 1500 is going to exhibit increased break-away force in transitions between extension state to retraction state as well as retraction state to extension state. The increased break-away force is generated by the tensioned tooth member 1510 engaging the spool gear 1530 between the gear tooth 1511 and the tension device 1512. When in the locked state, illustrated in FIG. 15B, the tension device 1512 engages the lock stop 1515 to force the gear tooth 1511 into the spool gear 1530. The magnitude of tension generated by the tension device 1512 will affect the magnitude of the break-away force. In this example, the tension device 1512 is a coil spring disposed within the tensioned tooth member 1510.

Figure 16:
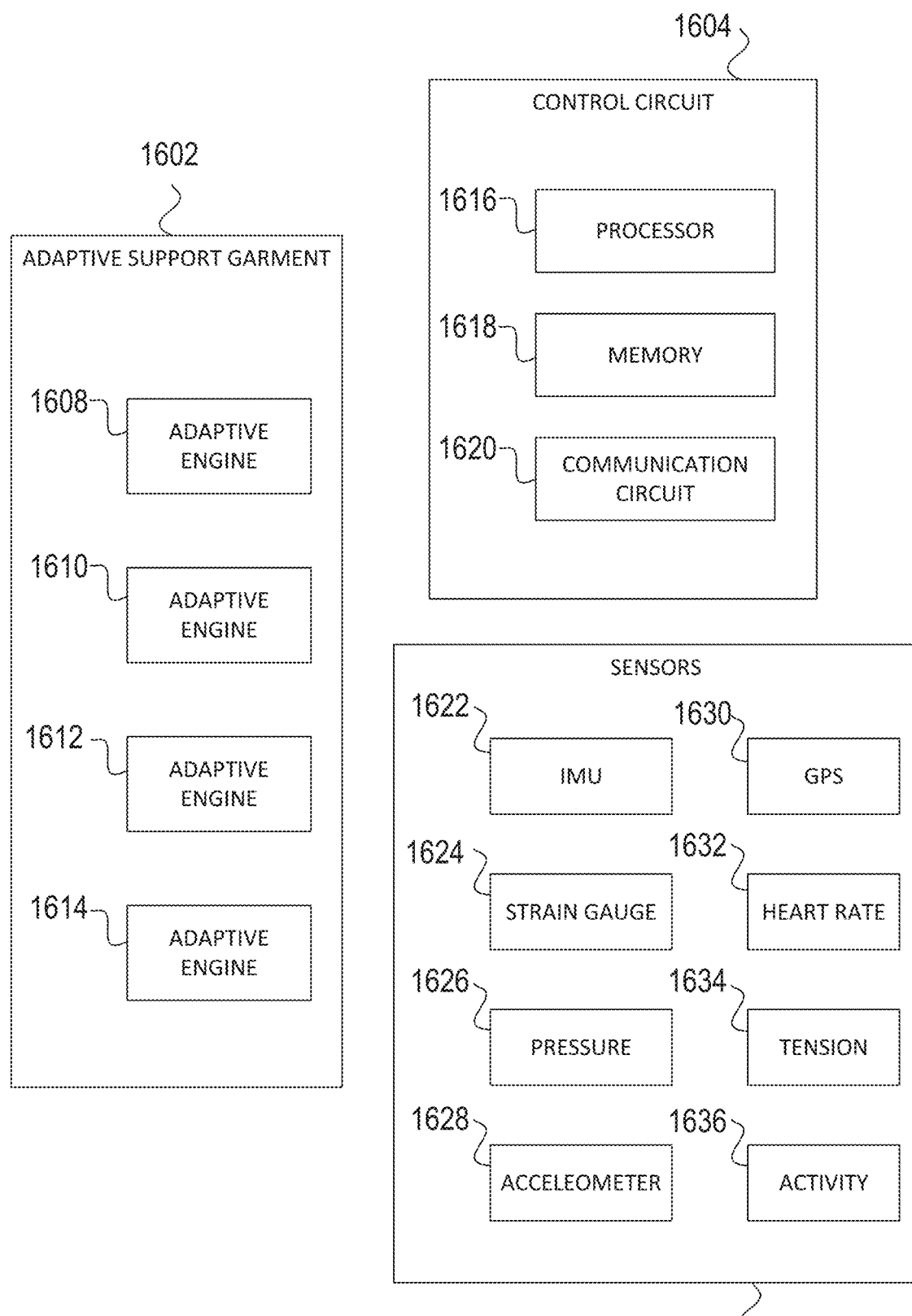
FIG. 16 illustrates an example block diagram of some components of an adaptive support system.

FIG. 16 is a block diagram illustrating components of the adaptive support system, according to some example embodiments. Note, throughout this document the adaptive support system is also referred to as the adaptive support apparel system. In this example, the adaptive support system 1 includes components such as a control circuit 1604, activity sensors 1606, and an adaptive engine 1608, with the adaptive engine 1608 integrated within an adaptive support garment 1602. The adaptive support garment 1602 can include an adaptive supportive region 1610. The adaptive supportive region 1610 includes one or more control lace(s) 1614 configured to selectively become inelastic and/or elastic and a control device 1612 that can generate and/or provide signals that control actuation of the control lace(s) 1614.

The control lace 1614 can include an indicator comprising a haptic feedback device, light source, or other interface means that can indicate whether the control lace and/or support garment control device(s) 1612 is engaged or disengaged, or to indicate a degree to which the control device(s) 1612 is engaged.

The control circuit 1604 includes a processor 1616, a computer-readable memory device memory 1618, and a communication circuit 1620. As discussed above, in some examples the control device 1612 can be integrated within a smart watch 30 or smartphone 35 (FIG. 1). In those examples, the control device 1612 is embodied within a software application running on an operating system (e.g., iOS or Android) for the smart watch 30 or smartphone 35 hardware. Accordingly, the processor 1616 and memory device memory 1618 would be part of the smartphone 35 or smart watch 30. In the illustrated example, the control device 1612 is a standalone device or integrated into an adaptive support garment 1602.

The processor 1616 accesses instructions stored in the memory device memory 1618 to process activity data received over the communication circuit 1620. The activity data can also be stored on the memory device memory 1618 at least during processing operations. The processor 1616 also processes instructions that enable it to generate and transmit, over the communication circuit 1620, commands to the adaptive engine 1608. The commands communicated to the adaptive engine 1608 control activation of the adaptive engine 1608 to change support characteristics of an adaptive support garment.

The control device 1612 receives activity data from activity sensors 1606. In this example, activity sensors 1606 can include any combination of an IMU 1622, an accelerometer 1258, a strain gauge 1624 (e.g., a capacitance-based strain gauge configured to measure displacement information), a pressure sensor 1626, a global positioning system 1630, a temperature sensor, and/or a heart rate (HR sensor 1632), tension sensor 1634, and among other sensors capable of producing data indicative of a user's activity level (e.g., activity sensor 1636). The activity sensors 1606 can include any combination of the listed sensors, and transmits the produced activity data to the control device 1612 over a wireless communication link, such as Bluetooth® LE (Low Energy). Additionally, as alluded to above, the components of system 1 discussed above can be distributed in any combination across devices including a smart watch, a smartphone, a footwear assembly, or an adaptive support garment (e.g., integrated into an adaptive engine).

Additional Notes

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The disclosure, therefore, is not to be taken in a limiting sense, and the scope of various embodiments includes the full range of equivalents to which the disclosed subject matter is entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

EXAMPLES

Each of these non-limiting examples can stand on its own, or can be combined in various permutations or combinations with one or more of the other examples.

Example 1 describes subject matter including an article of apparel for providing dynamic support for an appendage of a person. The article of apparel can include a support garment control device configured to manipulate a support portion of the article of apparel. The support garment control device includes a control lace coupled to a support portion of the article of apparel. The support garment control device (control device) is configured to apply a first tension on the control lace. The control device is also configured to lock the support garment control device at the first tension to inhibit movement of the control lace in response to detecting a change in movement of the person. The control device is further configured to unlock the support garment control device after a pre-determined event subsequent to the change in movement of the person.

In Example 2, the subject matter of Example 1 can optionally include the support garment control device being a modular panel including a mechanical control system and being detachably coupled to the article of apparel.

In Example 3, the subject matter of any one of Examples 1 and 2 can optionally include a sensor adapted for monitoring movements of the person wherein an output from the sensor is evaluated to detect the change in movement of the person.

In Example 4, the subject matter of Example 3 can optionally include evaluating the output from the sensor to predict a future motion of the person to preemptively apply the first tension on the control lace.

In Example 5, the subject matter of any one of Examples 3 or 4 can optionally include evaluating the output from the sensor to determine a duration of time the control lace remains locked at the first tension.

In Example 6, the subject matter of any one of Examples 3 to 5 can optionally include evaluating the output from the sensor to determine a direction of acceleration of the person, the direction of acceleration of the person is used to adjust the first tension according to the direction and acceleration of the person.

In Example 7, the subject matter of any one of Examples 3 to 6 can optionally include evaluating the output from the sensor and in response to a determination the output exceeds a threshold applying the first tension on the control lace and locking the support garment control device at the first tension to inhibit horizontal and/or vertical movement of the control lace.

In Example 8, the subject matter of any one of Examples 1 to 7 can optionally include the support portion of the article of apparel being configured to move freely while supporting the appendage of the person when the support garment control device is unlocked.

In Example 9, the subject matter of any one of Examples 1 to 8 can optionally include the article of apparel having a first support garment control device and a second support garment control device, each of the first and the second support garment control devices individually operable to provide dynamic support for a first and a second appendage of the person.

In Example 10, the subject matter of any one of Examples 1 to 9 can optionally include the support portion being a first support portion, the article further comprises a second support portion wherein the first support portion and the second support portion are configured to receive and support a first and a second breast of the person respectively.

In Example 11, the subject matter of Example 10 can optionally include the article being a sports bra and the support garment control device is impermanently affixed to a front or a back region of the sports bra.

In Example 12, the subject matter of any one of Examples 1 to 11 can optionally include the pre-determined event being an expiration of a time delay since locking the support garment control device.

Example 13 describes a method of providing dynamic support for an appendage of a person using an adaptive support garment. The method can include operations such as applying a first tension, locking a control device, and unlocking a control device. In this example, a support garment control device (control device) can applying a first tension on a control lace coupled to a support portion of the adaptive support garment. The control device can also lock at the first tension to inhibit movement of the control lace in response to detecting a change in movement of the person. The control device can then unlock after a pre-determined event subsequent to the change in movement of the person.

In Example 14 the subject matter of Example 13 can optionally include attaching the support garment control device to a modular panel including a mechanical control system to be detachably integrated into the adaptive support garment.

In Example 15, the subject matter of Example 14 can optionally include attaching the support garment control device to the modular panel includes coupling the control lace to the support garment control device.

In Example 16, the subject matter of Example 15 can optionally include the control device, after unlocking, applying a second tension on the control lace, the second tension being a higher tension than the first tension, locking the support garment control device at the second tension to restrict movement of the control lace in response to detecting a second change in movement of the person, and unlocking the support garment control device after a second pre-determined event subsequent to the second change in movement of the person.

In Example 17, the subject matter of any one of Examples 13 to 16 can optionally include using a sensor adapted for monitoring movements to detect a movement input from of the person and evaluate an output from the sensor to detect the change in movement of the person.

In Example 18, the subject matter of Example 17 can optionally include evaluating the output from the sensor to predict a future motion of the person to preemptively apply the first tension on the control lace.

In Example 19 the subject matter of any one of Examples 17 or 18 can optionally include evaluating the output from the sensor to determine a duration of time the control lace remains locked at the first tension.

In Example 20 the subject matter of any one of Examples 17 to 19 can optionally include evaluating the output from the sensor to determine a direction of acceleration of the person, the direction of acceleration of the person is used to adjust the first tension according to the direction and acceleration of the person.

Example 21 describes a support garment control device for an article of apparel. The control device can include a control lace coupled to a support portion of the article of apparel. The control device can be configured to apply a first tension on the control lace, lock at the first tension to inhibit movement of the control lace in response to detecting a change in movement of a wearer of the article of apparel, and unlock after a pre-determined event subsequent to the change in movement of the wearer.

Example 22 describes a method of controlling a person's breast tissue during exercise using an adaptive support garment. In this example, the method can include applying a first tension, using a support garment control device, on a control lace coupled to a support portion of the adaptive support garment. The method can also include locking the support garment control device to inhibit movement of the control lace in response to detecting a change in movement of the person, and unlocking the support garment control device after a pre-determined event subsequent to the change in movement of the person.

In Example 23 the subject matter of Example 22 can optionally include detecting a movement input from a sensor adapted for monitoring movements of the center of mass of the person and detecting the change in movement of the person includes evaluating the movement input.

In Example 24 the subject matter of Example 23 can optionally include detecting the change in movement input includes detecting an impact event.

In Example 25 the subject matter of any one of Examples 23 and 24 can optionally include the detecting the change in movement input includes averaging a pre-determined number of previous movement cycles to produce a time-averaged waveform representative of a cyclical movement pattern associated with the exercise, and predicting the change in the movement input based on the time-averaged waveform.

In Example 26, the subject matter of Example 25 can optionally include predicting the change in the movement input includes predicting a future impact event based on the time-averaged waveform.

In Example 27, the subject matter of Example 26 can optionally include predicting the future impact event includes identifying a time of the next trough in the time-averaged waveform.

In Example 28, the subject matter of any one of Examples 22 to 27 can optionally include the pre-determined event including a second tension on the control lace coupled to the support portion transgressing a threshold tension.

In Example 29, the subject matter of Example 28 can optionally include the second tension is detected within the support garment control device.

In Example 30, the subject matter of Example 29 can optionally include the threshold tension being controlled by one-way locking fibers adapted to resist relative motion between surfaces below a breaking threshold force.

In Example 31, the subject matter of any one of Examples 22 to 30 can optionally include the pre-determined event being expiration of a time delay since locking the support garment control device.

In Example 32, the subject matter of any one of Examples 22 to 31 can optionally include locking the support garment control device includes applying a second tension on the control lace coupled to the support portion of the adaptive support garment, wherein the second tension is higher than the first tension.

In Example 33, the subject matter of Example 32 can optionally include applying the second tension on the lace includes engaging a rotational dampening device on a spool holding a portion of the lace.

In Example 34, the subject matter of Example 33 can optionally include engaging the rotational dampening device includes changing a back electro-magnetic force on a motor to produce regenerative braking.

In Example 35, the subject matter of any one of Examples 33 and 34 can optionally include engaging the rotational dampening device includes engaging a plurality of friction discs.

In Example 36, the subject matter of any one of Examples 22 to 35 can optionally include locking the support garment control device includes disengaging a solenoid engage a ratchet pawl to limit movement of the control lace to a single direction.

In Example 37, the subject matter of Example 36 can optionally include the ratchet pawl engaging teeth on a lace spool to limit movement of the control lace to retraction within the support garment control device.

In Example 38, the subject matter of any one of Examples 36 and 37 can optionally include unlocking the support garment control device includes engaging the solenoid to disengage the ratchet pawl.

In Example 39, the subject matter of any one of Examples 36 to 38 can optionally include unlocking the support garment control device includes rotation of a locking ring to disengage the ratchet pawl after retraction of a pre-defined length of the control lace.

Example 40 describes a support garment control device for an adaptive support garment. The control device can include a first directional fabric including first directional fibers and coupled to a fixed portion of the adaptive support garment. The control device also includes a second directional fabric including second directional fibers and coupled to a movable control structure portion of the adaptive support garment. The control device further includes a tension device coupled to the movable control structure and configured to apply a tension in a first direction on the movable control structure. In this example, the first directional fibers engage with the second directional fibers to resist movement in a second direction opposite the first direction.

In Example 41, the subject matter of Example 40 can optionally include the control device generating an interaction between the first directional fibers and the second directional fibers to increase the force required to transition movement of the movable control structure from the first direction to the second direction.

In Example 42, the subject matter of Example 41 can optionally include the control device including movement of the movable control structure in the first direction increases compression within a portion of the adaptive support garment.

In Example 43, the subject matter of Example 42, can optionally include the control device including movement of the movable control structure in the second direction decreases compression within the portion of the adaptive support garment.

In Example 44, the subject matter of any one of Examples 40 to 43 can optionally include the first directional fabric being coupled to a fixed shoulder strap portion of the adaptive support garment.

In Example 45, the subject matter of Example 44 can optionally include the control structure being a movable shoulder strap positioned opposite the fixed shoulder strap portion of the adaptive support garment.

In Example 46, the subject matter of any one of Examples 40 to 45 can optionally include the fixed portion of the adaptive support garment being a cylindrical body containing the movable control structure and the tension device.

In Example 47, the subject matter of Example 46 can optionally include the tension device is a torsion spring configured to apply a constant force to the movable control structure.

In Example 48, the subject matter of Example 46 can optionally include the movable control structure being a lace spool rotationally disposed within the cylindrical body.

In Example 49, the subject matter of Example 48 can optionally include the second directional fabric is disposed around an external surface of the lace spool opposite the first directional fabric disposed around an internal surface of the cylindrical body.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein, such as the motion control or digital control system method of operation examples, can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. An Abstract, if provided, is included to comply with United States rule 37 C.F.R. § 1.72(b), to allow the reader to quickly ascertain the nature of the technical disclosure. It is submitted with the understanding that it will not be used to interpret or limit the scope or meaning of the claims. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An adaptive support garment comprising:
a first directional fabric including first directional fibers, the first directional fabric coupled to a fixed portion of the adaptive support garment, wherein the first directional fabric is a mohair type fabric;
a second directional fabric including second directional fibers, the second directional fabric coupled to a movable control structure portion of the adaptive support garment, wherein the second directional fabric is a mohair type fabric; and
a tension device coupled to the movable control structure portion and configured to apply a tension in a first direction on the movable control structure portion;
wherein the first directional fibers engage with the second directional fibers to resist movement in a second direction opposite the first direction.

2. The adaptive support garment of claim 1, wherein interaction between the first directional fibers and the second directional fibers increase a force required to transition movement of the movable control structure portion from the first direction to the second direction.

3. The adaptive support garment of claim 2, wherein movement of the movable control structure portion in the first direction increases compression within a portion of the adaptive support garment.

4. The adaptive support garment of claim 3, wherein movement of the movable control structure portion in the second direction decreases compression within the portion of the adaptive support garment.

5. The adaptive support garment of claim 1, wherein the fixed portion is a fixed shoulder strap portion, wherein the first directional fabric is coupled to the fixed shoulder strap portion of the adaptive support garment.

6. The adaptive support garment of claim 5, wherein the movable control structure portion is a movable shoulder strap positioned opposite the fixed shoulder strap portion of the adaptive support garment.

7. The adaptive support garment of claim 1, wherein the fixed portion of the adaptive support garment includes a cylindrical body containing the movable control structure portion and the tension device.

8. The adaptive support garment of claim 7, wherein the tension device is a torsion spring configured to apply a constant force to the movable control structure portion.

9. The adaptive support garment of claim 7, wherein the movable control structure portion is a lace spool rotationally disposed within the cylindrical body.

10. The adaptive support garment of claim 9, wherein the second directional fabric is disposed around an external surface of the lace spool opposite the first directional fabric disposed around an internal surface of the cylindrical body.

11. The adaptive support garment of claim 1, wherein the first directional fabric and the second directional fabric are made from a common type of directional fabric positioned in opposing orientation.

12. An adaptive support garment comprising:
a movable support member including a first mohair fabric, the first mohair fabric including directional fibers orientated in a first direction;
a fixed support member including a second mohair fabric, the second mohair fabric including directional fibers oriented in a second direction opposing the first direction; and
a bias member coupled to the movable support member and applying a first tension in a first direction on the movable support member to provide initial support to a portion of the adaptive support garment coupled to the movable support member.

13. The adaptive support garment of claim 12, wherein interaction between the first mohair fabric and the second mohair fabric increase a force required to overcome the first tension and transition movement of the movable support member to a second direction.

14. The adaptive support garment of claim 13, wherein movement of the movable support member in the first direction increases compression within a portion of the adaptive support garment.

15. The adaptive support garment of claim 14, wherein movement of the movable support member in the second direction decreases compression within the portion of the adaptive support garment.

16. The adaptive support garment of claim 12, wherein the fixed support member is a fixed shoulder strap portion, wherein the second mohair fabric is coupled to the fixed shoulder strap portion of the adaptive support garment.

17. The adaptive support garment of claim 16, wherein the movable support member is a movable shoulder strap positioned opposite the fixed shoulder strap portion of the adaptive support garment.

18. The adaptive support garment of claim 12, wherein the fixed support member of the adaptive support garment includes a cylindrical body containing the movable support member and the bias member.

19. The adaptive support garment of claim 18, wherein the bias member is a torsion spring configured to apply a constant force to the movable support member.

20. An adaptive support garment comprising:
a first directional fabric including first directional fibers, the first directional fabric coupled to a fixed portion of the adaptive support garment;
a second directional fabric including second directional fibers, the second directional fabric coupled to a movable control structure of the adaptive support garment; and
a tension device coupled to the movable control structure and configured to apply a tension in a first direction on the movable control structure;
wherein the first directional fibers engage with the second directional fibers to resist movement in a second direction opposite the first direction, and
wherein the fixed portion of the adaptive support garment includes a cylindrical body containing the movable control structure and the tension device.

21. The adaptive support garment of claim 20, wherein the tension device is a torsion spring configured to apply a constant force to the movable control structure.

22. The adaptive support garment of claim 20, wherein the movable control structure is a lace spool rotationally disposed within the cylindrical body.

23. The adaptive support garment of claim 22, wherein the second directional fabric is disposed around an external surface of the lace spool opposite the first directional fabric disposed around an internal surface of the cylindrical body.

24. The adaptive support garment of claim 20, wherein interaction between the first directional fibers and the second directional fibers increase a force required to transition movement of the movable control structure from the first direction to the second direction.

25. The adaptive support garment of claim 24, wherein movement of the movable control structure in the first direction increases compression within a portion of the adaptive support garment.

26. The adaptive support garment of claim 25, wherein movement of the movable control structure in the second direction decreases compression within the portion of the adaptive support garment.

* * * * *